US008846579B2

(12) United States Patent
Hoogenboom et al.

(10) Patent No.: US 8,846,579 B2
(45) Date of Patent: Sep. 30, 2014

(54) LIGAND SCREENING AND DISCOVERY

(71) Applicant: Dyax Corp., Burlington, MA (US)

(72) Inventors: Hendricus Renerus Jacobus Mattheus Hoogenboom, Maastricht (NL); Jurgen Mullberg, Aachen (DE); Robert C. Ladner, Ijamsville, MD (US)

(*) Notice: Subject to any disclaimer, the term of this patent is extended or adjusted under 35 U.S.C. 154(b) by 0 days.

(21) Appl. No.: 13/867,806

(22) Filed: Apr. 22, 2013

(65) Prior Publication Data

US 2013/0274112 A1  Oct. 17, 2013

Related U.S. Application Data

(62) Division of application No. 11/763,251, filed on Jun. 14, 2007, now Pat. No. 8,445,410, which is a division of application No. 10/383,902, filed on Mar. 7, 2003, now Pat. No. 7,244,592.

(60) Provisional application No. 60/362,403, filed on Mar. 7, 2002.

(51) Int. Cl.
*C40B 50/06* (2006.01)
*C07K 16/00* (2006.01)
*C12N 15/85* (2006.01)
*C12N 15/10* (2006.01)

(52) U.S. Cl.
CPC ........ *C12N 15/1058* (2013.01); *C12N 2830/55* (2013.01); *C07K 16/00* (2013.01); *C12N 15/85* (2013.01); *C12N 2830/002* (2013.01); *C12N 2840/203* (2013.01); *C12N 2800/108* (2013.01); *C07K 2317/56* (2013.01)
USPC .......................................................... 506/26

(58) Field of Classification Search
None
See application file for complete search history.

(56) References Cited

U.S. PATENT DOCUMENTS

| 5,789,208 | A | 8/1998 | Sharon |
| 5,955,358 | A | 9/1999 | Huse |
| 6,096,551 | A | 8/2000 | Barbas et al. |
| 6,297,053 | B1 | 10/2001 | Stemmer |
| 6,329,511 | B1 | 12/2001 | Vasquez et al. |
| 6,339,070 | B1 | 1/2002 | Emery et al. |
| 6,479,243 | B1 | 11/2002 | Wigler et al. |
| 7,244,592 | B2 | 7/2007 | Hoogenboom et al. |
| 8,445,410 | B2 | 5/2013 | Hoogenboom et al. |
| 2002/0025536 | A1 | 2/2002 | Gyuris et al. |
| 2002/0106729 | A1 | 8/2002 | Bleck |

OTHER PUBLICATIONS

Altshuler et al., Continuous hybridoma growth and monoclonal antibody production in hollow fiber reactors-separators. Biotechnol Bioeng. May 1986;28(5):646-58.

(Continued)

*Primary Examiner* — Christian Boesen
(74) *Attorney, Agent, or Firm* — Wolf, Greenfield & Sacks, P.C.

(57) ABSTRACT

Disclosed is a method that includes: (i) providing a plurality of initial nucleic acid cassettes that include: a) a first coding region encoding a first immunoglobulin variable domain, b) a second coding region encoding a second immunoglobulin variable domain, and c) a ribosomal binding site disposed between the first and second coding regions for translation of the second polypeptide in a first expression system, wherein the first and second coding regions are in the same translational orientation; (ii) modifying each nucleic acid cassette of the plurality in a single reaction mixture so that it is functional in a second expression system, wherein the first and second region remain physically attached during the modifying; (iii) introducing each modified nucleic acid cassette into a mammalian cell to produce a mixture of transfected cells; and (iv) expressing each modified nucleic acid cassette in the transfected cells.

29 Claims, 31 Drawing Sheets

(56) References Cited

OTHER PUBLICATIONS

Barbas et al., Assembly of combinatorial antibody libraries on phage surfaces: the gene III site. Proc Natl Acad Sci USA. Sep. 15, 1991;88(18):7978-82.

Borth et al., Analysis of changes during subclone development and ageing of human antibody-producing heterohybridoma cells by northern blot and flow cytometry. J Biotechnol. Jan. 8, 1999;67(1):57-66.

Borth et al., Efficient selection of high-producing subclones during gene amplification of recombinant Chinese hamster ovary cells by flow cytometry and cell sorting. Biotechnol Bioeng. 2000-2001;71(4):266-73.

De Haard et al., P, Arends JW, Hoogenboom HR. A large non-immunized human Fab fragment phage library that permits rapid isolation and kinetic analysis of high affinity antibodies. J Biol Chem. Jun. 25, 1999;274(26):18218-30.

De Wildt et al., Antibody arrays for high-throughput screening of antibody-antigen interactions. Nat Biotechnol. Sep. 2000;18(9):989-94.

Den et al., A bidirectional phage display vector for the selection and mass transfer of polyclonal antibody libraries. J Immunol Methods. Jan. 1, 1999;222(1-2):45-57.

Glennie et al., Clinical trials of antibody therapy. Immunol Today. Aug. 2000;21(8):403-10.

Holmes et al., Improved cell line development by a high throughput affinity capture surface display technique to select for high secretors. J Immunol Methods. Nov. 19, 1999;230(1-2):141-7.

Leo et al., Identification of a monoclonal antibody specific for a murine T3 polypeptide. Proc Natl Acad Sci USA. Mar. 1987;84(5):1374-8.

Liang et al., Baculovirus expression cassette vectors for rapid production of complete human IgG from phage display selected antibody fragments. J Immunol Methods. Jan. 1, 2001;247(1-2):119-30.

Mann et al., The effect of erythropoietin administration on murine bone marrow chimeras. Immunol Lett. Jan. 1996;49(1-2):15-20.

Manz et al., Analysis and sorting of live cells according to secreted molecules, relocated to a cell-surface affinity matrix. Proc Natl Acad Sci U S A. Mar. 14, 1995;92(6):1921-5.

Norderhaug et al., Versatile vectors for transient and stable expression of recombinant antibody molecules in mammalian cells. J Immunol Methods. May 12, 1997;204(1):77-87.

Persic et al., An integrated vector system for the eukaryotic expression of antibodies or their fragments after selection from phage display libraries. Gene. Mar. 10, 1997;187(1):9-18.

Santora et al., Generation of a polyclonal fab phage display library to the human breast carcinoma cell line BT-20. Comb Chem High Throughput Screen. Feb. 2000;3(1):51-7.

Sharon et al., Recombinant polyclonal antibody libraries. Comb Chem High Throughput Screen. Jun. 2000;3(3):185-96.

Shields et al., Lack of fucose on human IgG1 N-linked oligosaccharide improves binding to human Fcgamma RIII and antibody-dependent cellular toxicity. J Biol Chem. Jul. 26, 2002;277(30):26733-40. Epub May 1, 2002.

Sondermann et al., The 3.2-A crystal structure of the human IgG1 Fc fragment-Fc gammaRIII complex. Nature. Jul. 20, 2000;406(6793):267-73.

Yang et al., CDR walking mutagenesis for the affinity maturation of a potent human anti-HIV-1 antibody into the picomolar range. J Mol Biol. Dec. 1, 1995;254(3):392-403.

*: Asc1 and Mlu1 generate a compatible 5' overhang

```
                    ApaI
                    BbvII
                    Bsc91I         NheI
  1   GCCTCCACCAAGGGCCCATCGGTCTTCCCGCTAGCACCCTCCTCCAAGAGCACCTCTGGG
      CGGAGGTGGTTCCCGGGTAGCCAGAAGGGCGATCGTGGGAGGAGGTTCTCGTGGAGACCC
       A  S  T  K  G  P  S  V  F  P  L  A  P  S  S  K  S  T  S  G

PinAI
                        EcoNI                 AgeI       Tth111I
 61   GGCACAGCGGCCCTGGGCTGCCTGGTCAAGGACTACTTCCCCGAACCGGTGACGGTGTCG
      CCGTGTCGCCGGGACCCGACGGACCAGTTCCTGATGAAGGGGCTTGGCCACTGCCACAGC
       G  T  A  A  L  G  C  L  V  K  D  Y  F  P  E  P  V  T  V  S

BbeI
                EheI                                          AccIII
                NarI                                          BspMII
121   TGGAACTCAGGCGCCCTGACCAGCGGCGTCCACACCTTCCCGGCTGTCCTACAGTCCTCC
      ACCTTGAGTCCGCGGGACTGGTCGCCGCAGGTGTGGAAGGGCCGACAGGATGTCAGGAGG
       W  N  S  G  A  L  T  S  G  V  H  T  F  P  A  V  L  Q  S  S

BstXI
181   GGACTCTACTCCCTCAGCAGCGTAGTGACCGTGCCCTCCAGCAGCTTGGGCACCCAGACC
      CCTGAGATGAGGGAGTCGTCGCATCACTGGCACGGGAGGTCGTCGAACCCGTGGGTCTGG
       G  L  Y  S  L  S  S  V  V  T  V  P  S  S  S  L  G  T  Q  T

241   TACATCTGCAACGTGAATCACAAGCCCAGCAACACCAAGGTGGACAAGAAAGTTGAGCCC
      ATGTAGACGTTGCACTTAGTGTTCGGGTCGTTGTGGTTCCACCTGTTCTTTCAACTCGGG
       Y  I  C  N  V  N  H  K  P  S  N  T  K  V  D  K  K  V  E  P

AlwNI             BbvII
301   AAATCTTGTGACAAAACTCACACATGCCCACCGTGCCCAGCACCTGAACTCCTGGGGGGA
      TTTAGAACACTGTTTTGAGTGTGTACGGGTGGCACGGGTCGTGGACTTGAGGACCCCCCT
       K  S  C  D  K  T  H  T  C  P  P  C  P  A  P  E  L  L  G  G

MstII
                                                              CvnI
                                                              Bsu36I
           Eam1105I                        BspHI              SauI
361   CCGTCAGTCTTCCTCTTCCCCCCAAAACCCAAGGACACCCTCATGATCTCCCGGACCCCT
      GGCAGTCAGAAGGAGAAGGGGGGTTTTGGGTTCCTGTGGGAGTACTAGAGGGCCTGGGGA
       P  S  V  F  L  F  P  P  K  P  K  D  T  L  M  I  S  R  T  P

DrdI
                                  Bsu36I
                                  BbvII
                                  Bsc91I
421   GAGGTCACATGCGTGGTGGTGGACGTGAGCCACGAAGACCCTGAGGTCAAGTTCAACTGG
      CTCCAGTGTACGCACCACCACCTGCACTCGGTGCTTCTGGGACTCCAGTTCAAGTTGACC
       E  V  T  C  V  V  V  D  V  S  H  E  D  P  E  V  K  F  N  W
```

FIG. 22A

```
                                               SstII
                                               SacII
                                               Mlu113I
481  TACGTGGACGGCGTGGAGGTGCATAATGCCAAGACAAAGCCGCGGGAGGAGCAGTACAAC
     ATGCACCTGCCGCACCTCCACGTATTACGGTTCTGTTTCGGCGCCCTCCTCGTCATGTTG
      Y  V  D  G  V  E  V  H  N  A  K  T  K  P  R  E  E  Q  Y  N

EcoNI
541  AGCACGTACCGTGTGGTCAGCGTCCTCACCGTCCTGCACCAGGACTGGCTGAATGGCAAG
     TCGTGCATGGCACACCAGTCGCAGGAGTGGCAGGACGTGGTCCTGACCGACTTACCGTTC
      S  T  Y  R  V  V  S  V  L  T  V  L  H  Q  D  W  L  N  G  K

Eco31I
601  GAGTACAAGTGCAAGGTCTCCAACAAAGCCCTCCCAGCCCCCATCGAGAAAACCATCTCC
     CTCATGTTCACGTTCCAGAGGTTGTTTCGGGAGGGTCGGGGGTAGCTCTTTTGGTAGAGG
      E  Y  K  C  K  V  S  N  K  A  L  P  A  P  I  E  K  T  I  S

SmaI
                        Bsp1407I                          XmaI
661  AAAGCCAAAGGGCAGCCCCGAGAACCACAGGTGTACACCCTGCCCCCATCCCGGGATGAG
     TTTCGGTTTCCCGTCGGGGCTCTTGGTGTCCACATGTGGGACGGGGGTAGGGCCCTACTC
      K  A  K  G  Q  P  R  E  P  Q  V  Y  T  L  P  P  S  R  D  E

BspMI
721  CTGACCAAGAACCAGGTCAGCCTGACCTGCCTGGTCAAAGGCTTCTATCCCAGCGACATC
     GACTGGTTCTTGGTCCAGTCGGACTGGACGGACCAGTTTCCGAAGATAGGGTCGCTGTAG
      L  T  K  N  Q  V  S  L  T  C  L  V  K  G  F  Y  P  S  D  I

781  GCCGTGGAGTGGGAGAGCAATGGGCAGCCGGAGAACAACTACAAGACCACGCCTCCCGTG
     CGGCACCTCACCCTCTCGTTACCCGTCGGCCTCTTGTTGATGTTCTGGTGCGGAGGGCAC
      A  V  E  W  E  S  N  G  Q  P  E  N  N  Y  K  T  T  P  P  V

BspMI
841  CTGGACTCCGACGGCTCCTTCTTCCTCTACAGCAAGCTCACCGTGGACAAGAGCAGGTGG
     GACCTGAGGCTGCCGAGGAAGAAGGAGATGTCGTTCGAGTGGCACCTGTTCTCGTCCACC
      L  D  S  D  G  S  F  F  L  Y  S  K  L  T  V  D  K  S  R  W

BbvII
         Bsc91I XmnI                 NsiI                      SapI
901  CAGCAGGGGAACGTCTTCTCATGCTCCGTGATGCATGAGGCTCTGCACAACCACTACACG
     GTCGTCCCCTTGCAGAAGAGTACGAGGCACTACGTACTCCGAGACGTGTTGGTGATGTGC
      Q  Q  G  N  V  F  S  C  S  V  M  H  E  A  L  H  N  H  Y  T

961  CAGAAGAGCCTCTCCCTGTCTCCGGGTAAATGA     (SEQ ID NO:4)
     GTCTTCTCGGAGAGGGACAGAGGCCCATTTACT     (SEQ ID NO:5)
      Q  K  S  L  S  L  S  P  G  K  *     (SEQ ID NO:6)
```

FIG. 22B

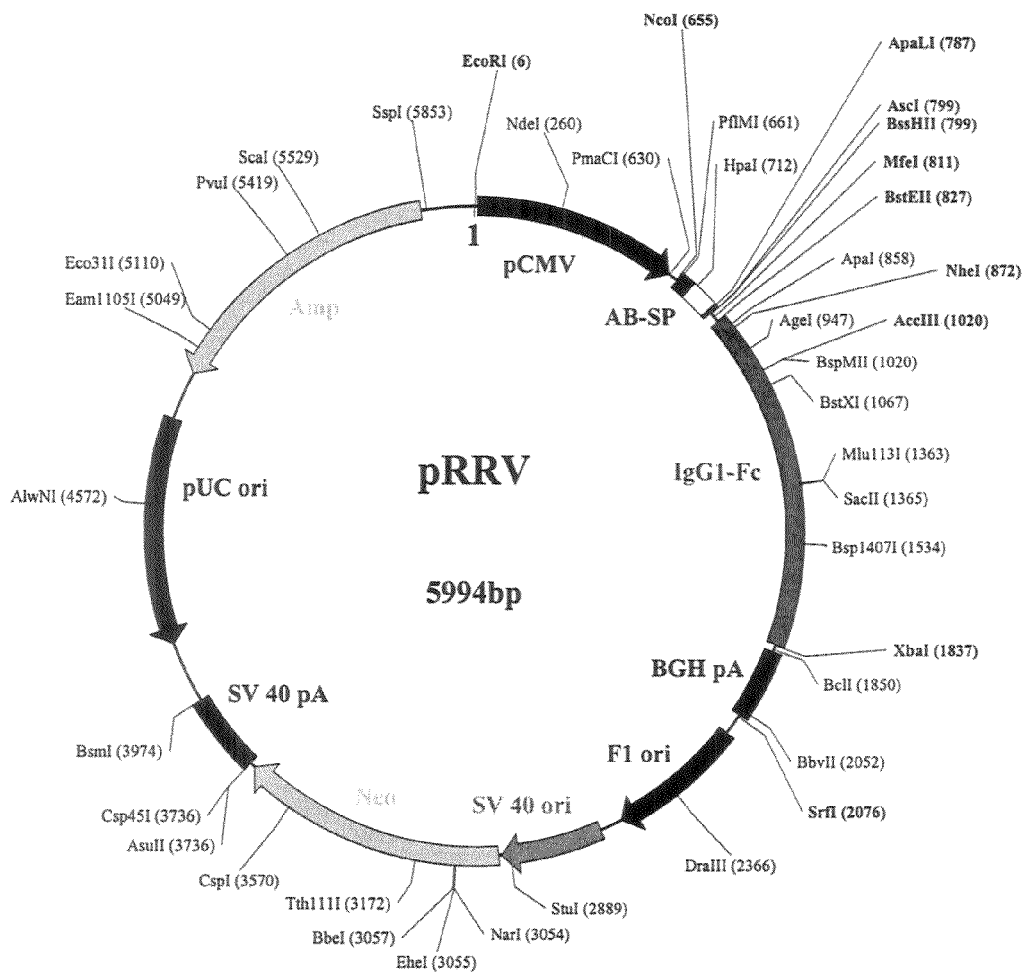

```
NcoI(655)        Ab-leader
CCATGGGATGGAGCTGTATCATCCTCTTCTTGGTAGCAACAGCTACAGGTAAGGGGGTTAA
GGTACCCTACCTCGACATAGTAGGAGAAGAACCATCGTTGTCGATGTCCATTCCCCAATT
    M  G  W  S  C  I  I  L  F  L  V  A  T  A  T  (SEQ ID NO:9)

CAGTAGCAGGCTTGAGGTCTGGACATATATATGGGTGACAATGACATCCACTTTGCCTTT
GTCATCGTCCGAACTCCAGACCTGTATATATACCCACTGTTACTGTAGGTGAAACGGAAA

BssH2
        ApaLI       AscI          MfeI              BstEII
CTCTCCACAGGCGTGCACTCTAAGGCGCGCCATAGGCAATTGCCCGCGCTGTGGTCACCG
GAGAGGTGTCCGCACGTGAGATTCCGCGCGGTATCCGTTAACGGGCGCGACACCAGTGGC
          G  V  H  S  (SEQ ID NO:10)                    V  T

VH-FR4/CH1                  NheI(872)
TCTCAAGCGCCTCCACCAAGGGCCCATCGGTCTTCCCGCTAGCAC   (SEQ ID NO:7)
AGAGTTCGCGGAGGTGGTTCCCGGGTAGCCAGAAGGGCGATCGTG   (SEQ ID NO:8)
  V  S  S  A  S  T  K  G  P  S  V  F  P  L  A   (SEQ ID NO:11)
```

FIG. 23

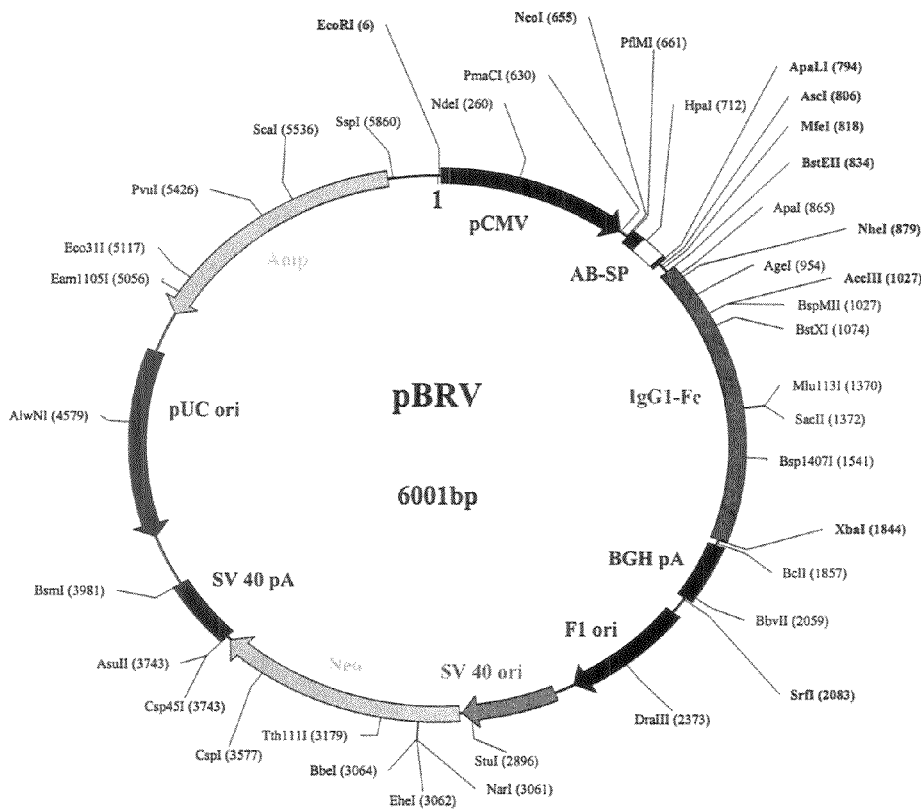

```
        NcoI(655)        Ab-leader
CCATGGGATGGAGCTGTATCATCCTCTTCTTGGTAGCAACAGCTACAGGTAAGGGGTTAA
GGTACCCTACCTCGACATAGTAGGAGAAGAACCATCGTTGTCGATGTCCATTCCCCAATT
  M  G  W  S  C  I  I  L  F  L  V  A  T  A  T  (SEQ ID NO:14)

CAGTAGCAGGCTTGAGGTCTGGACATATATATGGGTGACAATGACATCCACTTTGCCTTT
GTCATCGTCCGAACTCCAGACCTGTATATATACCCACTGTTACTGTAGGTGAAACGGAAA

BssH2
           BssH2      ApaLI       AscI          MfeI
CTCTCCACAGGCGCGCACAGTGCACTCTAAGGCGCGCCATAGGCAATTGCCCGCGCTGTG
GAGAGGTGTCCGCGCGTGTCACGTGAGATTCCGCGCGGTATCCGTTAACGGGCGCGACAC
          G  A  H  S  A  (SEQ ID NO:15)

BstE2            VH-FR4/CH1                NheI(879)
GTCACCGTCTCAAGCGCCTCCACCAAGGGCCCATCGGTCTTCCCGCTAGCACC  (SEQ ID NO:12)
CAGTGGCAGAGTTCGCGGAGGTGGTTCCCGGGTAGCCAGAAGGGCGATCGTGG  (SEQ ID NO:13)
  V  T  V  S  S  A  S  T  K  G  P  S  V  F  P  L  A   (SEQ ID NO:16)
```

FIG. 24

```
NcoI            Ab-leader / VH                BssH2              MfeI
CCATGGGATGGAGCTGTATCATCCTCTTCTTGGTAGCAACAGCTACAGGCGCGCACTCCGAAGTTCAATTG
GGTACCCTACCTCGACATAGTAGGAGAAGAACCATCGTTGTCGATGTCCGCGCGTGAGGCTTCAAGTTAAC
   M  G  W  S  C  I  I  L  F  L  V  A  T  A  T  G  A  H  S  E  V  Q  L BstE2   NheI NotI
TGAGGTCACCGCTAGCGGCCGC  (SEQ ID NO:23)
ACTCCAGTGGCGATCGCCGGCG  (SEQ ID NO:24)
                        (SEQ ID NO:25)
```

LIGAND SCREENING AND DISCOVERY

CROSS-REFERENCE TO RELATED APPLICATIONS

This application is a divisional application of U.S. patent application Ser. No. 11/763,251, filed Jun. 14, 2007 (now allowed), which is a divisional application of U.S. patent application Ser. No. 10/383,902, now U.S. Pat. No. 7,244,592, filed Mar. 7, 2003, which claims benefit of priority to U.S. Provisional Patent Application Ser. No. 60/362,403, filed Mar. 7, 2002, the contents of the aforementioned applications are incorporated by reference in their entirety.

BACKGROUND

Recombinant techniques have allowed the discovery of artificial and natural proteins that have broad applications in the development of therapeutics, diagnostic agents (e.g., for imaging or binding assays), enzymes, and agents for affinity separations. One such recombinant technique is the construction of nucleic acid libraries that include diverse sequence content. Libraries can be screened by hybridization, genetic complementation, and polypeptide expression, among other activities. One challenge for the development of recombinant proteins is the rapid identification of proteins that are functional in the context of their ultimate therapeutic or industrial use.

One exemplary class of proteins being developed as therapeutics includes antibodies. The properties of antibodies are being exploited in order to design agents that bind to human target molecules, so-called, "self-antigens." For example, a number of monospecific antibodies have been approved as human therapeutics. These include Orthoclone OKT3, which targets CD3 antigen; ReoPro, which targets GP IIb/IIIa; Rituxan, which targets CD20; Zenapax and Simulect, which target interleukin-2 receptors; Herceptin, which targets the HER2-receptor; Remicade, which targets tumor necrosis factor; Synagis, which targets the F protein of respiratory syncytial virus; Mylotarg, which targets CD33; and Campath, which targets CD52 (see, e.g., Carter (2001) *Nature Reviews* 1:118-129; Ezzell (2001) *Scientific American* October 2001, pages 36-41; Garber (2001) *Nat. Biotechnol.* 19:184-185).

SUMMARY

Nucleic acids encoding hetero-oligomeric receptors are reformatted to facilitate shuttling between expression systems. The methods can be used, for example, to effectively transition multiple candidates from a first library screen to a biological screen or other regime.

In one aspect, the invention features a method that includes: (i) providing a plurality of initial nucleic acid cassettes that include a) a first coding region encoding a first immunoglobulin variable domain, b) a second coding region encoding a second immunoglobulin variable domain, and c) a ribosomal binding site disposed between the first and second coding regions for translation of the second polypeptide in a first expression system, wherein the first and second coding regions are in the same translational orientation, and the first and second coding regions encode at least segments of subunits of an antigen binding protein; (ii) modifying each nucleic acid cassette of the plurality in a single reaction mixture so that it is functional in a second expression system, wherein the first and second region remain physically attached during the modifying; (iii) introducing each modified nucleic acid cassette into a mammalian cell to produce a mixture of transfected cells; and (iv) screening the mixture of transfected cells using FACS to identify transfected cell that produces a least a threshold amount of a full Ig that includes the combination of first and second immunoglobulin variable domain present in an initial cassette. The method can be used for expressing a hetero-multimeric protein, e.g., an antigen binding protein such as a Fab and/or a full length antibody, a T cell receptor, an MHC complex, and so forth.

The first and second coding regions can be transcribed as a single transcript. In one embodiment, prior to the modifying, the nucleic acid cassette includes a promoter (e.g., a prokaryotic promoter) that regulates transcription of a single transcript that includes the first and second coding regions and is disposed upstream of the first coding region. The regions can further include a sequence encoding an immunoglobulin constant domain (e.g., CL or CH1).

In one embodiment, the first expression system is prokaryotic and the second expression system is eukaryotic. For example, the second expression system is mammalian or fungal (e.g., yeast). In a particular example, the first expression system is prokaryotic (e.g., filamentous bacteriophage display) and the second expression system is mammalian. In another particular example, the first expression system is prokaryotic (e.g., filamentous bacteriophage display) and the second expression system is yeast.

In another embodiment, the first and second expression systems are eukaryotic. For example, the first expression system is yeast and the second expression system is mammalian.

In another embodiment, one of the expression systems can also be an in vitro translation system, e.g., an in vitro transcription-translation system or an eukaryotic in vitro translation system.

The modifying can include inserting an internal ribosome entry site between the first and second coding regions. The modifying can also include removing a segment that includes the ribosomal binding site.

The modifying can include linking a eukaryotic promoter to the cassette upstream of the first coding region such that the promoter regulates transcription of a transcript that includes the first coding region or the first and second coding region. In one example, the modifying can further include removing the prokaryotic promoter (before or after the inserting). In another example, the prokaryotic promoter is retained, and, e.g., the eukaryotic promoter is linked upstream, downstream, or within the eukaryotic promoter.

The eukaryotic promoter may be functional, for example, in a mammalian, yeast, and/or plant cell, e.g., a human cell or a *Saccharomyces* cell.

The modifying can include linking (e.g., inserting) a segment that includes a eukaryotic promoter between the first and second coding region. The eukaryotic promoter linked at this position is typically in addition to the eukaryotic promoter positioned upstream of the cassette. The segment can also include a leader, e.g., a leader that supports eukaryotic processing, e.g., a bifunctional leader or an exclusively eukaryotic leader.

The modifying can include linking (e.g., inserting) a segment that includes an internal ribosome entry site (IRES) (e.g., a viral IRES) between the first and second coding regions.

The segment can further include a signal sequence functional in a mammalian cell. The segment can further include a polyA addition regulatory sequence. In one embodiment, the segment includes both a eukaryotic polyA addition regulatory sequence and a eukaryotic promoter, e.g., a second eukaryotic promoter.

In a related embodiment, the segment includes a signal sequence functional in a mammalian cell.

In one embodiment, prior to or after the modifying, the second coding region of the nucleic acid cassette is in frame with a sequence encoding a first fusion polypeptide. For example, the first fusion polypeptide can include the polypeptide encoded by the first coding region and a bacteriophage coat protein or fragment thereof (e.g., a minor coat protein such as gene III or the gene III stump.).

In one example, the modifying includes removing the sequence encoding the first fusion polypeptide, e.g., removing a sequence that encodes a bacteriophage coat protein or fragment thereof. The modifying can include attaching a different sequence encoding a second fusion polypeptide in frame to the second coding region. For example, the second fusion polypeptide may include an immunoglobulin heavy chain CH2 and CH3, Hinge-CH2-CH3, or other constant domains. The Fc region, which typically includes Hinge-CH2-CH3 can also include a modification that alters binding to an Fc receptor relative to another Fc receptor. The second polypeptide can further include other functional domains, e.g., a non-immunoglobulin functional domain, e.g., a localization signal, e.g., a cell attachment sequence. The second polypeptide can also independently include a polypeptide tag. In one embodiment, the first or second fusion includes a yeast extracellular domain or portion thereof.

In an embodiment, as a (direct or indirect) fusion of one of the immunoglobulin variable domains to the Fc domain includes a sequence modification that alters binding to an Fc receptor relative to another Fc receptor, e.g., the Fc domain is artificial and selectively binds to Fc receptors.

In one embodiment, the modifying includes (in any order, or concurrently) a) replacing a nucleic acid segment between the first and second coding regions, b) replacing nucleic acid 5' of the coding strand of the first coding region and c) replacing nucleic acid 3' of the coding strand of the second coding region. For example, b) may be c) concurrent.

In one embodiment, the nucleic acid 5' of the coding strand is directly adjacent to the first coding region.

The modifying can include adding or removing one or more nucleotides but maintaining linkage between the first and second coding regions. With respect to the coding strand, the modifying can include: a) maintaining linkage between the 5' terminus of the first coding region and the 3' terminus of the second coding region, while disrupting the linkage between the 3' terminus of the first coding region and the 5' terminus of the second coding region; and b) maintaining linkage between the 5' terminus of the first coding region and the 3' terminus of the second coding region, while disrupting the linkage between the 3' terminus of the first coding region and the 5' terminus of the second coding region. The order can be reversed.

The nucleic acid 5' of the coding strand can include one or more of: an untranslated region, a ribosome binding site, a promoter, a segment encoding a leader sequence or portion thereof.

In another embodiment, the modifying includes only a single cloning step. The segment between the first and second coding regions includes a sequence encoding a signal sequence that is functional in two different expression systems. The signal sequence is fused to the second coding region. For example, the signal sequence is functional in both prokaryotic and eukaryotic cells, e.g., it includes VHA at the −3, −2, −1 positions, or it has at least 80%, 90%, 95%, or 100% identity to a natural signal sequence that is functional in both systems, e.g., a beta-lactamase signal sequence. A single cloning step can be used to alter the in-frame fusion of the second coding region and a third coding region (e.g., encoding an Fc domain or a gene III protein or fragment thereof).

The modifying can include annealing and extending a primer that includes a restriction site, e.g., that is endogenous or exogenous to the nucleic acid cassette prior to the modifying. For example, PCR can be used.

The modifying can include restricting the cassette using one or more of: ApaLI, AscI, MfeI, BstEII, NotI, XbaI, NcoI, PstI, NheI, SfiI and BssH2, e.g., including combinations such as AscI and MfeI; AscI and SfiI; ApaL1 and NotI; ApaL1 and NheI; or ApaL1 and BstEII.

In one embodiment, the VL domain of the expressed heteromeric protein includes a naturally occurring N-terminus after leader sequence processing.

The modified nucleic acid cassette can include a chromatin control sequence (e.g., an insulator, a locus control region, or a chromatin opening element). The chromatin control sequence can be upstream of the first coding region, e.g., upstream of a promoter that is operably linked to the first coding region, or down stream of the second coding region, etc. The control sequence might even be inserted between the first and second coding regions.

In another aspect, the invention features a method that includes: (i) providing a plurality of nucleic acid cassettes, each nucleic acid cassette that includes a) a first coding region encoding a first polypeptide, b) a second coding region encoding a second polypeptide, and c) a ribosomal binding site disposed between the first and second coding regions for translation of the second polypeptide in a first expression system, wherein the first and second coding regions are in the same translational orientation, and the first and second coding regions can be transcribed as a single transcript; and the first and second coding regions encode at least segments of subunits of a hetero-multimeric protein, and (ii) modifying each nucleic acid cassette of the plurality to produce second nucleic acids, each second nucleic acid being functional in a second expression system, wherein the first and second coding regions remain attached. The method can be used to reformat selected nucleic acids in bulk (e.g., en masse or individually in parallel) or to reformat a library. For example, the plurality can include between $10^2$ and $10^8$ members, e.g., $10^2$-$10^5$, $10^3$-$10^5$, or 5-100. Each linkage of a first and second coding regions from the first nucleic acids can be represented among the second nucleic acids.

The modifying can include releasing, from first vectors, nucleic acid fragment that include the first and second coding regions and inserting the nucleic acid fragments into second vectors. The providing of first nucleic acids can include selecting members of a display library (e.g., a phage or yeast display library) for binding to a target.

The method can be used for expressing hetero-multimeric proteins, e.g., an antigen binding protein such as a Fab and/or a full length antibody, a T cell receptor, an MHC complex, and so forth.

Each of the first and second coding regions can be transcribed as a single transcript. In one embodiment, prior to the modifying, the nucleic acid cassettes include a promoter (e.g., a prokaryotic promoter) that regulates transcription of a single transcript that includes the first and second coding regions and is disposed upstream of the first coding region.

In one embodiment, the first expression system is prokaryotic and the second expression system is eukaryotic. For example, the second expression system is mammalian or fungal (e.g., yeast). In a particular example, the first expression system is prokaryotic (e.g., filamentous bacteriophage display) and the second expression system is mammalian. In another particular example, the first expression system is prokaryotic (e.g., filamentous bacteriophage display) and the second expression system is yeast.

In another embodiment, the first and second expression systems are eukaryotic. For example, the first expression system is yeast and the second expression system is mammalian.

In another embodiment, one of the expression systems can also be an in vitro translation system, e.g., an in vitro transcription-translation system or an eukaryotic in vitro translation system.

For each nucleic acid cassette of the plurality, the modifying can include inserting an internal ribosome entry site between the first and second coding regions. The modifying can also include removing a segment that includes the ribosomal binding site.

For each nucleic acid cassette of the plurality, the modifying can include linking a eukaryotic promoter to the cassette upstream of the first coding region such that the promoter regulates transcription of a transcript that includes the first coding region or the first and second coding region. In one example, for each nucleic acid cassette of the plurality, the modifying can further include removing the prokaryotic promoter (before or after the inserting). In another example, the prokaryotic promoter is retained, and, e.g., the eukaryotic promoter is linked upstream, downstream, or within the eukaryotic promoter.

The eukaryotic promoter may be functional, for example, in a mammalian, yeast, and/or plant cell, e.g., a human cell or a *Saccharomyces* cell.

For each nucleic acid cassette of the plurality, the modifying can include linking (e.g., inserting) a segment that includes a eukaryotic promoter between the first and second coding region. The eukaryotic promoter linked at this position is typically in addition to the eukaryotic promoter positioned upstream of the cassette. The segment can also include a leader, e.g., a leader that supports eukaryotic processing, e.g., a bifunctional leader or an exclusively eukaryotic leader.

For each nucleic acid cassette of the plurality, the modifying can include linking (e.g., inserting) a segment that includes an internal ribosome entry site (IRES) (e.g., a viral IRES) between the first and second coding regions.

Each of the segments can further include a signal sequence functional in a mammalian cell. The segment can further include a polyA addition regulatory sequence. In one embodiment, the segment includes both a eukaryotic polyA addition regulatory sequence and a eukaryotic promoter, e.g., a second eukaryotic promoter.

In a related embodiment, the segment includes a signal sequence functional in a mammalian cell.

In one embodiment, prior to or after the modifying, the second coding region of the nucleic acid cassette is in frame with a sequence encoding a first fusion polypeptide. For example, the first fusion polypeptide can include the polypeptide encoded by the first coding region and a bacteriophage coat protein or fragment thereof (e.g., a minor coat protein such as gene III or the gene III stump.).

In one example, for each nucleic acid cassette of the plurality, the modifying includes removing the sequence encoding the first fusion polypeptide, e.g., removing a sequence that encodes a bacteriophage coat protein or fragment thereof. The modifying can include attaching a different sequence encoding a second fusion polypeptide in frame to the second coding region. For example, the second fusion polypeptide may include an immunoglobulin heavy chain CH2 and CH3, Hinge-CH2-CH3, or other constant domains. The Fc region, which typically includes Hinge-CH2-CH3, can also include a modification that alters binding to an Fc receptor relative to another Fc receptor. The second polypeptide can further include other functional domains, e.g., a non-immunoglobulin functional domain, e.g., a localization signal, e.g., a cell attachment sequence. The second polypeptide can also independently include a polypeptide tag. In one embodiment, the first or second fusion includes a yeast extracellular domain or portion thereof.

The regions can further include a sequence encoding an immunoglobulin constant domain (e.g., CL or CH1).

In an embodiment, as a (direct or indirect) fusion of one of the immunoglobulin variable domains to the Fc domain includes a sequence modification that alters binding to an Fc receptor relative to another Fc receptor, e.g., the Fc domain is artificial and selectively binds to Fc receptors.

In one embodiment, for each nucleic acid cassette of the plurality, the modifying includes (in any order, or concurrently) a) replacing a nucleic acid segment between the first and second coding regions, b) replacing nucleic acid 5' of the coding strand of the first coding region and c) replacing nucleic acid 3' of the coding strand of the second coding region. For example, b) may be c) concurrent.

In one embodiment, the nucleic acid 5' of the coding strand is directly adjacent to the first coding region.

The modifying can include adding or removing one or more nucleotides but maintaining linkage between the first and second coding regions. With respect to the coding strand, the modifying can include: a) maintaining linkage between the 5' terminus of the first coding region and the 3' terminus of the second coding region, while disrupting the linkage between the 3' terminus of the first coding region and the 5' terminus of the second coding region; and b) maintaining linkage between the 5' terminus of the first coding region and the 3' terminus of the second coding region, while disrupting the linkage between the 3' terminus of the first coding region and the 5' terminus of the second coding region. The order can be reversed.

The nucleic acid 5' of the coding strand can include one or more of: an untranslated region, a ribosome binding site, a promoter, a segment encoding a leader sequence or portion thereof.

In another embodiment, the modifying includes only a single cloning step. The segment between the first and second coding regions includes a sequence encoding a signal sequence that is functional in two different expression systems. The signal sequence is fused to the second coding region. For example, the signal sequence is functional in both prokaryotic and eukaryotic cells, e.g., it includes VHA at the −3, −2, −1 positions, or it has at least 80%, 90%, 95%, or 100% identity to a natural signal sequence that is functional in both systems, e.g., a beta-lactamase signal sequence. A single cloning step can be used to alter the in-frame fusion of the second coding region and a third coding region (e.g., encoding an Fc domain or a gene III protein or fragment thereof).

The modifying can include annealing and extending a primer that includes a restriction site, e.g., that is endogenous or exogenous to the nucleic acid cassette prior to the modifying. For example, PCR can be used.

The modifying can include restricting the cassette using one or more of: ApaLI, AscI, MfeI, BstEII, NotI, XbaI, NcoI, PstI, NheI, SfiI and BssH2, e.g., including combinations such as AscI and MfeI; AscI and SfiI; ApaL1 and NotI; ApaL1 and NheI; or ApaL1 and BstEII.

The first and/or second polypeptide domain can include a leader sequence junction which is functional (e.g., cleavable) by both prokaryotic and eukaryotic cells. (The junction being only a region of the leader sequence that is directly N-terminal to the cleavage site, e.g., the 5, 4, or 3 amino acids N-terminal to the cleavage site.). For example, the leader sequence junction, e.g., includes at positions −3, −2, and −1: Val-His-Ala.

In one embodiment, the VL domain of the expressed heteromeric protein includes a naturally occurring N-terminus after leader sequence processing.

Each of the modified nucleic acid cassettes can include a chromatin control sequence (e.g., an insulator, a locus control region, or a chromatin opening element). The chromatin control sequence can be upstream of the first coding region, e.g., upstream of a promoter that is operably linked to the first coding region, or down stream of the second coding region, etc. The control sequence might even be inserted between the first and second coding regions.

In one aspect, the invention features a method that includes: (i) providing a nucleic acid cassette that includes a) a first coding region encoding a first polypeptide, b) a second coding region encoding a second polypeptide, and c) a ribosomal binding site disposed between the first and second coding regions for translation of the second polypeptide in a first expression system, wherein the first and second coding regions are in the same translational orientation, and the first and second coding regions encode at least segments of subunits of the hetero-multimeric protein; (ii) modifying the nucleic acid cassette so that it is functional in a second expression system, wherein the first and second region remain physically attached during the modifying; and (iii) expressing the hetero-multimeric protein from the modified nucleic acid cassette in the second expression system. The method can be used for expressing a hetero-multimeric protein, e.g., an antigen binding protein such as a Fab and/or a full length antibody, a T cell receptor, an MHC complex, and so forth.

The first and second coding regions can be transcribed as a single transcript. In one embodiment, prior to the modifying, the nucleic acid cassette includes a promoter (e.g., a prokaryotic promoter) that regulates transcription of a single transcript that includes the first and second coding regions and is disposed upstream of the first coding region.

In one embodiment, the first expression system is prokaryotic and the second expression system is eukaryotic. For example, the second expression system is mammalian or fungal (e.g., yeast). In a particular example, the first expression system is prokaryotic (e.g., filamentous bacteriophage display) and the second expression system is mammalian. In another particular example, the first expression system is prokaryotic (e.g., filamentous bacteriophage display) and the second expression system is yeast.

In another embodiment, the first and second expression systems are eukaryotic. For example, the first expression system is yeast and the second expression system is mammalian.

In another embodiment, one of the expression systems can also be an in vitro translation system, e.g., an in vitro transcription-translation system or an eukaryotic in vitro translation system.

The modifying can include inserting an internal ribosome entry site between the first and second coding regions. The modifying can also include removing a segment that includes the ribosomal binding site.

The modifying can include linking a eukaryotic promoter to the cassette upstream of the first coding region such that the promoter regulates transcription of a transcript that includes the first coding region or the first and second coding region. In one example, the modifying can further include removing the prokaryotic promoter (before or after the inserting). In another example, the prokaryotic promoter is retained, and, e.g., the eukaryotic promoter is linked upstream, downstream, or within the eukaryotic promoter.

The eukaryotic promoter may be functional, for example, in a mammalian, yeast, and/or plant cell, e.g., a human cell or a *Saccharomyces* cell.

The modifying can include linking (e.g., inserting) a segment that includes a eukaryotic promoter between the first and second coding region. The eukaryotic promoter linked at this position is typically in addition to the eukaryotic promoter positioned upstream of the cassette. The segment can also include a leader, e.g., a leader that supports eukaryotic processing, e.g., a bifunctional leader or an exclusively eukaryotic leader.

The modifying can include linking (e.g., inserting) a segment that includes an internal ribosome entry site (IRES) (e.g., a viral IRES) between the first and second coding regions.

The segment can further include a signal sequence functional in a mammalian cell. The segment can further include a polyA addition regulatory sequence. In one embodiment, the segment includes both a eukaryotic polyA addition regulatory sequence and a eukaryotic promoter, e.g., a second eukaryotic promoter.

In a related embodiment, the segment includes a signal sequence functional in a mammalian cell.

In one embodiment, prior to or after the modifying, the second coding region of the nucleic acid cassette is in frame with a sequence encoding a first fusion polypeptide. For example, the first fusion polypeptide can include the polypeptide encoded by the first coding region and a bacteriophage coat protein or fragment thereof (e.g., a minor coat protein such as gene III or the gene III stump.).

In one example, the modifying includes removing the sequence encoding the first fusion polypeptide, e.g., removing a sequence that encodes a bacteriophage coat protein or fragment thereof. The modifying can include attaching a different sequence encoding a second fusion polypeptide in frame to the second coding region. For example, the second fusion polypeptide may include an immunoglobulin heavy chain CH2 and CH3, Hinge-CH2-CH3, or other constant domains. The Fc region, which typically includes Hinge-CH2-CH3 can also include a modification that alters binding to an Fc receptor relative to another Fc receptor. The second polypeptide can further include other functional domains, e.g., a non-immunoglobulin functional domain, e.g., a localization signal, e.g., a cell attachment sequence. The second polypeptide can also independently include a polypeptide tag. In one embodiment, the first or second fusion includes a yeast extracellular domain or portion thereof.

In one embodiment, the first and second coding regions encode immunoglobulin variable domain, e.g., respectively, a VH and VL or VL and VH domains. The regions can further include a sequence encoding an immunoglobulin constant domain (e.g., CL or CH1).

In an embodiment, as a (direct or indirect) fusion of one of the immunoglobulin variable domains to the Fc domain includes a sequence modification that alters binding to an Fc receptor relative to another Fc receptor, e.g., the Fc domain is artificial and selectively binds to Fc receptors.

In one embodiment, the modifying includes (in any order, or concurrently) a) replacing a nucleic acid segment between the first and second coding regions, b) replacing nucleic acid 5' of the coding strand of the first coding region and c) replacing nucleic acid 3' of the coding strand of the second coding region. For example, b) may be c) concurrent.

In one embodiment, the nucleic acid 5' of the coding strand is directly adjacent to the first coding region.

The modifying can include adding or removing one or more nucleotides but maintaining linkage between the first and second coding regions. With respect to the coding strand, the modifying can include: a) maintaining linkage between the 5' terminus of the first coding region and the 3' terminus of the second coding region, while disrupting the linkage between the 3' terminus of the first coding region and the 5' terminus of the second coding region; and b) maintaining linkage between the 5' terminus of the first coding region and the 3' terminus of the second coding region, while disrupting the linkage between the 3' terminus of the first coding region and the 5' terminus of the second coding region. The order can be reversed.

The nucleic acid 5' of the coding strand can include one or more of: an untranslated region, a ribosome binding site, a promoter, a segment encoding a leader sequence or portion thereof.

In another embodiment, the modifying includes only a single cloning step. The segment between the first and second coding regions includes a sequence encoding a signal sequence that is functional in two different expression systems. The signal sequence is fused to the second coding region. For example, the signal sequence is functional in both prokaryotic and eukaryotic cells, e.g., it includes VHA at the −3, −2, −1 positions, or it has at least 80%, 90%, 95%, or 100% identity to a natural signal sequence that is functional in both systems, e.g., a beta-lactamase signal sequence. A single cloning step can be used to alter the in-frame fusion of the second coding region and a third coding region (e.g., encoding an Fc domain or a gene III protein or fragment thereof).

The modifying can include annealing and extending a primer that includes a restriction site, e.g., that is endogenous or exogenous to the nucleic acid cassette prior to the modifying. For example, PCR can be used.

The modifying can include restricting the cassette using one or more of: ApaLI, AscI, MfeI, BstEII, NotI, XbaI, NcoI, PstI, NheI, SfiI and BssH2, e.g., including combinations such as AscI and MfeI; AscI and SfiI; ApaL1 and NotI; ApaL1 and NheI; or ApaL1 and BstEII.

The first and/or second polypeptide domain can include a leader sequence junction which is functional (e.g., cleavable) by both prokaryotic and eukaryotic cells. (The junction being only a region of the leader sequence that is directly N-terminal to the cleavage site, e.g., the 5, 4, or 3 amino acids N-terminal to the cleavage site.). For example, the leader sequence junction, e.g., includes at positions −3, −2, and −1: Val-His-Ala.

In one embodiment, the VL domain of the expressed heteromeric protein includes a naturally occurring N-terminus after leader sequence processing.

The modified nucleic acid cassette can include a chromatin control sequence (e.g., an insulator, a locus control region, or a chromatin opening element). The chromatin control sequence can be upstream of the first coding region, e.g., upstream of a promoter that is operably linked to the first coding region, or down stream of the second coding region, etc. The control sequence might even be inserted between the first and second coding regions.

In another aspect, the invention features a method that includes: (i) providing a plurality of nucleic acid cassettes, each nucleic acid cassette that includes a) a first coding region encoding a first polypeptide, b) a second coding region encoding a second polypeptide, and c) a ribosomal binding site disposed between the first and second coding regions for translation of the second polypeptide in a first expression system, wherein the first and second coding regions are in the same translational orientation, and the first and second coding regions can be transcribed as a single transcript; and the first and second coding regions encode at least segments of subunits of a hetero-multimeric protein, and (ii) modifying each nucleic acid cassette of the plurality to produce second nucleic acids, each second nucleic acid being functional in a second expression system, wherein the first and second coding regions remain attached. The method can be used to reformat selected nucleic acids in bulk (e.g., en masse or individually in parallel) or to reformat a library. For example, the plurality can include between $10^2$ and $10^8$ members, e.g., $10^2$-$10^5$, $10^3$-$10^5$, or 5-100. Each linkage of a first and second coding regions from the first nucleic acids can be represented among the second nucleic acids.

The modifying can include releasing, from first vectors, nucleic acid fragment that include the first and second coding regions and inserting the nucleic acid fragments into second vectors. The providing of first nucleic acids can include selecting members of a display library (e.g., a phage or yeast display library) for binding to a target.

The method can be used for expressing hetero-multimeric proteins, e.g., an antigen binding protein such as a Fab and/or a full length antibody, a T cell receptor, an MHC complex, and so forth.

Each of the first and second coding regions can be transcribed as a single transcript. In one embodiment, prior to the modifying, the nucleic acid cassettes include a promoter (e.g., a prokaryotic promoter) that regulates transcription of a single transcript that includes the first and second coding regions and is disposed upstream of the first coding region.

In one embodiment, the first expression system is prokaryotic and the second expression system is eukaryotic. For example, the second expression system is mammalian or fungal (e.g., yeast). In a particular example, the first expression system is prokaryotic (e.g., filamentous bacteriophage display) and the second expression system is mammalian. In another particular example, the first expression system is prokaryotic (e.g., filamentous bacteriophage display) and the second expression system is yeast.

In another embodiment, the first and second expression systems are eukaryotic. For example, the first expression system is yeast and the second expression system is mammalian.

In another embodiment, one of the expression systems can also be an in vitro translation system, e.g., an in vitro transcription-translation system or an eukaryotic in vitro translation system.

For each nucleic acid cassette of the plurality, the modifying can include inserting an internal ribosome entry site between the first and second coding regions. The modifying can also include removing a segment that includes the ribosomal binding site.

For each nucleic acid cassette of the plurality, the modifying can include linking a eukaryotic promoter to the cassette upstream of the first coding region such that the promoter regulates transcription of a transcript that includes the first coding region or the first and second coding region. In one example, for each nucleic acid cassette of the plurality, the modifying can further include removing the prokaryotic promoter (before or after the inserting). In another example, the prokaryotic promoter is retained, and, e.g., the eukaryotic promoter is linked upstream, downstream, or within the eukaryotic promoter.

The eukaryotic promoter may be functional, for example, in a mammalian, yeast, and/or plant cell, e.g., a human cell or a *Saccharomyces* cell.

For each nucleic acid cassette of the plurality, the modifying can include linking (e.g., inserting) a segment that includes a eukaryotic promoter between the first and second coding region. The eukaryotic promoter linked at this position is typically in addition to the eukaryotic promoter positioned upstream of the cassette. The segment can also include a leader, e.g., a leader that supports eukaryotic processing, e.g., a bifunctional leader or an exclusively eukaryotic leader.

For each nucleic acid cassette of the plurality, the modifying can include linking (e.g., inserting) a segment that includes an internal ribosome entry site (IRES) (e.g., a viral IRES) between the first and second coding regions.

Each of the segments can further include a signal sequence functional in a mammalian cell. The segment can further include a polyA addition regulatory sequence. In one embodiment, the segment includes both a eukaryotic polyA addition regulatory sequence and a eukaryotic promoter, e.g., a second eukaryotic promoter.

In a related embodiment, the segment includes a signal sequence functional in a mammalian cell.

In one embodiment, prior to or after the modifying, the second coding region of the nucleic acid cassette is in frame with a sequence encoding a first fusion polypeptide. For example, the first fusion polypeptide can include the polypeptide encoded by the first coding region and a bacteriophage coat protein or fragment thereof (e.g., a minor coat protein such as gene III or the gene III stump.).

In one example, for each nucleic acid cassette of the plurality, the modifying includes removing the sequence encoding the first fusion polypeptide, e.g., removing a sequence that encodes a bacteriophage coat protein or fragment thereof. The modifying can include attaching a different sequence encoding a second fusion polypeptide in frame to the second coding region. For example, the second fusion polypeptide may include an immunoglobulin heavy chain CH2 and CH3, Hinge-CH2-CH3, or other constant domains. The Fc region, which typically includes Hinge-CH2-CH3 can also include a modification that alters binding to an Fc receptor relative to another Fc receptor. The second polypeptide can further include other functional domains, e.g., a non-immunoglobulin functional domain, e.g., a localization signal, e.g., a cell attachment sequence. The second polypeptide can also independently include a polypeptide tag. In one embodiment, the first or second fusion includes a yeast extracellular domain or portion thereof.

In one embodiment, the first and second coding regions encode immunoglobulin variable domain, e.g., respectively, a VH and VL or VL and VH domains. The regions can further include a sequence encoding an immunoglobulin constant domain (e.g., CL or CH1).

In an embodiment, as a (direct or indirect) fusion of one of the immunoglobulin variable domains to the Fc domain includes a sequence modification that alters binding to an Fc receptor relative to another Fc receptor, e.g., the Fc domain is artificial and selectively binds to Fc receptors.

In one embodiment, for each nucleic acid cassette of the plurality, the modifying includes (in any order, or concurrently) a) replacing a nucleic acid segment between the first and second coding regions, b) replacing nucleic acid 5' of the coding strand of the first coding region and c) replacing nucleic acid 3' of the coding strand of the second coding region. For example, b) may be c) concurrent.

In one embodiment, the nucleic acid 5' of the coding strand is directly adjacent to the first coding region.

The modifying can include adding or removing one or more nucleotides but maintaining linkage between the first and second coding regions. With respect to the coding strand, the modifying can include: a) maintaining linkage between the 5' terminus of the first coding region and the 3' terminus of the second coding region, while disrupting the linkage between the 3' terminus of the first coding region and the 5' terminus of the second coding region; and b) maintaining linkage between the 5' terminus of the first coding region and the 3' terminus of the second coding region, while disrupting the linkage between the 3' terminus of the first coding region and the 5' terminus of the second coding region. The order can be reversed.

The nucleic acid 5' of the coding strand can include one or more of: an untranslated region, a ribosome binding site, a promoter, a segment encoding a leader sequence or portion thereof.

In another embodiment, the modifying includes only a single cloning step. The segment between the first and second coding regions includes a sequence encoding a signal sequence that is functional in two different expression systems. The signal sequence is fused to the second coding region. For example, the signal sequence is functional in both prokaryotic and eukaryotic cells, e.g., it includes VHA at the −3, −2, −1 positions, or it has at least 80%, 90%, 95%, or 100% identity to a natural signal sequence that is functional in both systems, e.g., a beta-lactamase signal sequence. A single cloning step can be used to alter the in-frame fusion of the second coding region and a third coding region (e.g., encoding an Fc domain or a gene III protein or fragment thereof).

The modifying can include annealing and extending a primer that includes a restriction site, e.g., that is endogenous or exogenous to the nucleic acid cassette prior to the modifying. For example, PCR can be used.

The modifying can include restricting the cassette using one or more of: ApaLI, AscI, MfeI, BstEII, NotI, XbaI, NcoI, PstI, NheI, SfiI and BssH2, e.g., including combinations such as AscI and MfeI; AscI and SfiI; ApaL1 and NotI; ApaL1 and NheI; or ApaL1 and BstEII.

The first and/or second polypeptide domain can include a leader sequence junction which is functional (e.g., cleavable) by both prokaryotic and eukaryotic cells. (The junction being only a region of the leader sequence that is directly N-terminal to the cleavage site, e.g., the 5, 4, or 3 amino acids N-terminal to the cleavage site.). For example, the leader sequence junction, e.g., includes at positions −3, −2, and −1: Val-His-Ala.

In one embodiment, the VL domain of the expressed heteromeric protein includes a naturally occurring N-terminus after leader sequence processing.

Each of the modified nucleic acid cassettes can include a chromatin control sequence (e.g., an insulator, a locus control region, or a chromatin opening element). The chromatin control sequence can be upstream of the first coding region, e.g., upstream of a promoter that is operably linked to the first coding region, or down stream of the second coding region, etc. The control sequence might even be inserted between the first and second coding regions.

The invention also features a method of expressing a hetero-multimeric protein. The method includes: (i) providing a first nucleic acid including a) a first coding region encoding a first polypeptide domain, b) a second coding region encoding a second polypeptide domain, and c) a sequence encoding a peptide linker that links the first polypeptide domain and the second polypeptide domain within a single polypeptide chain, wherein the first and second coding regions are in the same translational orientation, and the first and second coding regions encode subunits of an antigen binding protein, and (ii) modifying the first nucleic acid so that the first and second polypeptide domains can be translated as separate polypeptides in such manner that the DNAs encoding the first and second polypeptide domains maintain a physical link throughout the modification procedure. The first and second polypeptide domains can encode an immunoglobulin variable domain, e.g., VL and VH. The first nucleic acid can encode a scFV. The segment between the first and second coding regions can include a peptide linker, e.g., a linker compatible with scFv function. After modification, the sequence can encode, e.g., a Fab or full-chain antibody. The modifying can also be reversed, e.g., to move from a multi-chain format to a single-chain format.

In still another aspect, the invention features a method that includes: providing a first plurality of different nucleic acids, each encoding a hetero-oligomeric candidate ligand; selecting a subset of the first plurality by contacting to a target; reformatting each nucleic acid of the subset for mammalian cell expression, such that each nucleic acid encodes a hetero-oligomeric protein that includes a first functional domain of one subunit of the candidate ligand, a second functional domain of another subunit of the candidate ligand and an effector domain not encoded by the nucleic acids of the first plurality; introducing members of the subset into a mammalian cell to form a plurality of expression cells that can produce the protein that includes the functional domain and the effector domain; and screening the expression cells to identify cells that produce at least a threshold amount of a ligand-effector domain fusion protein.

In one embodiment, the introducing is effected separately for each nucleic acid of the subset or of the first plurality. In another embodiment, the introducing includes preparing a mixture that includes nucleic acid for a plurality of members of the subset or of the first plurality and contacting mammalian cells with the mixture under conditions in which the nucleic acids are introduced into the cells.

In one embodiment, the screening includes FACS. In another embodiment, the screening includes magnetic particle-based separation. The screening can include culturing the cells in a low permeability medium. The screening can further include attaching a probe to surfaces of the cells, the probe having a binding domain that recognizes a constant region of the fusion proteins, and detecting the amount of fusion protein retained by the surface-bound probe. For example, the constant region can includes a portion of the heavy chain, the light chain, or combinations thereof. The probe, which includes a protein (e.g., an antibody) that recognizes the constant region of the expressed immunoglobulin (e.g., an antibody that recognizes human immunoglobulin) may be attached by a linkage that includes a chemical tag, e.g., biotin. The probe can be specific for one of the antibody chains, but not the other (e.g., heavy, but not light; or light but not heavy. The detecting can includes detecting binding of a label to the other antibody chain (i.e., the one not retained by the surface-bound probe). The detecting can be specific for whole antibodies.

In another embodiment, the cells express a heterologous protein that is attached to the cell surface and recognizes a constant region of the fusion proteins. The heterologous protein can be, e.g. an antibody specific for a chain of a human antibody or an Fc receptor, e.g., a human Fc receptor or a non-human Fc receptor with specificity for human Fc regions. The effector domain can include CH2 and CH3, e.g., Hinge-CH2 and CH3, e.g., an Fc region of a human isotype (e.g., IgG1, etc. isotypes). In one embodiment, each fusion protein of the plurality of fusion proteins is glycosylated on Asn 297. In a particular embodiment, each fusion protein can elicit ADCC or CDC.

Each candidate ligand can includes a plurality of polypeptide chains, e.g., it includes a Fab structure.

The reformatting is en masse. For example, the reformatting includes at least a reaction of multiple nucleic acids in the same mixture. The reformatting maintains linkage between the polypeptide chains for each candidate ligand. The introducing and expressing can include transient expression and/or generating a stable cell line.

The expressing can include producing at least 5, 10, 20, 40 mg of each fusion protein. At least one of the fusion protein can be expressed in a hollow fiber bioreactor, or a subject organism. In the latter case, the method can include monitoring the subject organism for a clinical indication, e.g., the subject can be a normal, diseased, or disease-predisposed individual.

In an embodiment, a mixture of nucleic acids from the subset are introduced into the mammalian cells together, e.g., a mixture of nucleic acids is transfected into a population of cells, e.g., under controlled conditions, e.g., under low nucleic acid concentrations. The method can include, after the screening, determining which nucleic acid of the mixture was introduced into one or more of the cells.

In an embodiment, the method includes assaying one or more proteins of the plurality for a cell-mediated activity, a biochemical property, a structural property, or a physiological property (e.g., bioavailability).

The method can further include assaying one or more proteins of the plurality in a subject organism.

The method can also further include selecting one or more proteins that meet a criterion based on the assaying. The proteins can be mutagenized, e.g., individually or as an ensemble (e.g., using DNA shuffling or chain shuffling).

In some implementations, the selected proteins are mutagenized en masse.

The expressing can include identifying cells that have at least a threshold level of fusion protein expression. The identifying can include FACS, magnetic particle-based sorting, or an automated selection.

In one embodiment the identifying includes an automated screening.

In another aspect, the invention features a method of reformatting hetero-oligomeric receptors for production in mammalian cells. The method (which can be, e.g., a machine-based method) includes: providing a plurality of nucleic acid library members; determining an assessment for each library member with respect to a property; storing information about the assessments of the library members in a database; filtering the information to identify a subset of the library members; and reformatting each member of the subset for expression in a mammalian cell by a method that comprises disposing nucleic acid for each member of the selected subset into a single container. Each of the nucleic acid library members of the plurality, for example, encodes component polypeptides of a hetero-oligomeric receptor, e.g., the immunoglobulin heavy chain and immunoglobulin light chain.

In one embodiment, the library members are formatted, e.g., for yeast display, phage display, or bacterial expression, prior to the reformatting.

The determining can include contacting a protein array with a target, a protein corresponding to each library member being present at an address of the array.

The invention also features a machine-accessible medium that includes, encoded thereon or therein data representing (a) identifiers for library members that each encode a polypeptide, (b) results of a first functional assays for at least some of the library members; (c) results of a second functional assays for at least some of the library members; and associations that relate the results of the first and/or second functional assays and the library member identifiers, wherein the second functional assay depends on an activity that is dependent on a given effector domain (e.g., an Fc domain), and the first functional assay depends on an activity that is independent of the given effector domain (e.g., the Fc domain). For example, the second functional assay may be a cell based assay or an organism-based assay. One cell-based assay is cell-mediated cytotoxicity.

The methods described herein can include accessing the medium and filtering the data for a criterion, e.g., and reformatting one or more entities based on the filtering.

The invention also features a nucleic acid that includes: a first promoter, a first signal sequence, a first coding region, an intervening segment, a second coding region, and a third coding region, fused in frame to the second coding region (the second and third coding regions can be heterologous or not). In one embodiment, the intervening segment includes, for example, a eukaryotic promoter, a prokaryotic promoter, and a leader sequence that is cleaved in eukaryotic and prokaryotic cells. In another embodiment, intervening segment further includes an IRES, e.g., upstream and a leader sequence that is cleaved in eukaryotic and prokaryotic cells. See, e.g., upper and lower panels of FIGS. 9 and 10.

The "effector domain" can be any functional domain that can produce a signal or effect. Non-limiting examples of effector domains include an immunological effector domain, a labelling domain, an enzymatic domain, or a non-immunoglobulin cell-binding domain. One exemplary class of effector domains includes effector domains that are functional in the extracellular environment. Such domains differ, for example, from a transcriptional activation domain which function within the nucleus of a eukaryotic cell.

A "localization signal" is a polypeptide sequence that determines the subcellular localization of polypeptide or protein. The subcellular localization may be: cytoplasmic, nuclear, nuclear envelope, transmembrane, plasma membrane, plasma membrane outer leaflet, endoplasmic reticulum, Golgi, lysosomal, receptor-coated pits, and so forth. For example, the peptide sequence KDEL (SEQ ID NO:32) is an endoplasmic reticulum localization signal and when grafted onto a heterologous protein results in its endoplasmic reticulum localization. An antigen binding protein can be localized within a cell, e.g., as described by Marasco (2001) *Curr Top Microbiol Immunol.* 260:247-70.

An exemplary immunological effector domain includes the Fc domain. The Fc domain binds to host tissues or factors, including various cells of the immune system (e.g., effector cells) and the first component (C1q) of the classical complement system. The effector domain can include an Fc domain or component thereof, e.g., CH2, CH3, CH4, CH2-CH3, or CH2-CH3-CH4. The effector domain can, in some implementations, include the hinge region, i.e., the region between CH1 and CH2. A typical Fc region includes Hinge, CH2 and CH3 and forms a dimeric structure. The dimer can optionally include a disulfide bridge or chemical crosslink.

The Fc domain can also be of any isotype (for human Fc's, e.g., IgM, IgG1, IgG2, IgG3, or IgG4). In a preferred embodiment, the Fc effector domain is glycosylated, e.g., at the asparagine corresponding to asparagine 297 of IgG (Kabat numbering). Preferably, the Fc domain can bind C1q, e.g., if aggregated, and can bind an Fc receptor, e.g., FCγR1, FCγRIIA, FCγRIIB, FCγRIIIA, or FCγRIIIB. In a much-preferred embodiment, when aggregated, the effector domain elicits a response, e.g., a cytotoxic response, from leukocytes, e.g., NK cells.

Other effector domains include domains that can produce signals, e.g., green fluorescent protein and derivatives thereof, luciferase, alkaline phosphatase, and horseradish peroxidase. In a preferred embodiment, the effector domain comprises a cytotoxin or cytotoxin component, e.g., a chain of diphtheria toxin, ricin, or cholera toxin.

As used herein, "specific binding" refers to the property of a protein, e.g., a target or antigen-binding protein or domain: (1) to bind to a target with an affinity of at least $1\times10^7$ M$^{-1}$, and (2) to preferentially bind to the target with an affinity that is at least two-fold greater than its affinity for binding to a non-specific target (e.g., BSA or casein)

As used herein, the term "antibody" refers to a protein comprising at least one, and preferably two, heavy (H) chain variable regions (abbreviated herein as VH), and at least one and preferably two light (L) chain variable regions (abbreviated herein as VL). Thus, the term encompasses fragments of full-length antibodies (e.g., Fabs) which have functional antigen binding properties (see also below), and include one heavy chain variable region and one light chain variable region.

The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The term "full-length antibody" includes intact immunoglobulins of types IgA, IgG, IgE, IgD, IgM (as well as subtypes thereof), wherein the light chains of the immunoglobulin may be of types kappa or lambda. As used herein, "isotype" refers to the antibody class (e.g., IgM or IgG1) that is encoded by heavy chain constant region genes.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the N-terminus (about 110 amino acids) and a kappa or lambda constant region gene at the C-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

An "immunoglobulin domain" refers to a domain from the variable or constant domain of immunoglobulin molecules. The term "immunoglobulin superfamily domain" is distinguished from "immunoglobulin domain." An "immunoglobulin superfamily domain" refers to a domain that has a three-dimensional structure related to an immunoglobulin domain, but is from a non-immunoglobulin molecule. Immunoglobulin domains and immunoglobulin superfamily domains typically contains two β-sheets formed of about seven β-strands, and a conserved disulphide bond (see, e.g., Williams and Barclay 1988 *Ann. Rev Immunol.* 6:381-405). Proteins that include immunoglobulin superfamily domains include CD4, platelet derived growth factor receptor (PDGFR), and intercellular adhesion molecule (ICAM). Immunoglobulin superfamily domains from these proteins, for example, are consider non-immunoglobulin target-binding domains if they function to bind a specific target. The term "antigen-binding fragment" of an antibody (or "antigen binding protein"), as used herein, refers to one or more fragments of a full-length antibody that retain the ability to specifically bind to a target (e.g., an antigen such a polypeptide or a hapten). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

The "natural N-terminus" of an antibody refers to, for a particular isotype and species, the naturally occurring N-terminal sequence after processing of the naturally occurring signal sequence (regardless of signal sequence actually used). For example, the natural N-terminus of a κ light chain is DIQ.

(Middle) Fab cassette of the display vector inserted in mammalian expression vector pBRV as ApaL1/BstE2 fragment. 5' of LC: HCMV immediate early promoter and eukaryotic leader sequence, 3' of VH: constant region of human IgG1 heavy chain.

(Bottom) Prokaryotic rbs and leader are removed and eukaryotic "internal ribosome entry site (IRES) and eukaryotic leader sequence are inserted via Asc1 and Mfe1 restriction sites.

Figure 3:
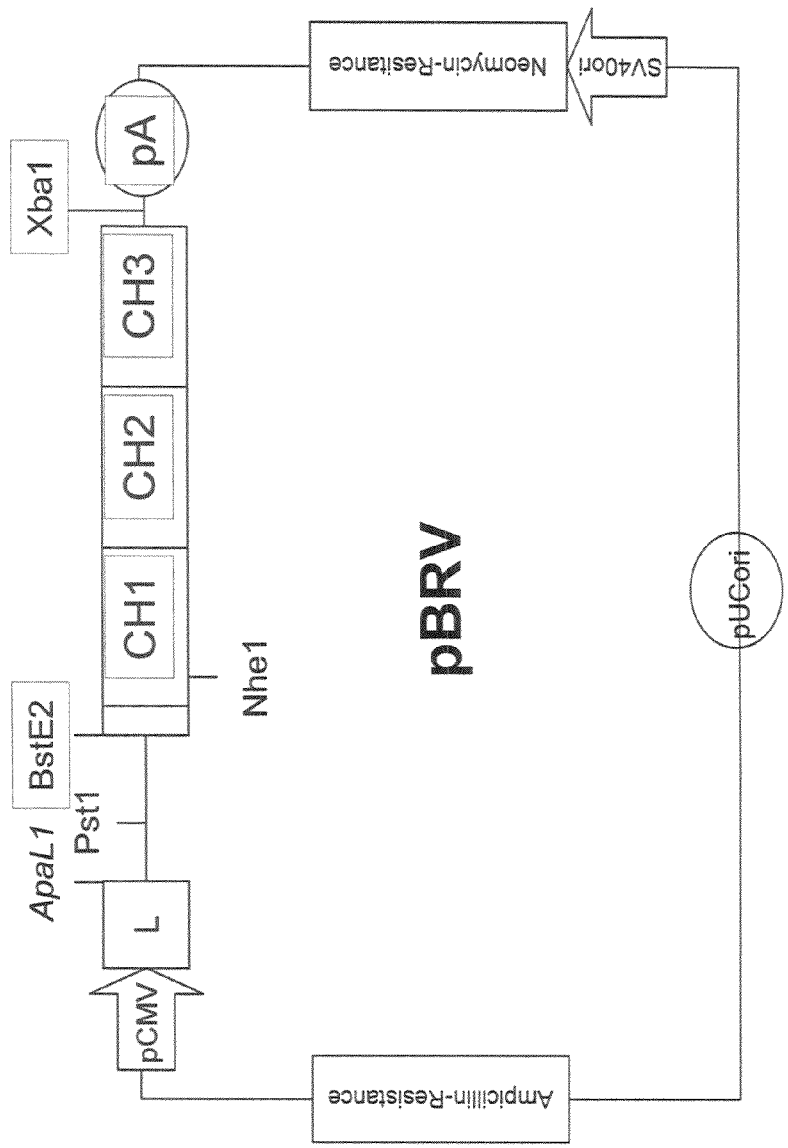

FIG. 3 is a schematic of pBRV. The plasmid includes an antibody expression cassette, and also the neomycin resistance gene as a selectable marker for generation of stable cell lines; the SV40 origin of replication. pRRV is similar to pBRV, except for the precise position of the ApaL1 site in the geneIII leader adjacent to VL (after Fab insertion).

Figure 4:
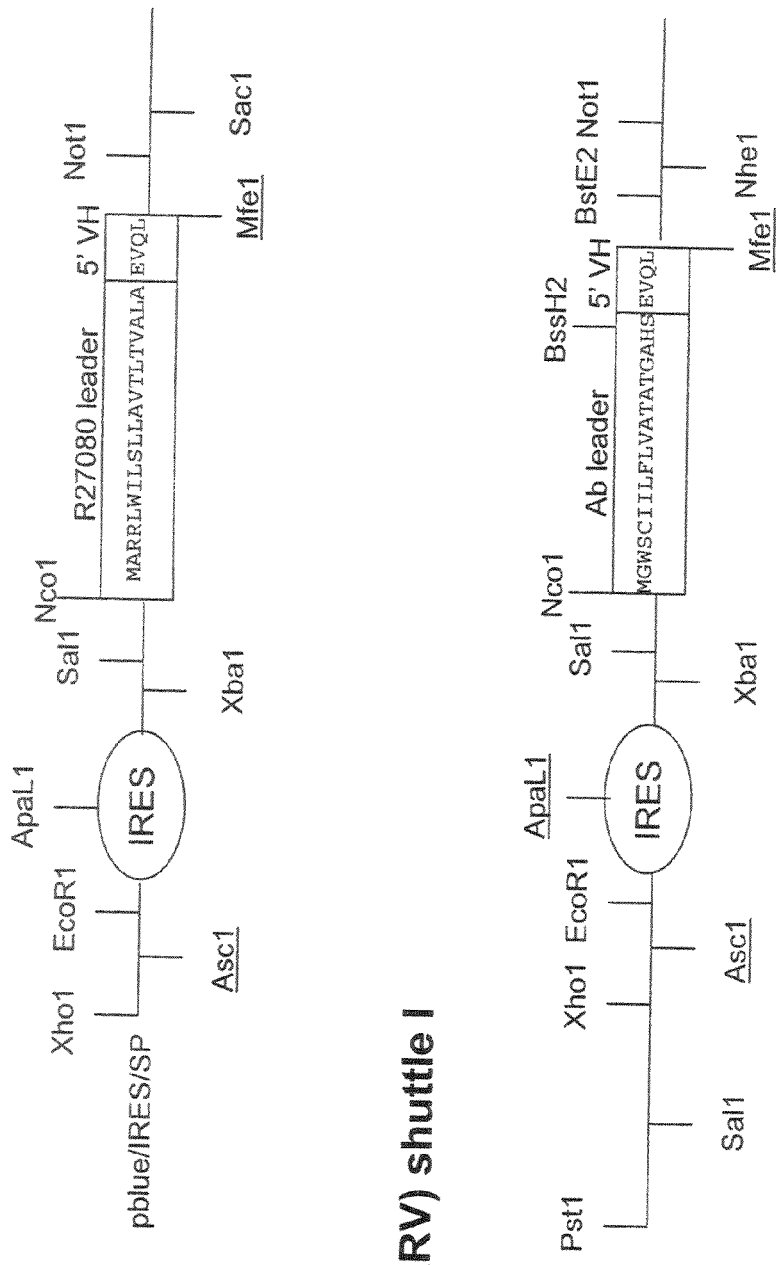

FIG. 4 is a schematic of regulatory elements (IRES+leader sequence) located between the first and second coding regions in pblue and pRRV (shuttle vector). In pblue/IRES/SP, the R27080 leader is SEQ ID NO:1, and the four 5' VH amino acids are SEQ ID NO:3. In (pRRV) shuttle I, the Ab leader is SEQ ID NO:2, and the four 5' VH amino acids are SEQ ID NO:3.

Figure 5:
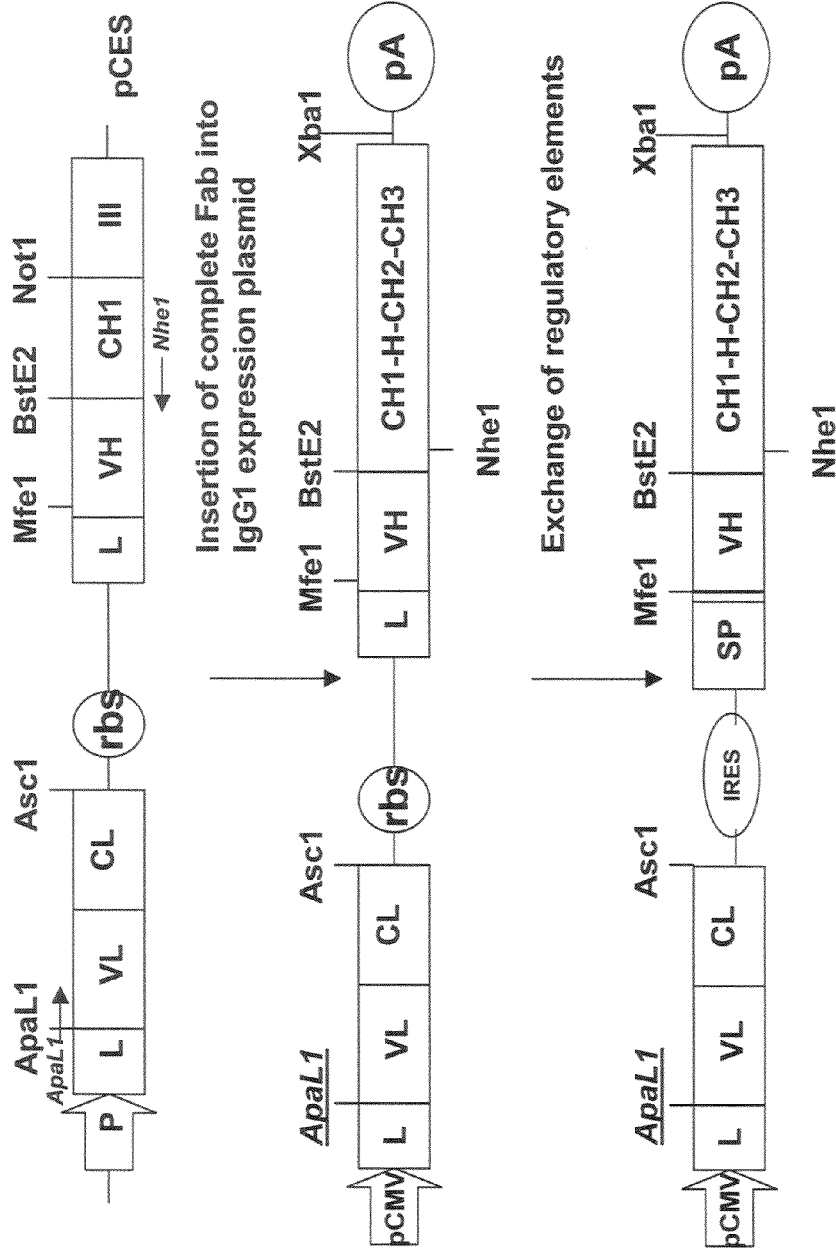

FIG. 5 is a reformatting scheme for transfer of individual Fabs to pRRV.

(Top) Organization of display vector: prokaryotic promoter (LacZ), M13 geneIII leader, complete LC (ApaL1/Asc1 fragment), bacterial ribosome binding site (rbs), PelB leader, VH (inserted as SfiI/BstE2 fragment) CH1 fused to M13 geneIII.

PCR primer binding sites are shown as arrows. The forward primer anneals to the 5' end of the Vgene. The reverse primer binds in CH1. The complete Fab insert is amplified by PCR.

(Middle) Fab cassette of the display vector inserted in mammalian expression vector pBRV as ApaL1/BstE2 fragment. 5' of LC: HCMV immediate early promoter and eukaryotic leader sequence, 3' of VH: constant region of human IgG1 heavy chain.

(Bottom) Prokaryotic rbs and leader are exchanged against eukaryotic "internal ribosome entry site (IRES) and eukaryotic leader sequence via Asc1 and Mfe1.

Figure 6:
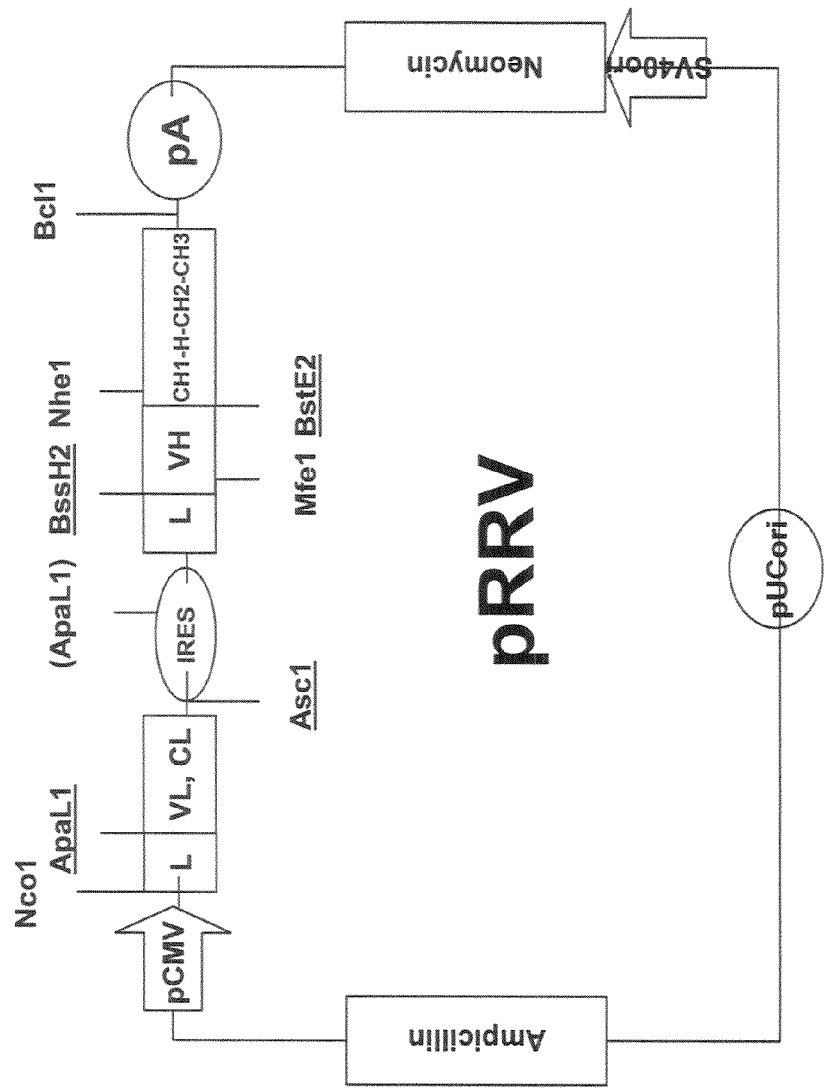
Figure 7:
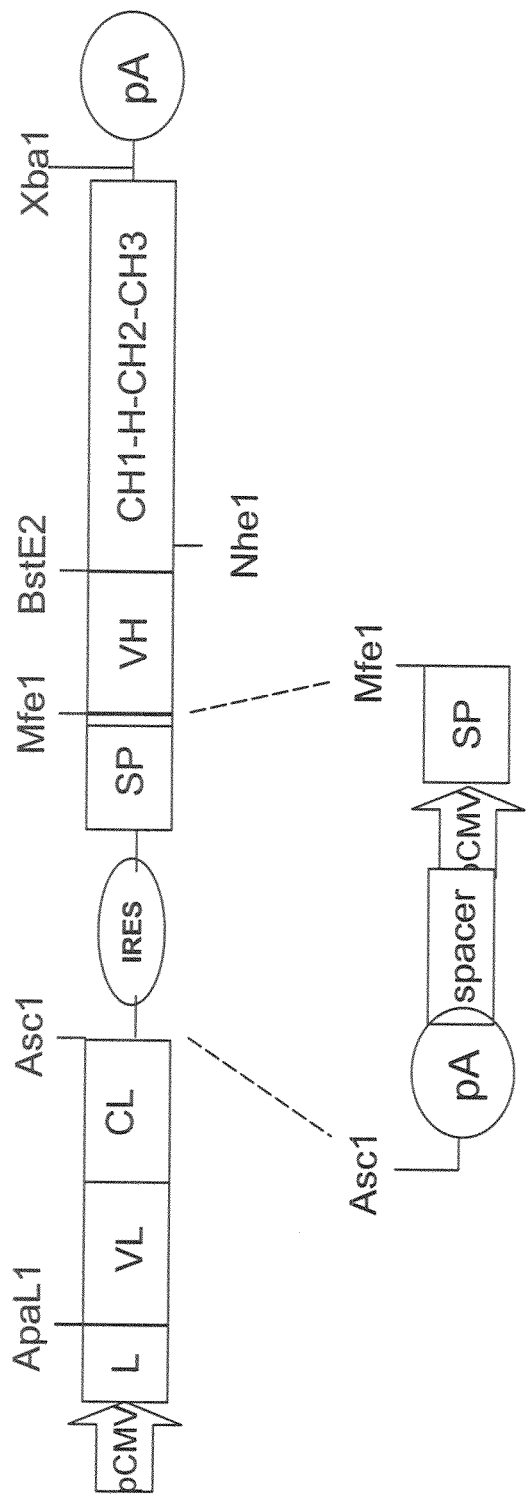

FIG. 6 is a schematic of pRRV, including a complete antibody expression cassette, after reformatting FIG. 7 is a schematic of a regulatory element consisting of polyA site, a second eukaryotic promoter and a leader sequence functional in mammalian cells.

This set-up, introduction of a second promoter to drive HC expression, can be used instead of IRES.

Figure 8:
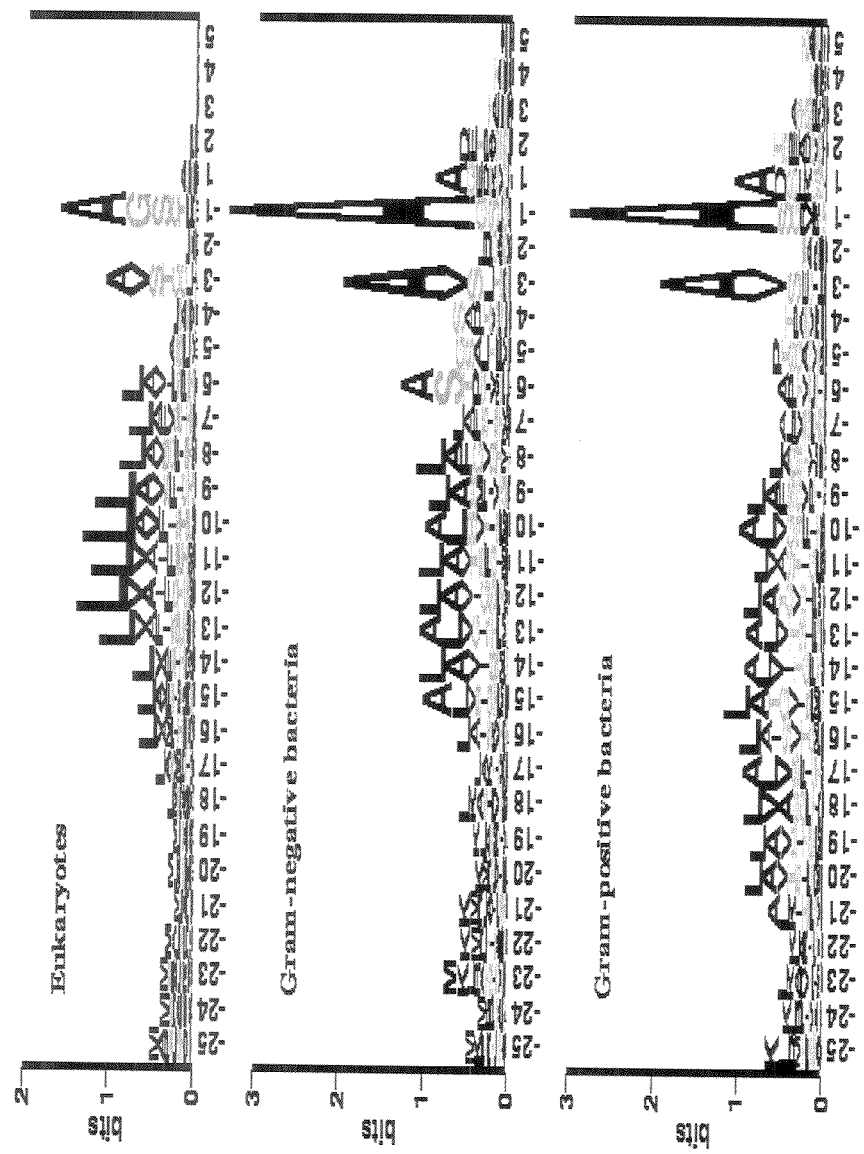

FIG. 8 depicts leader sequence preferences.

Figure 9:
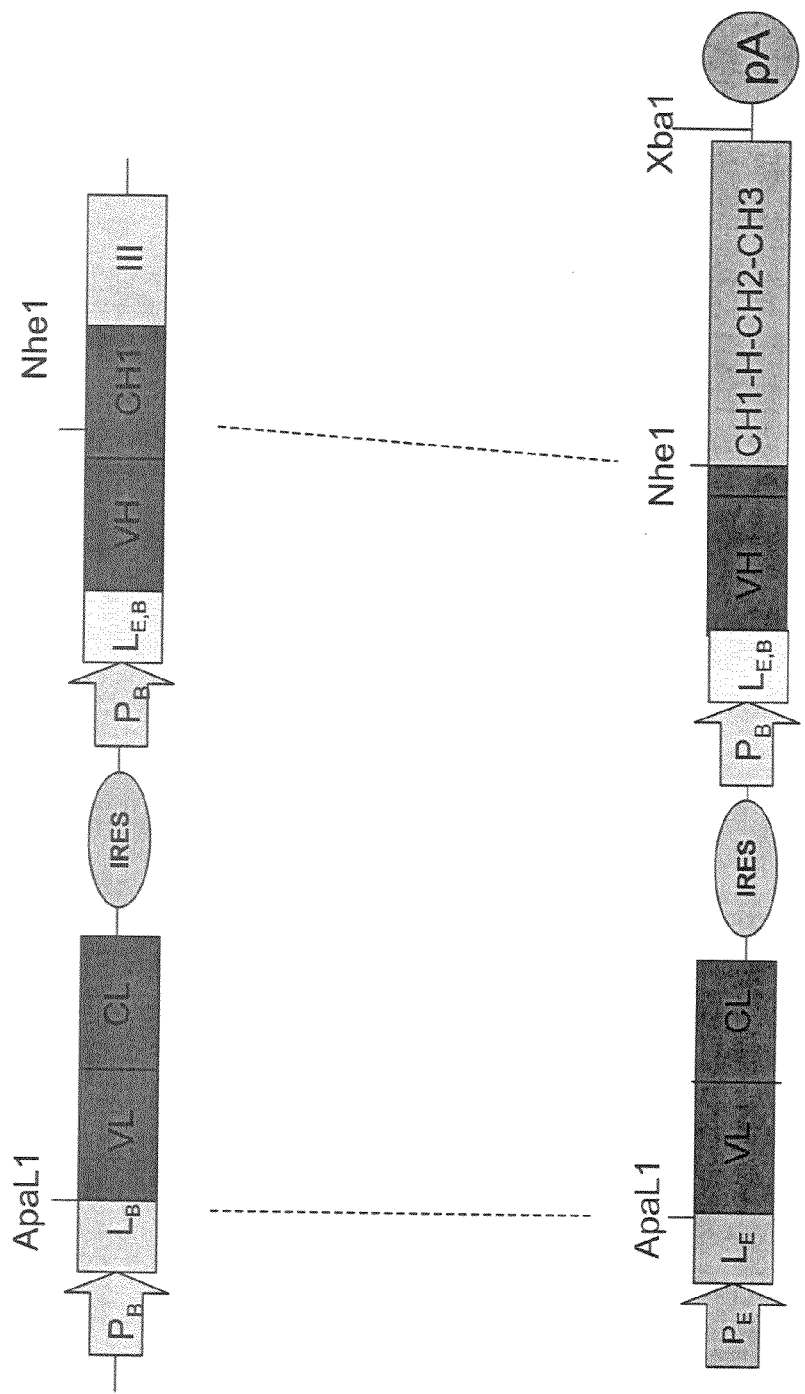

FIG. 9 is a schematic of an exemplary integrated expression vector. A Fab expression cassette in the vector can be shuttled between a prokaryotic Fab display system (top) and a mammalian IgG expression system (bottom). The Fab cassette is transferred as an ApaL1/Nhe1 fragment, in a single cloning step. Since, for the heavy chain, a leader is used that is functional in bacteria and mammalian cells, and regulatory elements for pro- and eukaryotic expression are supplied, no further (i.e. second) cloning steps are required.

(Top)—Fab display construct: a prokaryotic bicistronic expression cassette consisting of the following elements: $P_B$, prokaryotic promoter (e.g. LacZ); $L_B$, bacterial leader; VL-CL, light chain portion of Fab; IRES, internal ribosome entry; $P_B$, prokaryotic promoter; $L_{E,B}$, bifunctional leader (functional in bacteria and in mammalian cells); VH-CH1, heavy chain portion of Fab; III, gene III of a filamentous phage.

(Bottom)—IgG expression cassette: $P_E$, eukaryotic promoter; $L_E$, eukaryotic leader; VL-CL, light chain of antibody; IRES, internal ribosome entry site; $P_B$, prokaryotic promoter; $L_{E,B}$, bifunctional leader (functional in bacteria and in mammalian cells); VH-CH1-H-CH2-CH3, antibody heavy chain regions; pA, poly-adenylation site.

Figure 10:
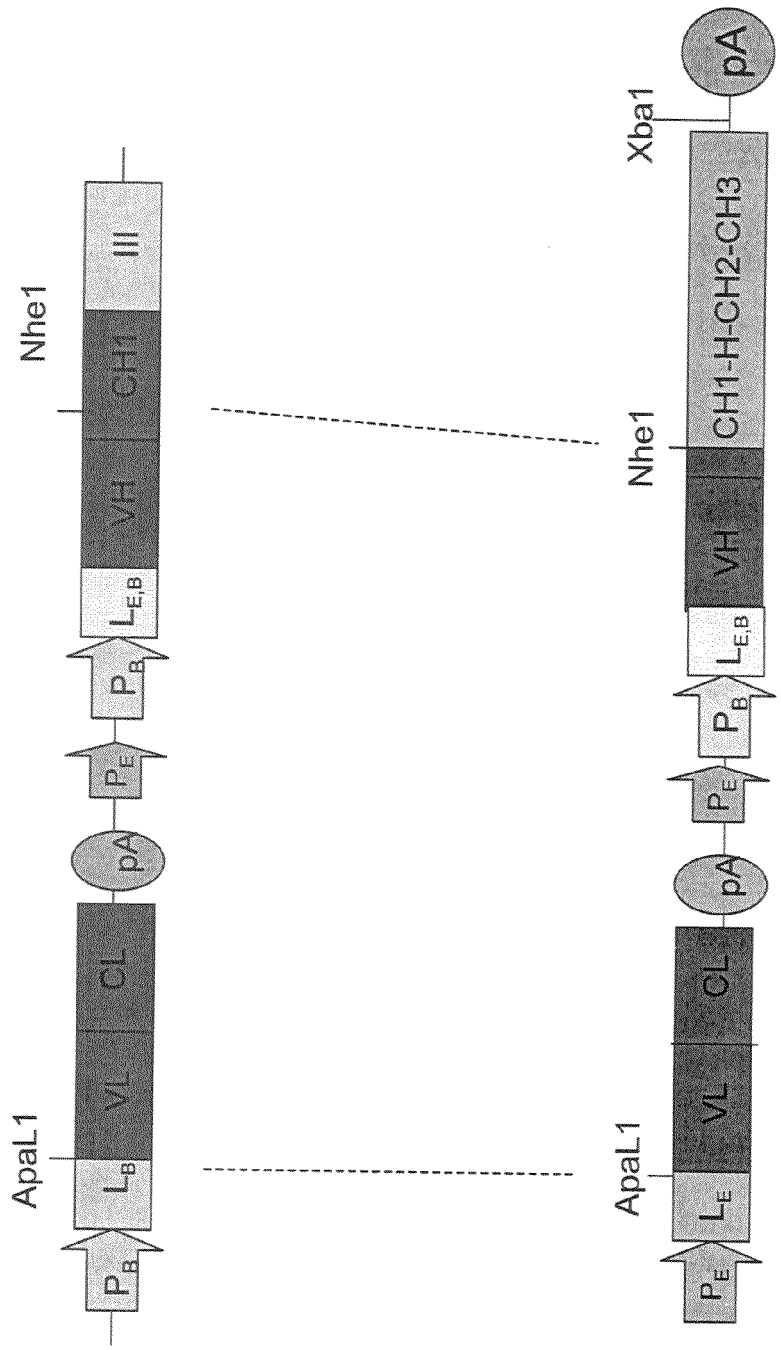

FIG. 10 is a schematic of another exemplary integrated expression vector. A Fab expression cassette in the vector can be shuttled between a prokaryotic Fab display system (top) and a mammalian IgG expression system (bottom). The Fab cassette is transferred as an ApaL1/Nhe1 fragment, in a single cloning step. Since, for the heavy chain, a leader is used that is functional in bacteria and mammalian cells, and regulatory elements for pro- and eukaryotic expression are supplied, no further (i.e. second) cloning steps are required.

(Top)—Fab display construct: a prokaryotic bicistronic expression cassette consisting of the following elements: $P_B$, prokaryotic promoter (e.g. LacZ); $L_B$, bacterial leader; VL-CL, light chain portion of Fab; pA, eukaryotic poly-adenylation signal and $P_E$, eukaryotic promoter (e.g. HCMV IE promoter; $P_B$, prokaryotic promoter; $L_{E,B}$, bifunctional leader (functional in bacteria and in mammalian cells); VH-CH1, heavy chain portion of Fab; III, gene III of a filamentous phage.

(Bottom)—IgG expression cassette: $P_E$, eukaryotic promoter; $L_E$, eukaryotic leader; VL-CL, light chain of antibody; pA, eukaryotic poly-adenylation signal and $P_E$, eukaryotic promoter (e.g. HCMV IE promoter e; $P_B$, prokaryotic promoter; $L_{E,B}$, bifunctional leader (functional in bacteria and in mammalian cells); VH-CH1-H-CH2-CH3, antibody heavy chain regions; pA, poly-adenylation site.

Figure 11:
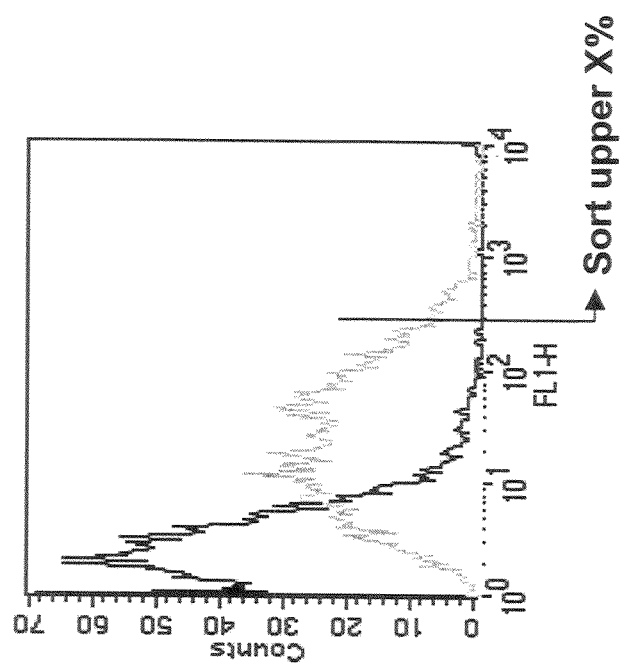

FIG. 11 is an example of a FACS selection of antibody expressing cells which capture the secreted antibody at their surface. Cells with highest expression levels (upper X %) can be isolated.

Figure 12:
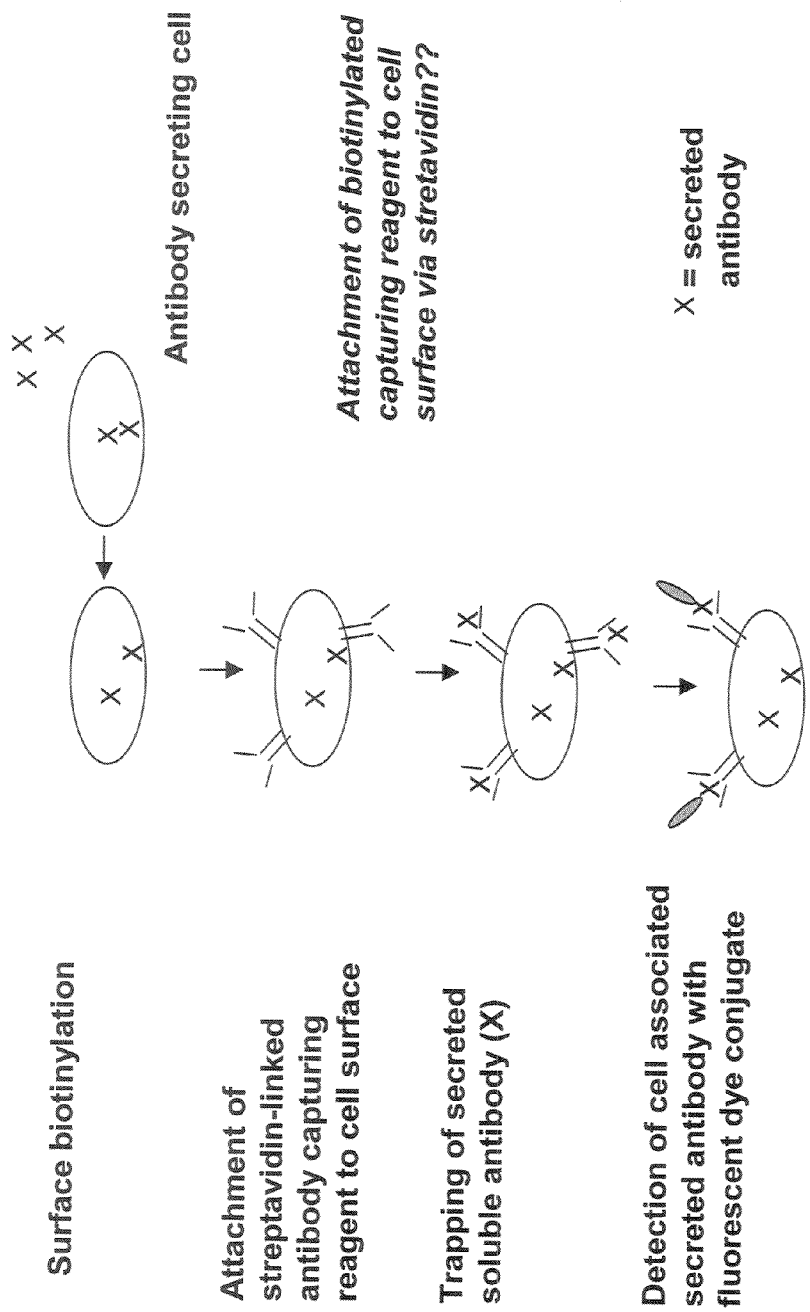

FIG. 12 is a schematic of procedure of cell surface attachment and detection of a secreted antibody on an expressing cell.

The procedure depicted consists of: surface biotinylation of antibody expressing cells, attachment of streptavidin conjugated capturing reagent (e.g. HC specific antibody), capturing of secreted antibody at the cell surface of the expressing cell and detection of surface associated secreted soluble antibody with fluorescent dye conjugate (e.g. anti LC F(a,b)$_2$-FITC).

Figure 13:
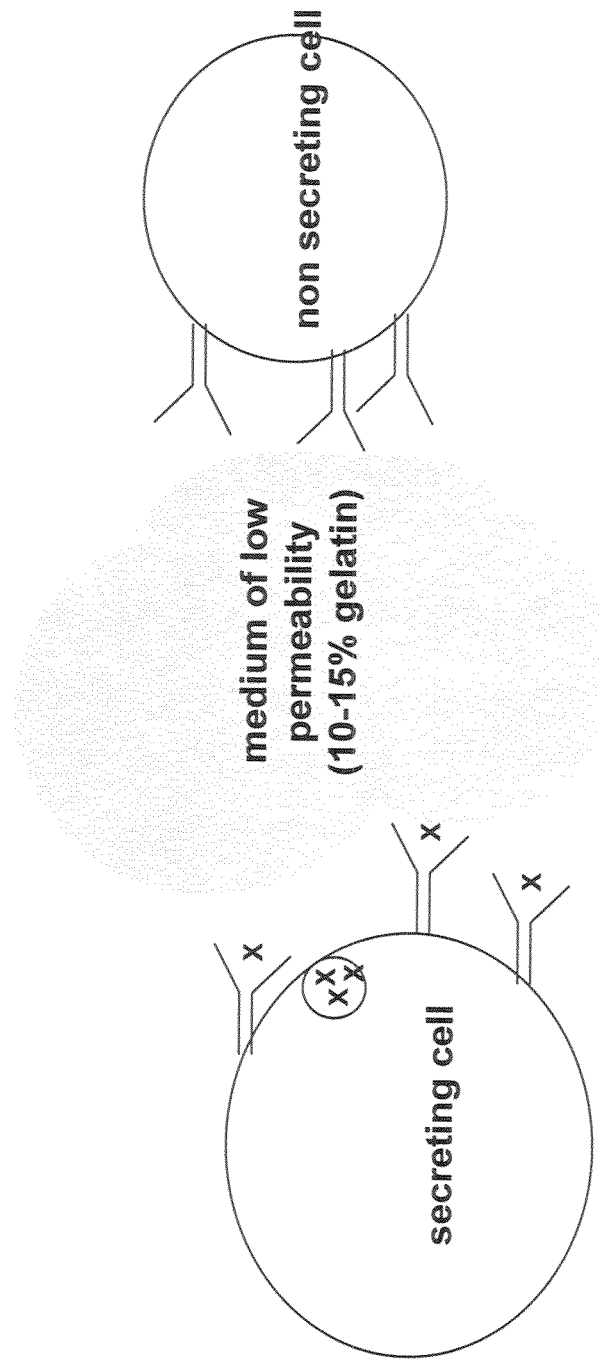

FIG. 13 is a schematic of the use of a low permeability medium during the FACS staining process. Secreting and non-secreting cells are surface biotinylated, and an antibody-capturing matrix is applied to both types of cells. Culture of cells in "medium of low permeability" during the antibody capturing phase protects cross-feeding of non-expressing by antibody expressing cells.

Figure 14:
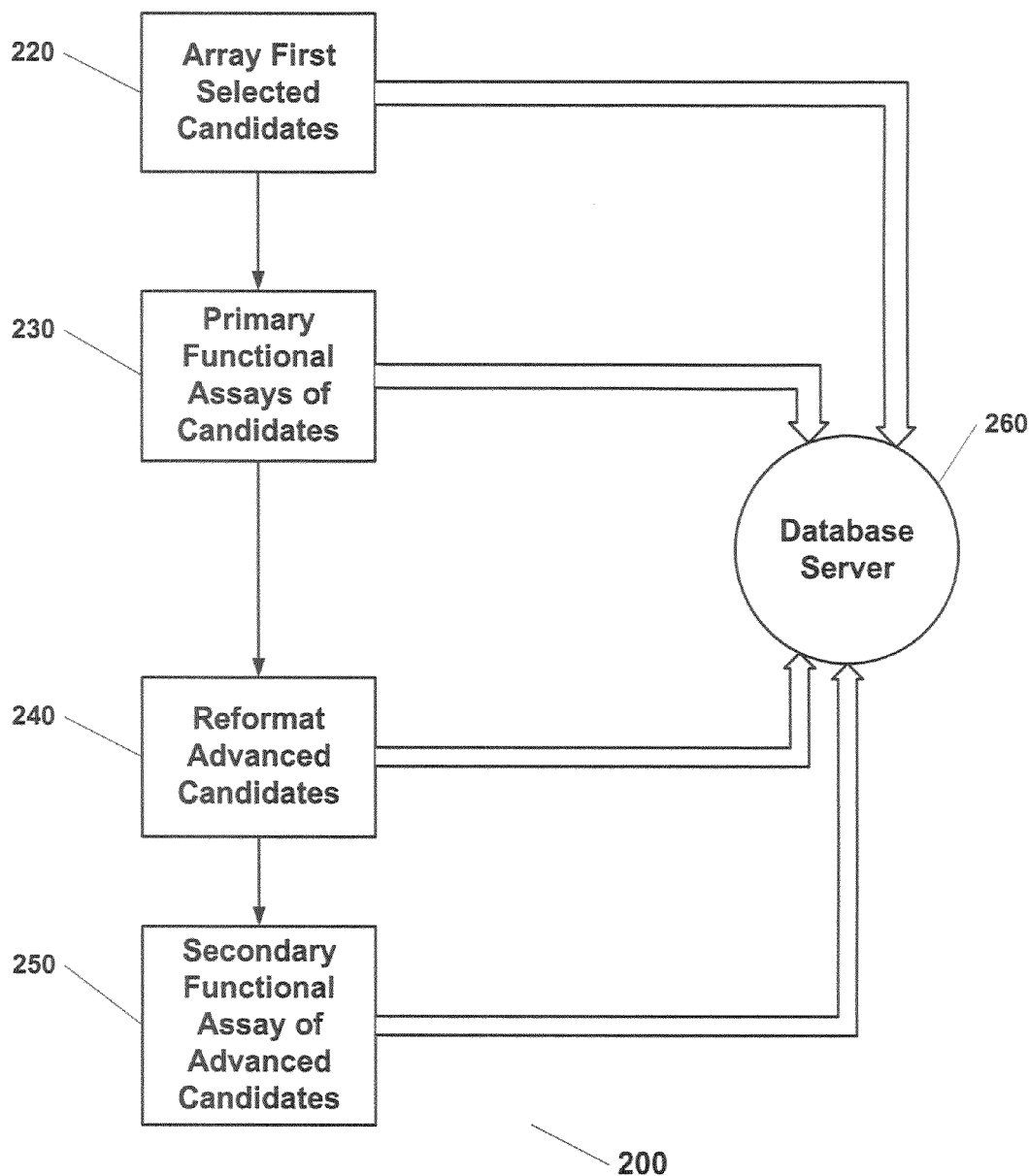

FIG. 14 is a schematic of an information management system.

Figure 15:
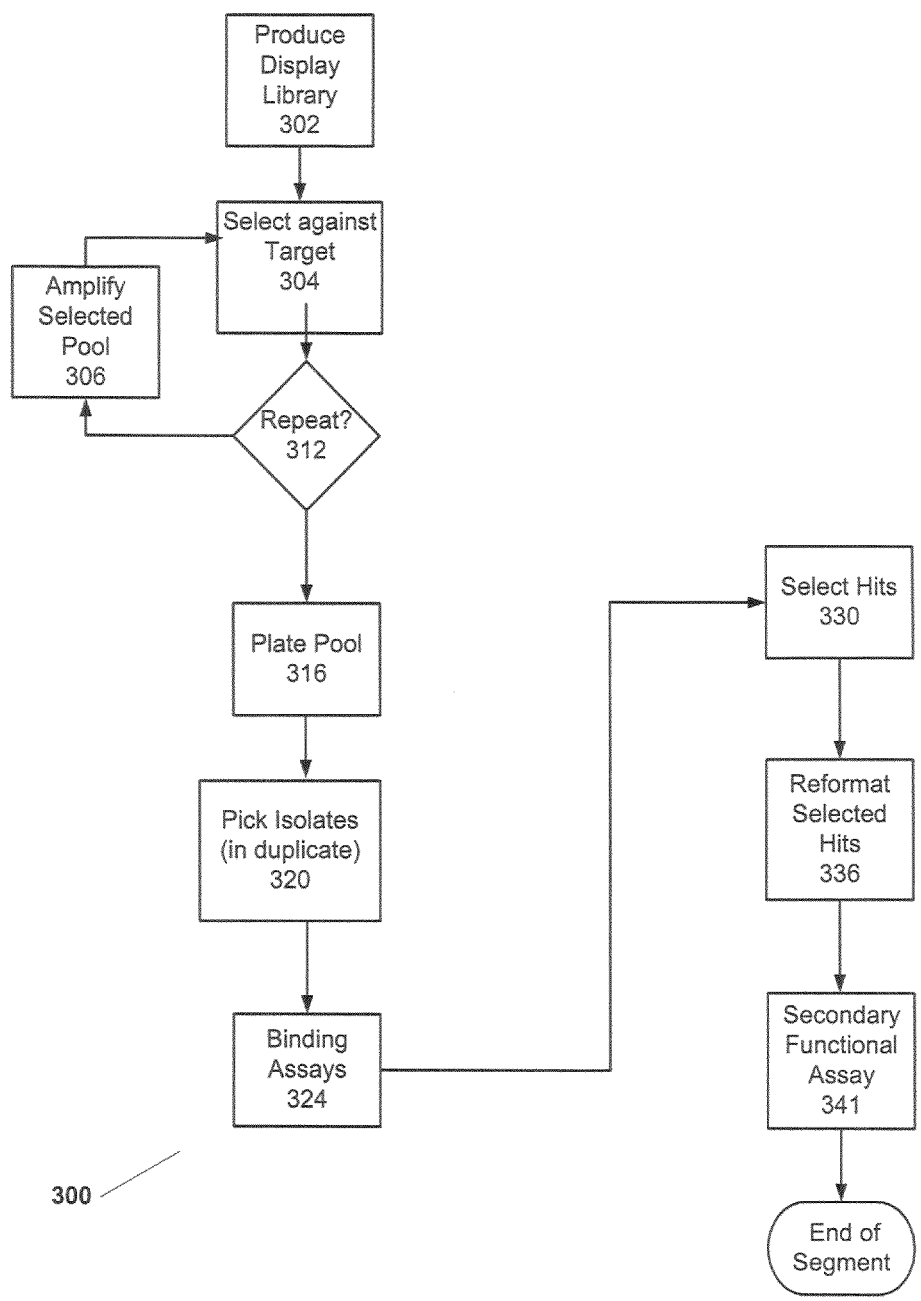

FIG. 15 is a flow chart.

Figure 16:
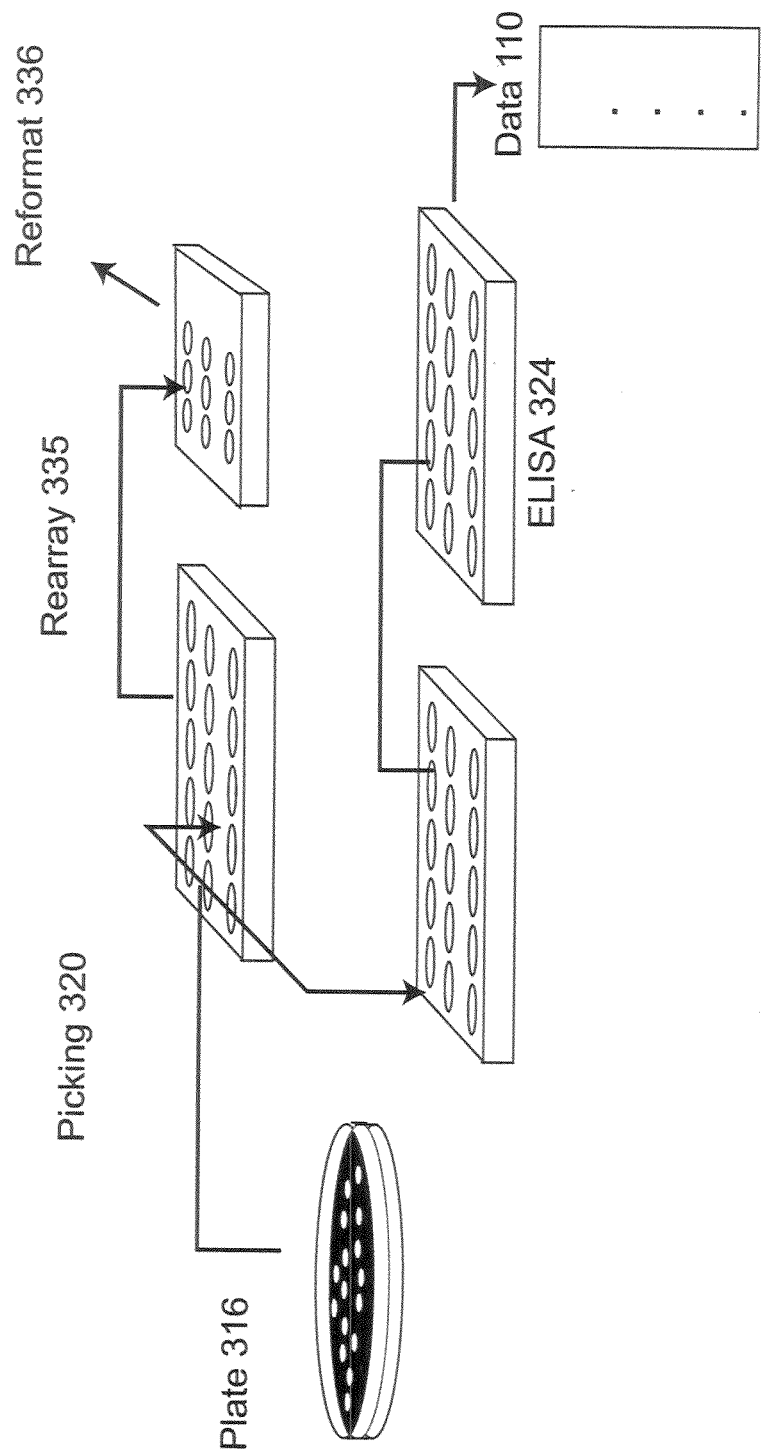

FIG. 16 is a schematic of an automated screening system.

Figure 17:
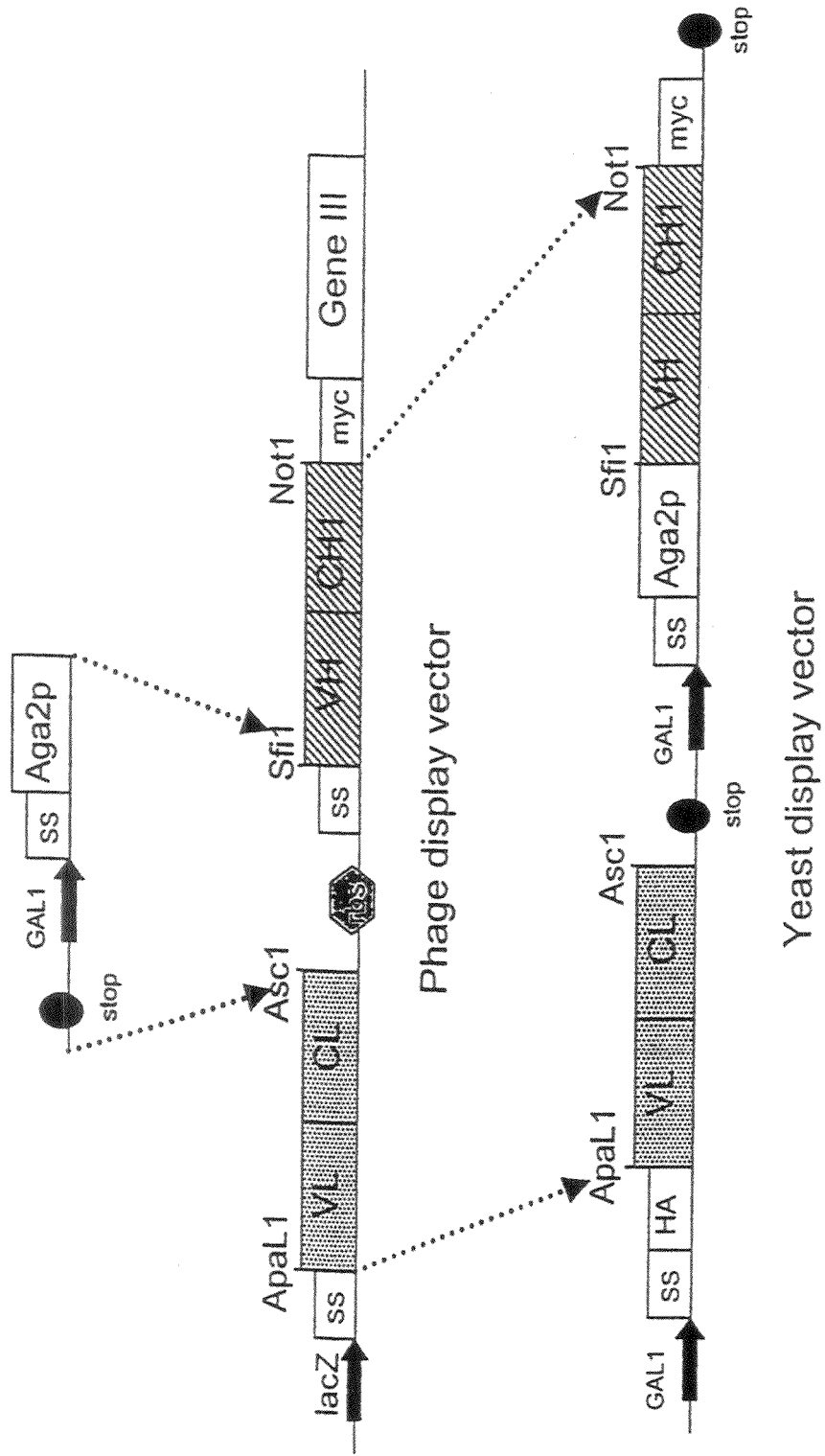

FIG. 17 depicts reformatting Fab's in a phage display vector for display on yeast cells by a yeast display vector. Combinations of Fab heavy and light chains are transferred into a yeast display vector in which expression is under control of the GAL1 promoter. The reformatting yields a yeast display vector that supports VH-CH1 expression as an Aga2 fusion protein. In the region between the two Fab chains, the following elements are provided: a second copy of GAL1 promoter, a yeast leader sequence (ss) and Aga2p coding segment that encodes a domain fused to the VH N-terminus.

FIGS. 18, 19, 20, and 21 are exemplary reformatting schemes.

FIGS. 22A and 22B provide a map and translation of IgG1 HC constant region fragment as found in pBRV and pRRV.

FIG. 23 is a map of pRRV.

FIG. 24 is a map of pBRV.

Figure 25:
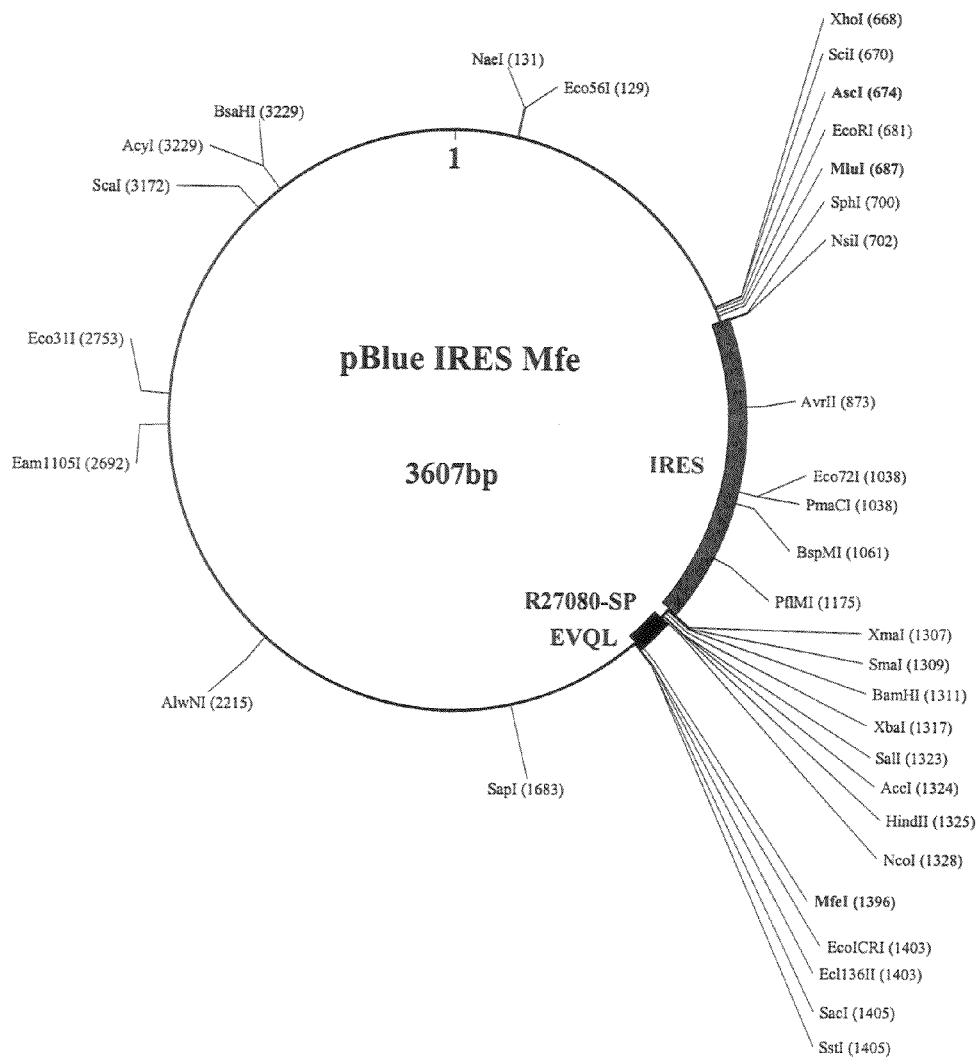

FIG. 25 is a map of pBlueIRES.Mfe. The top nucleic acid sequence is SEQ ID NO:17, its complement (middle) is SEQ ID NO:18; the encode amino acid sequence is SEQ ID NO:19.

Figure 26:
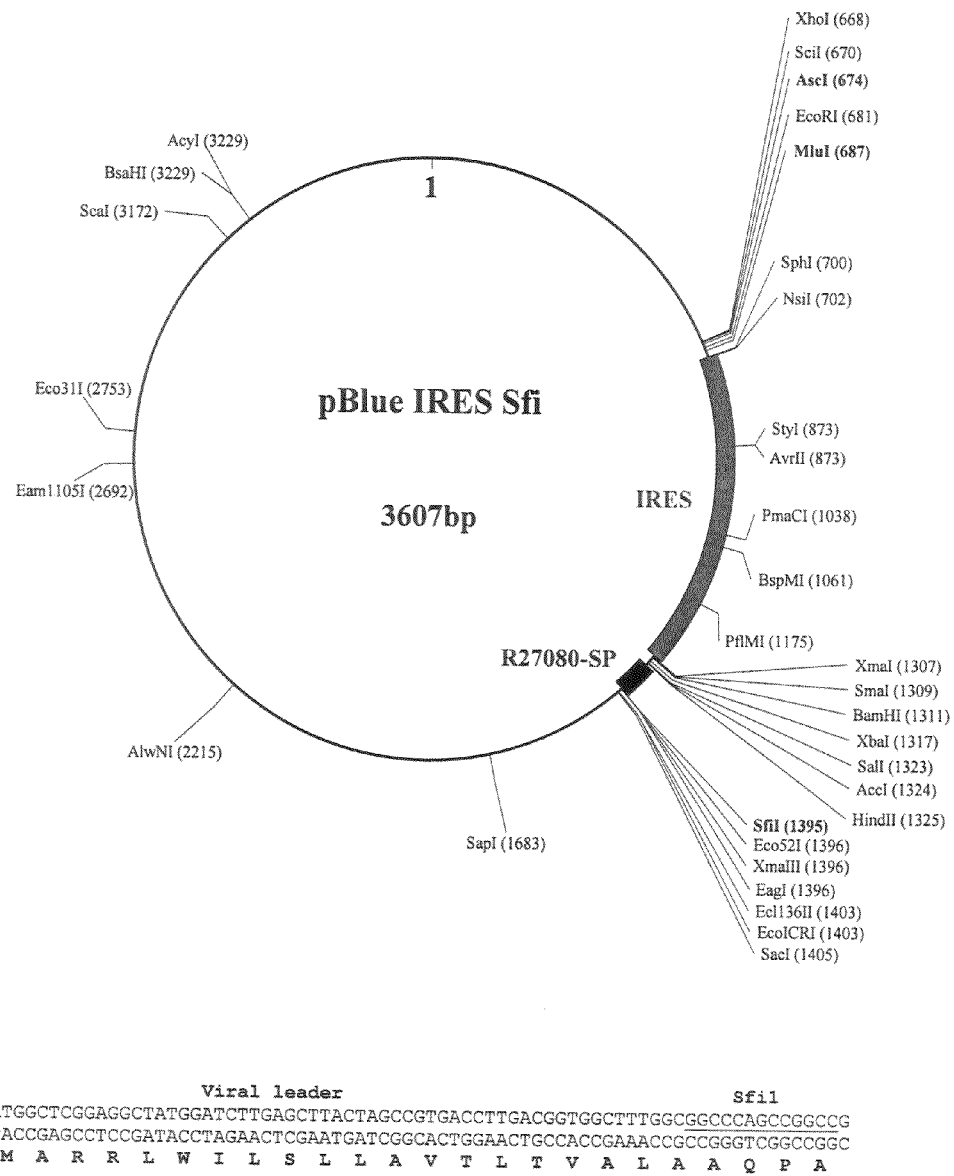

FIG. 26 is a map of pBLUE.IRES.Sfi. The top nucleic acid sequence is SEQ ID NO:20, its complement (middle) is SEQ ID NO:21; the encode amino acid sequence is SEQ ID NO:22.

Figure 27:
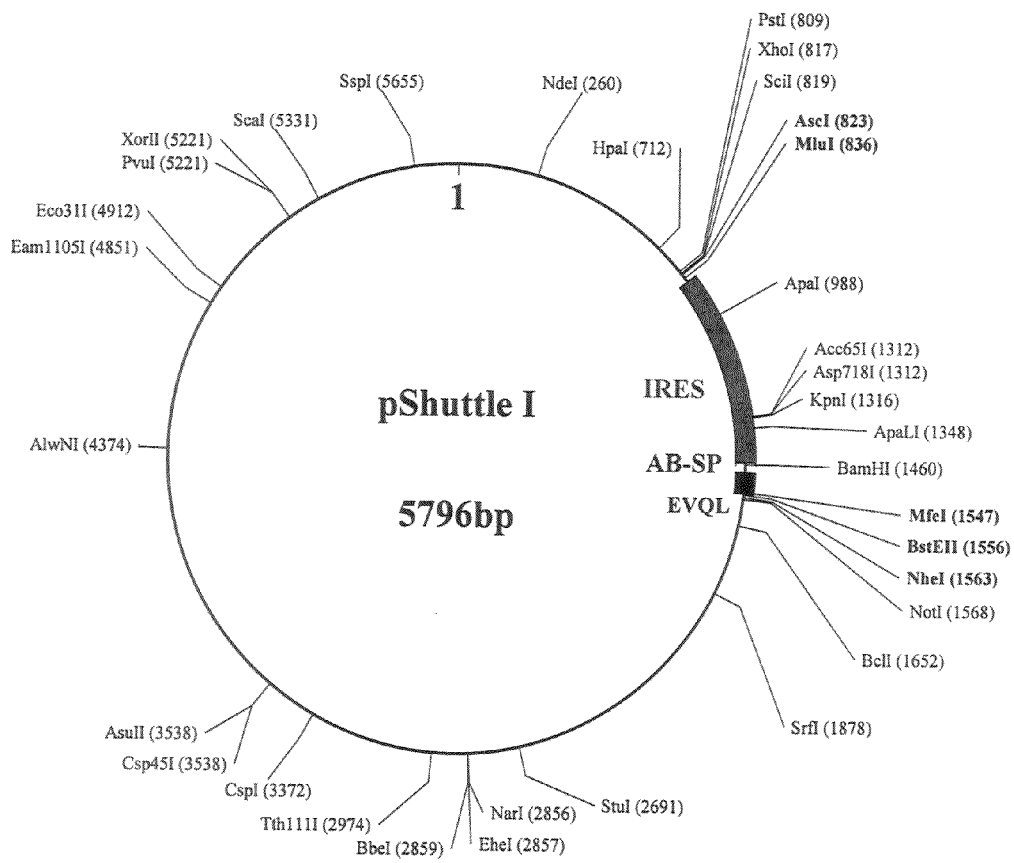

FIG. 27 is a map of pShuttleI.

Figure 28:
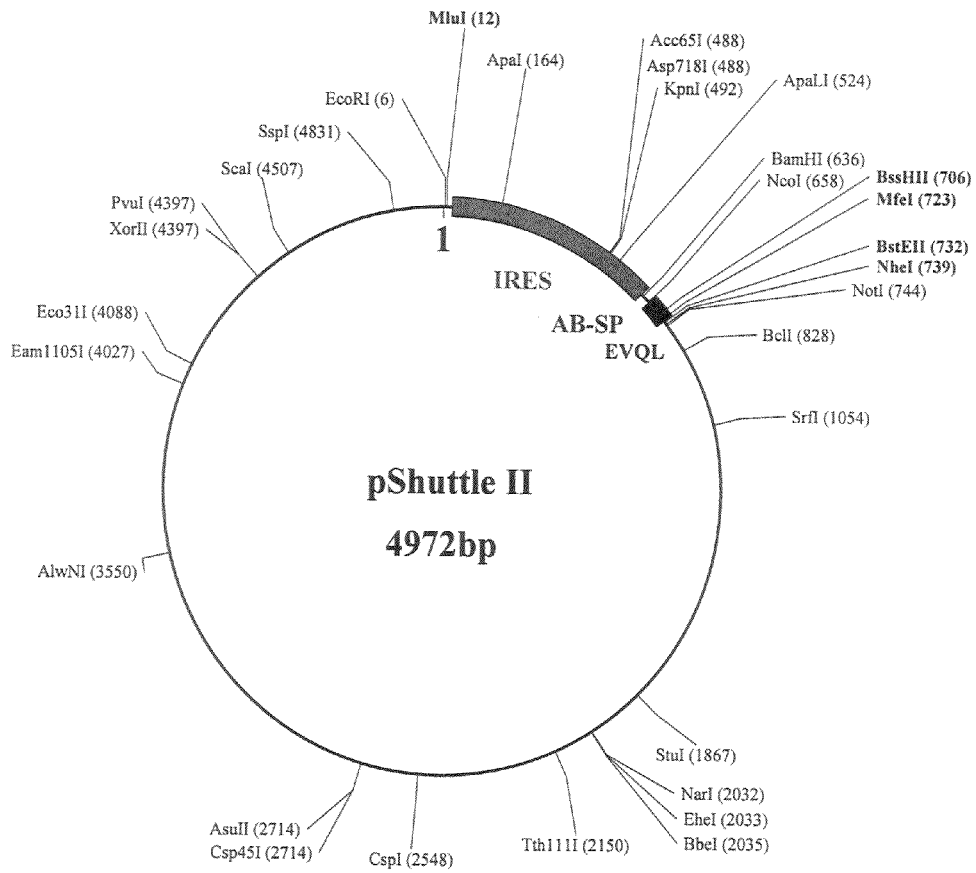

FIG. 28 is a map of pShuttleII

Figure 29:
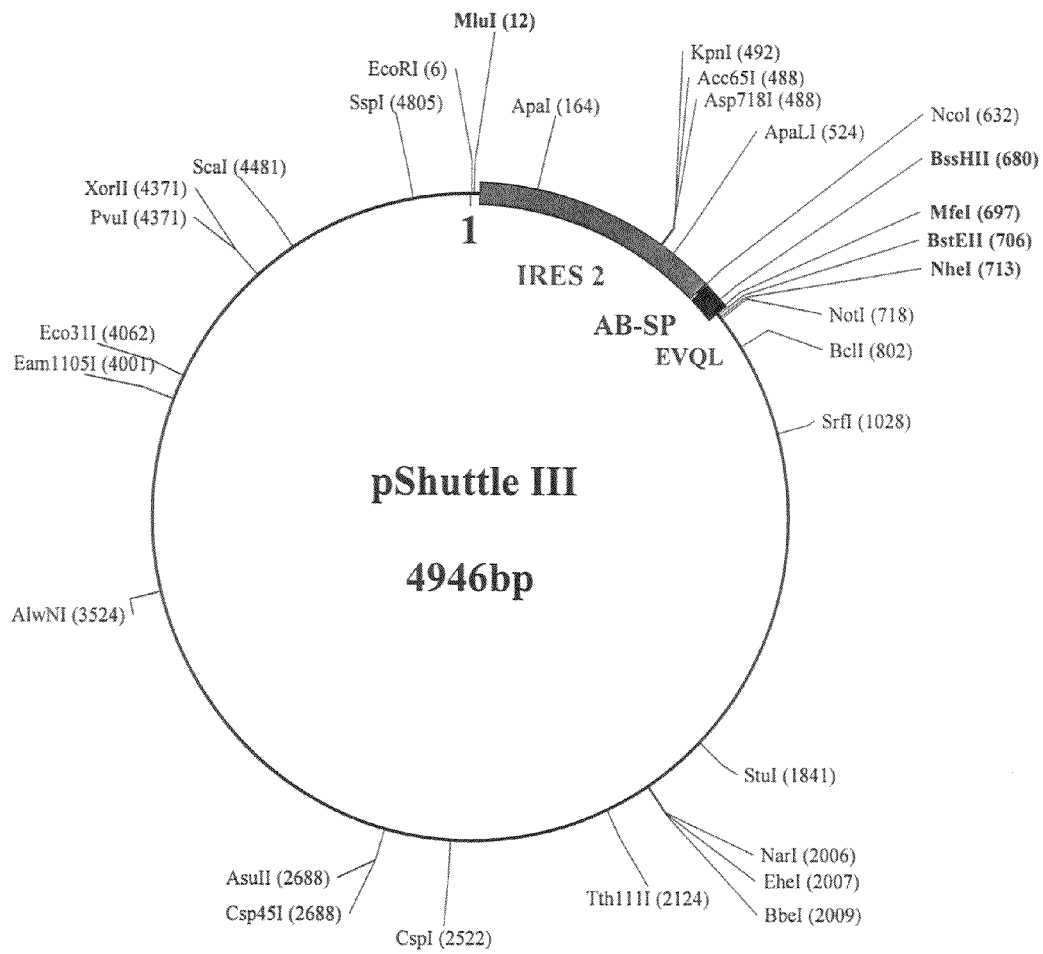

FIG. 29 is a map of pShuttleIII.

DETAILED DESCRIPTION

The invention provides, in part, platforms for identifying ligands that recognize targets. The ligands can be, for example, antibodies, T cell receptors, and immunoadhesin-type molecules. Many of the ligands include or can be linked to an effector domain.

In one exemplary aspect, a platform for antibody discovery is described. The platform, of course, can be adapted for the identification of other ligands, including those described hereinafter.

Figure 1A:
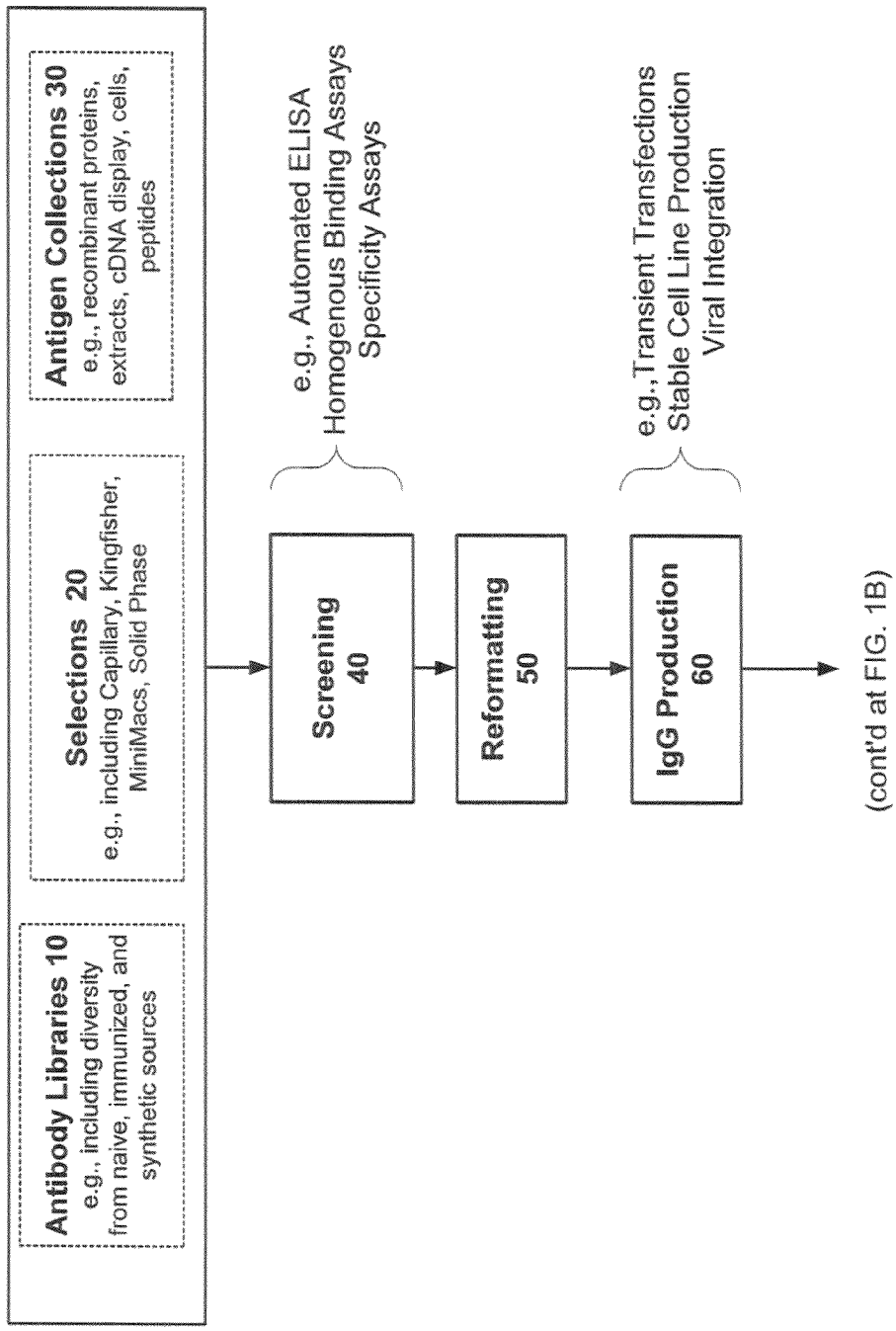
FIGS. 1A and 1B are block diagrams depicting exemplary aspects of a ligand discovery platform.
Figure 1B:
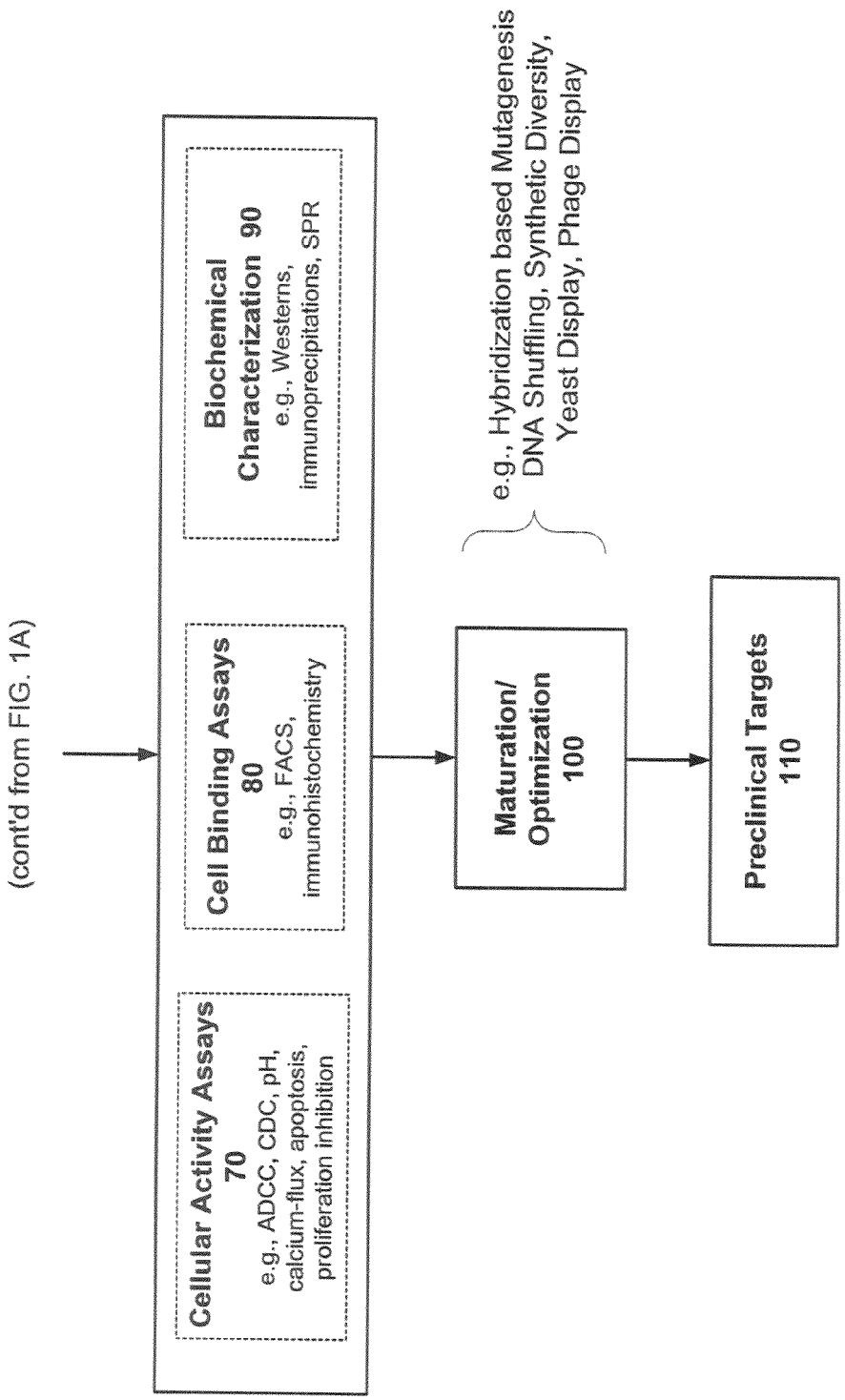

Referring now to FIG. 1, the platform includes one or more antibody libraries (10). A library, e.g., a display library, can be screened to identify members that bind to a target. A variety of selection methods are available (20). In addition, targets can be selected from a target collection (30).

In some embodiments, members of the antibody library are screened against multiple targets in parallel. After selection and optional processing steps, the target bound by each member can be determined. Examples of multiple targets include a cell that displays heterogeneous epitopes, a population of cells, a cell extract, polypeptides expressed by a cDNA library or cell-specific library, and so forth.

After one or more rounds of selections (e.g., two rounds of selections), individual candidate antibodies are isolated from the selected fraction of the library. Automated methods of screening (40) each individual candidate are described herein. Candidates which satisfy certain criteria during the screening process are reformatted (50) and advanced to IgG production (60). In another case, the selected repertoire of individual clones is reformatted provided a certain fraction of the clones satisfy a certain criterion in the screening process. This application provides a number of exemplary reformatting methods for efficiently transferring nucleic acids encoding each candidate from the initial library vector into a vector for eukaryotic expression. As seen below, the transfer process can be implemented en masse or candidate-by-candidate. Once transferred to the eukaryotic expression vector, the nucleic acid is introduced into the eukaryotic cells (typically mammalian) and expressed.

The transfer process can be implemented on a variety of scales. In one example, to produce a monoclonal immunoglobulin, an individual nucleic acid encoding a mono-specific ligand is reformatted. In another example, multiple nucleic acids (e.g., each encoding a different mono-specific ligand that binds to a different epitope of the same target molecule) are reformatted as Ig and introduced into cells as monoclonal DNA (e.g., individual species) preparations, oligoclonal DNA ensembles (e.g., a defined set) or polyclonal DNA ensembles (e.g., an incompletely characterized set of uncertain number of individual clones) for protein production. Whole IgG (or other isotypes/variants) antibodies can be isolated from the cells or media conditions by the expressing cells.

In the case of cells transfected with oligoclonal or polyclonal DNA ensembles, additional diversity may arise additional species if more than one DNA species enters an individual. This degree diversity can be controlled, e.g., by varying the nucleic acid concentration and/or transfection conditions so that cells only take up a single DNA molecule. Added diversity is useful in some embodiments, and undesirable in others.

The reformatted antibody genes can be introduced into eukaryotic cells for production of IgG by a variety of transfection methods. The production of IgG can use a transient system in which the Ig is harvested from the supernatant of cultures containing cells into which the reformatted DNA is introduced. In such transient systems, no selection to find cells that have integrated the antibody genes into their chromosomes is required. Special vector elements can be provide within the eukaryotic expression vector such as the SV40 origin of replication. After introduction of such vector in cells that harbor the large T antigen of SV40 (such as certain COS cell lines), the DNA is amplified as an episome, leading to a higher level of transient expression of the Ig. Other cells that can be used for expression are Chinese Hamster Ovary (CHO) cells, African green monkey (COS) cells, Human Embryonic Kidney 293 T (Hek293 T) cells, etc. If selection markers are provide for in the expression vector, cells can be selected after transfection and clones identified that stably express the IgG. IgG antibodies are isolated from the cells or media.

The IgG antibodies can then be assayed for a cellular activity (70), cell binding (80), and biochemical activity (90). Information for the performance of each antibody in these assays can be stored in a database. Candidate antibodies can be selected based on the collected data. The best candidates may be subjected to an in vitro antibody maturation process (100). Variants of the best candidates re-enter the process at the level of a second selection (20), screening (40), or even IgG production (60). Transient transfection of cells can be sufficient to produce some quantities of antibodies. In other circumstances, e.g., for larger quantities, stable cell lines that include DNA encoding the reformatted IgG integrated into their genome, are used.

Antibodies identified by the above process can be used in in vivo assays (e.g., using animal models) and, generally, as preclinical targets 110.

Further exemplary implementation details for aspects of this antibody development platform and related platforms are provided below.

Antibody Libraries

A nucleic acid library whose members encode antibodies, e.g., Fabs can be constructed by the exemplary methods described in de Haard et al. (1999) *J. Biol. Chem* 274:18218-30; Hoogenboom et al. (1998) *Immunotechnology* 4:1-20; Hoogenboom et al. (2000) *Immunol Today* 2:371-8 and references described therein.

In one embodiment, an antibody display library of Fabs is constructed in a phage display vector. Exemplary vectors include an expression cassette that encodes a bicistronic transcript having regions for the expression of the antibody light and heavy chain. These cassettes can include the following elements: (1) a promoter suited for constitutive or inducible expression (e.g., lac promoter); (2) a ribosome binding site and signal sequence preceding the light and heavy chain cloning regions; (3) optionally, a region following the heavy or light chain cloning region that encodes a tag sequence such as a stretch of 5-6 histidines or an epitope recognized by an antibody; (4) a suppressible codon (e.g., an amber codon); and (5) a sequence encoding a phage coat protein positioned in-frame to form a fusion to the 3' end of either the heavy or light chain.

With respect to an exemplary phagemid system, genes encoding VH and VL regions are cloned into the vector as follows. Variable heavy chain region genes are cloned as VH-gene fragments. The vector supplies all Fab's with a human CH1 domain. The VH-CH1 encoding sequence formed by insertion of the VH-gene fragments to the vector is fused (in the vector) to a sequence encoding tags for purification and detection a histidine tail for Immobilized Metal Affinity Chromatography (Hochuli, et al., (1988) *BioTechnology* 6:1321-132S) and a c-myc-derived tag (Munro, et al. (1986) *Cell* 46:291-300)), followed by an amber stop codon (Hoogenboom, et al. (1991) *Nucleic Acids Res.* 19:4133-4137) and the minor coat protein III of filamentous phage fd. The antibody light chain is cloned as full VL-CL fragment, for directed secretion and assembly with the VH-CH1 on the phage particle. When the bicistronic mRNA is transcribed and translated in a amber-suppressing host cell, both polypeptide subunits are produced and join in the periplasm to produce Fab fragments that are tethered to the phage gene III protein or fragment thereof.

Antibody libraries can be incorporate diversity from a variety of sources, including from synthetic nucleic acid, naïve nucleic acids, patients (e.g., immunized or diseased human subjects), and animals (e.g., immunized animals).

Natural Immune Sources.

In one embodiment, immune cells can be used as a natural source of diversity for the variation of antibodies, MHC-complexes and T cell receptors. Some examples of immune cells are B cells and T cells. The immune cells can be obtained from, e.g., a human, a primate, mouse, rabbit, camel, or rodent. The cells can be selected for a particular property. For example, T cells that are $CD4^+$ and $CD8^-$ can be selected. B cells at various stages of maturity can be selected.

In another embodiment, fluorescent-activated cell sorting is used to sort B cells that express surface-associated IgG molecules. Further B cells expressing different isotypes of IgG can be isolated. In another embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin or pokeweed mitogen.

In still another embodiment, the cells are isolated from a subject that has an immunological disorder, e.g., systemic lupus erythematosus (SLE), rheumatoid arthritis, vasculitis, Sjögren's syndrome, systemic sclerosis, or anti-phospholipid syndrome. The subject can be a human, or an animal, e.g., an animal model for the human disease, or an animal having an analogous disorder. In still another embodiment, the cells are isolated from a transgenic non-human animal that includes a human immunoglobulin locus.

In one embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al. (2001) *J Immunol.* 166:2228). In another embodiment, the cells are naïve.

Naturally diverse sequences can be obtained as cDNA produced from mRNAs isolated from cell and samples described herein. Full length (i.e., capped) mRNAs are separated (e.g. by degrading uncapped RNAs with calf intestinal phosphatase). The cap is then removed with tobacco acid pyrophosphatase and reverse transcription is used to produce the cDNAs. The reverse transcription of the first (antisense) strand can be done in any manner with any suitable primer. See, e.g., de Haard et al. (1999) *J. Biol. Chem* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. Poly-dT primers (e.g., for the heavy-chain genes) or synthetic primers that hybridize to a synthetic sequence ligated to the mRNA strand may also be used.

cDNA can be amplified, modified, fragmented, or cloned into a vector to form an antibody library. See, e.g., de Haard et al. (1999) supra. Also, for example, see U.S. Provisional Application 60/343,954, filed Oct. 24, 2001, "HYBRIDIZATION CONTROL OF SEQUENCE VARIATION" describes a method of cleaving cDNA using oligonucleotide-directed cleavage and incorporating immunological diversity into a template immunoglobulin sequence.

Murine-Derived Human Immunoglobulins.

In one embodiment, the immunize animal is a transgenic animal (e.g., a mouse) that has human immunoglobulin genes. See, e.g., U.S. Pat. No. 6,150,584; Fishwild et al. (1996) *Nature Biotechnol.* 14:845-85; Mendez et al. (1997) *Nature Genet.* 15:146-156; Nicholson et al. (1999) *J. Immunol.* 163:6898. One such transgenic mouse can be constructed as described in WO 94/02602 using a YAC for the human heavy chain locus, e.g., yH1C (1020 kb), and human light chain locus YAC, e.g., yK2 (880 kb). yH1C includes 870 kb of the human variable region, the entire D and JH region, human μ, δ, γ2 constant regions and the mouse 3' enhancer. yK2 includes 650 kb of the human kappa chain proximal variable region (Vκ), the entire Jκ region, and Cκ with its flanking sequences. Administration of an antigen to such mice elicits the generation of human antibodies against the antigen. The spleens of such mice are isolated. mRNA encoding the human antibody genes is extracted and used to produce a nucleic acid library encoding antibodies against the antigen. In some implementations, the library is mutagenized, e.g., affinity matured, in vitro prior to selection and screening.

Synthetic Diversity.

A nucleic acid library can also include synthetic diversity at one or more positions, e.g., in one or more CDRs. Libraries can include regions of diverse nucleic acid sequence that originate from artificially synthesized sequences. Typically, these are formed from degenerate oligonucleotide populations that include a distribution of nucleotides at each given position. The inclusion of a given sequence is random with respect to the distribution. One example of a degenerate source of synthetic diversity is an oligonucleotide that includes NNN wherein N is any of the four nucleotides in equal proportion.

Synthetic diversity can also be more constrained, e.g., to limit the number of codons in a nucleic acid sequence at a given trinucleotide to a distribution that is smaller than NNN. For example, such a distribution can be constructed using less than four nucleotides at some positions of the codon. In addition, trinucleotide addition technology can be used to further constrain the distribution.

So-called "trinucleotide addition technology" is described, e.g., in Wells et al. (1985) *Gene* 34:315-323, U.S. Pat. No. 4,760,025 and WO 91/19818. Oligonucleotides are synthesized on a solid phase support, one codon (i.e., trinucleotide) at a time. The support includes many functional groups for synthesis such that many oligonucleotides are synthesized in parallel. The support is first exposed to a solution containing a mixture of the set of codons for the first position. The unit is protected so additional units are not added. The solution containing the first mixture is washed away and the solid support is deprotected so a second mixture containing a set of codons for a second position can be added to the attached first unit. The process is iterated to sequentially assemble multiple codons. Trinucleotide addition technology enables the synthesis of a nucleic acid that at a given position can encoded a number of amino acids. The frequency of these amino acids can be regulated by the proportion of codons in the mixture. Further the choice of amino acids at the given position is not restricted to quadrants of the codon table as is the case if mixtures of single nucleotides are added during the synthesis.

Selections

The selection process (20) can be performed manually or using an automated method. In some cases, non-specific binding and other non-ideal properties require more than one selection cycle. Additional selection cycles increase the enrichment for candidate library members. To repeat a selection step, eluted library members are amplified then reapplied to the target ligand. Depending on the implementation, different numbers of selection cycles may be sufficient to identify a pool of candidate library members from a library having a vast diversity. For example, one, or two rounds of selection may be sufficient. A set of selection cycles is referred to as a selection campaign.

Some exemplary selection processes are as follows.

Panning.

The target molecule is immobilized to a solid support such as a surface of a microtitre well, matrix, particle, or bead. The display library is contacted to the support. Library members that have affinity for the target are allowed to bind. Non-specifically or weakly bound members are washed from the support. Then the bound library members are recovered (e.g., by elution) from the support. Recovered library members are collected for further analysis (e.g., screening) or pooled for an additional round of selection.

Magnetic Particle Processor.

One example of an automated selection uses magnetic particles and a magnetic particle processor. In this case, the target is immobilized on the magnetic particles, e.g., as described below. The KingFisher™ system, a magnetic particle processor from Thermo LabSystems (Helsinki, Finland), is used to select display library members against the target. The display library is contacted to the magnetic particles in a tube. The beads and library are mixed. Then a magnetic pin, covered by a disposable sheath, retrieves the magnetic particles and transfers them to another tube that includes a wash solution. The particles are mixed with the wash solution. In this manner, the magnetic particle processor can be used to serially transfer the magnetic particles to multiple tubes to wash non-specifically or weakly bound library members from the particles. After washing, the particles are transferred to a tube that includes an elution buffer to remove specifically and/or strongly bound library members from the particles. These eluted library members are then individually isolated for analysis (e.g., screening) or pooled for an additional round of selection.

An exemplary magnetically responsive particle is the Dynabead® available from Dynal Biotech (Oslo, Norway). Particles can be blocked with a blocking agent, such as serum albumin (e.g., BSA) or casein to reduce non-specific binding and coupling of compounds other than the target to the particle. The target is attached to the paramagnetic particle directly or indirectly. A variety of target molecules can be purchased in a form linked to paramagnetic particles. In one example, a target is chemically coupled to a particle that includes a reactive group, e.g., a crosslinker (e.g., N-hydroxysuccinimidyl ester) or a thiol.

In another example, the target is linked to the particle using a member of a specific binding pair. For example, the target can be coupled to biotin. The target is then bound to paramagnetic particles that are coated with streptavidin (e.g., M-270 and M-280 Streptavidin Dynaparticles® available from Dynal Biotech, Oslo, Norway). In one embodiment, the target is contacted to the sample prior to attachment of the target to the paramagnetic particles. Other specific binding pairs (e.g., a peptide epitope and corresponding monoclonal antibody) can be used. (see, e.g., Kolodziej and Young (1991) *Methods Enz.* 194:508-519).

Capillary Device for Washing Magnetic Beads.

Provisional application 60/337,755, filed Dec. 7, 2001, "Method and Apparatus for Washing Magnetically Responsive Particles" describes an apparatus and methods that can, in one implementation, be used to wash magnetic particles in a capillary tube. On exemplary apparatus features a capillary that houses magnetic particles. The chamber is located between a first magnet and a second magnet. The magnets and are attached to a frame that can be actuated from a first position to a second position. When the frame is actuated, the magnetic particles in the capillary are agitated.

To use the apparatus for display library screening, library members are contacted to magnetic particles that have an attached target. The particles are disposed in the capillary (before, during, or after the contacting). Then, the particles are washed in the capillary with cycles of agitation and liquid flow to remove non-specifically or weakly bound library members. After washing, bound library members can be eluted or dissociated from the particles and recovered.

MiniMACS™ is still another device, available from Miltenyi Biotec GmbH (Gladbach, Germany), which can be used for magnetic particle-based separations.

Cell-Based Selections.

The selection can be performed by binding the display library to target cells, and then selecting for library members that are bound by the cells. Cell-based selections enable the identification of ligands that recognize target molecules as presented in their natural milieu, e.g., including post-translational modifications, associated proteins and factors, and competing factors. Further, since cell-based selections are not directed against a specific singular target molecule, no a priori information is required about the target. Rather, the cell itself is a determinant. Later steps, particular functional assays, can be used to verify that identified ligands are active in targeting effector functions to the cell.

In one embodiment, the selection further requires that the library members are internalized by the target cells. This method selects both for binding of the antibody ligand to the target cell and for endocytosis of the antibody ligand into the cell. See, e.g., Heitner et al. (2001) *J. Immunol. Methods.* 248:17-30; Poul et al. (2000) *J. Mol. Biol.* 301:1149-1161.

Non-limiting examples of cells include cancer cells, hematopoietic cells, fibroblasts, transformed cells, BaII cells, and so forth. Such cells are attached to magnetically responsive particles using an antibody specific for a marker on the cell surface, e.g., CD19 or a cell-surface cancer-specific antigen (for example, hypoglycosylated MUC1, melanoma differentiation antigen gp100, or CEA1.).

Another class of targets includes cells, e.g., fixed or living cells. The cell can be bound to an antibody that is attached to a solid support (e.g., a paramagnetic particle or a surface of a growth chamber). For example, a biotinylated rabbit anti-mouse Ig antibody is bound to streptavidin paramagnetic beads and a mouse antibody specific for a cell surface protein of interest is bound to the rabbit antibody.

In one embodiment, the cell is a recombinant cell, e.g., a cell transformed with a heterologous nucleic acid that expresses a heterologous gene or that disrupts or alters expression of an endogenous gene. The cells can be transformed with a plasmid that expresses (e.g., under control of an inducible or constitutive promoter) a cell-surface protein of interest. The plasmid can also express a marker protein, e.g., for use in binding the transformed cell to a solid support, e.g., a magnetic particle. The cells can express a heterologous intracellular protein, e.g., an oncogene, transcription factor, or cell-signalling protein. The intracellular protein can alter cell behavior or the repertoire of molecules on the cell surface.

In another embodiment, the cell is a primary culture cell isolated from a subject, e.g., a patient, e.g., a cancer patient. In still another embodiment, the cell is a transformed cell, e.g., a mammalian cell with a cell proliferative disorder, e.g., a neoplastic disorder. In still another embodiment, the cell is the cell of a pathogen, e.g., a microorganism such as a pathogenic bacterium, pathogenic fungus, or a pathogenic protist (e.g., a *Plasmodium* cell) or a cell derived from a multicellular pathogen.

Cells can be treated, e.g., at a particular stage of the selection. The treatment can be a drug or an inducer of a heterologous promoter-subject gene construct. The treatment can cause a change in cell behavior, morphology, and so forth. In some implementations, display library members that associate or dissociate from the cells upon treatment are collected and analyzed.

In still another embodiment, the cells are treated (e.g., using a drug or genetic alteration) to alter the rate of endocytosis, pinocytosis, exocytosis, and/or cell secretion.

In Vivo Selections.

The selection can be done in vivo to identify library members that bind to a target tissue or organ, e.g., as described in Kolonin et al. (2001) *Current Opinion in Chemical Biology* 5:308-313, Pasqualini and Ruoslahti (1996) *Nature* 380:364-366, and Paqualini et al. (2000) "In vivo Selection of Phage-Display Libraries" In *Phage Display: A Laboratory Manual* Ed. Barbas et al. Cold Spring Harbor Press 22.1-22.24. For example, a phage display library is injected into a subject (e.g., a human or other mammal). After an appropriate interval, a target tissue or organ is removed from the subject and the display library members that bind to the target site are recovered and characterized.

Screening

After selection, the identified members of the pool are individually isolated and screened. Screening can also be automated (see below).

A screening differs from a selection in that, a screen is characterized by the analysis of library members individually (or in pools) whereas a selection is characterized by analysis of library members that are separated from other members during the process (e.g., retained, eluted, or washed off). In some implementations, a collection of library members is directly screened, without being subjected to a selection step. This approach, for example, can be used during affinity maturation and refinement protocols.

For the screen, each identified member is assayed for a functional property, typically a binding activity (including, for example, information related to specificity, a kinetic parameter, an equilibrium parameter, avidity, affinity, and so forth). The functional information can also relate to one or more of the following: a structural or biochemical property (e.g., thermal stability, oligomerization state, solubility and so forth), a physiological property (e.g., renal clearance, toxicity, target tissue specificity, and so forth) and so forth.

This information can be obtained in two phases of screening. In the primary phase, typically the binding properties of selected display library members are verified using the binding moiety without an effector domain. Members that meet a set of selection criteria (or a criterion) are selected for reformatting and mammalian cell expression with a linked effector domain. In the secondary phase, functional information is obtained from the mammalian cell-expressed ligand complete with a linked effector domain.

The following describes possible embodiments of exemplary assays for binding assays:

ELISA.

In one implementation, ELISA assays are used to evaluate the affinity of each identified library member for the target and for a non-target. For example, each polypeptide from the identified members is contacted to a microtitre plate whose bottom surface has been coated with the target, e.g., a limiting amount of the target. The plate is washed with buffer to remove non-specifically bound polypeptides. Then the amount of the polypeptide bound to the plate is determined by probing the plate with an antibody that can recognize the polypeptide, e.g., a tag or constant portion of the polypeptide. The antibody is linked to an enzyme such as alkaline phosphatase, which produces a colorimetric product when appropriate substrates are provided. The polypeptide can be purified from cells or assayed in a display library format, e.g., as a fusion to a filamentous bacteriophage coat. In another version of the ELISA assay, each polypeptide of a library is used to coat a different well of a microtitre plate. The ELISA then proceeds using a constant target molecule to query each well.

Homogeneous Binding Assays.

Protein ligands identified from the display library can be screened using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). Another example of a homogenous assay is Alpha Screen (Packard Bioscience, Meriden Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding. The homogenous assays can be performed while the candidate polypeptide is attached to the display library vehicle, e.g., a bacteriophage.

Protein Arrays.

Protein ligands identified from the display library can also be screened using protein arrays. The polypeptides are immobilized on a solid support, for example, on a bead or an array. For a protein array, each of the polypeptides is immobilized at a unique address on a support. Typically, the address is a two-dimensional address. Methods of producing polypeptide arrays are described, e.g., in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 01/40803 and WO 99/51773. Polypeptides for the array can be spotted at high speed, e.g., using commercially available robotic apparati, e.g., from Genetic MicroSystems or BioRobotics.

Library members that are specific for the target can be characterized by nucleic acid sequencing. Sequence information is used to classify the members and to remove redundant members (i.e., members that encode that same antibodies).

Library members that meet a given criterion (or criteria) are advanced to IgG Production (50). First, the library members are reformatted from the prokaryotic phage library vector into a vector for mammalian cell expression.

Reformatting

The reformatting process is used, for example, to transfer nucleic acid from a display vector to a vector suitable for mammalian cell production. The transfer process can also include modifications (e.g., substitution, insertion, or deletion of sequences) that facilitate expression in a mammalian expression system. Such modifications include sequences for transcription, translation, secretion, effector domains function, and selection. Further, other modifications are also possible, e.g., the inclusion of introns and so forth.

In one embodiment, each selected library member is reformatted individually. In another embodiment, the library members are combined and reformatted en masse.

The reformatting process can be tailored to the expression system used initially for display and for the secondary expression system. For example, for phage display, the coding of heavy and light chains by a single bicistronic transcript favors stoichiometric production of the two chains as well as efficient transcription and translation. This design requires a tandem organization of the nucleic acid sequences encoding the heavy and light chains such that they are in the same translational orientation. The reformatting process maintains this orientation while modifying the sequences to either encode a bicistronic transcript that can be expressed in mammalian cells or to produce two separate transcripts. Only two cycles of restriction digestion and ligation are required for the reformatting.

In one example of en masse reformatting, the first cycle includes digesting display vectors to release nucleic acid fragments that include minimally a light chain variable coding region and a heavy chain variable coding region. The fragments are cloned into a vector for mammalian expression. During this cycle, the transfer of the nucleic acid fragments encoding both chains insures that combinations of heavy and light chain present in the display vector are maintained in the mammalian vector. Further, the transfer process can be used to switch from a prokaryotic promoter to a mammalian promoter on the 5' end of the coding strand and from a sequence encoding a bacteriophage coat protein (or fragment thereof) to a sequence encoding an Fc domain on the 3' end of the coding strand. General methods for cloning are described in standard laboratory manuals, e.g., Sambrook et al. (2001) Molecular Cloning: A Laboratory Manual (Third Edition), Cold Spring Harbor Laboratory Press.

In the second cycle, the region intervening between the light chain coding region and the heavy chain-coding region is substituted. A sequence that includes a prokaryotic ribosome binding site is removed, and a sequence with an internal ribosomal entry site (IRES) or a sequence including a eukaryotic promoter is inserted. Also in this process the prokaryotic signals for secretion (e.g., a signal sequence at the 5' end of the Ig coding region) can be replaced by an eukaryotic signal sequence. In some implementations, the intervening region is substituted by recombination in a cell. In still others, the intervening region is not substitute, but rather sequences are inserted e.g., using site-specific recombination, and optionally without excising the sequences designed for prokaryotic expression.

Hybrid signal sequences that are functional in both prokaryotic and eukaryotic cells can be used to obviate reformatting of some (e.g., at least the 3' region of the signal sequence, e.g., the −3, −2, and −1 positions) or all of the signal sequence. In some cases, a signal sequence is functional in multiple expression systems (e.g., both pro- and eukaryotic systems). For example, the signal sequence of some bacterial beta-lactamases is functional in eukaryotic cells and prokaryotic cells. See, e.g., Kronenberg et al., 1983, J. Cell Biol. 96, 1117-9; Al-Qahtani et al., 1998, Biochem. J. 331, 521-529. Signal sequences that function in multiple hosts can also be designed on the basis of the requirement of such signal sequence (consensus rules) in the respective expression hosts (e.g., as shown in FIG. 8), or may be selected empirically.

Signal sequences that function in both expression systems (e.g., prokaryotic and eukaryotic) do not need to be replaced by the reformatting procedure. Thus, only one modification may be required. In FIGS. 9 and 10 (top), a vector system is used that requires only one modification in order to be appropriately reformatted for expression in multiple expression systems (e.g., prokaryotic and eukaryotic). In this case the signal is used to drive the secretion of a heavy chain VH-CH1 fused to a phage derived pIII protein, in prokaryotic cells, for Fab phage display, and, after a single recloning step, the expression cassette encodes a full IgG (i.e., including an Fc region) that can be expressed in a mammalian cell.

Features of a Mammalian Expression Vector.

Some key features of a mammalian expression vector which may be introduced by the reformatting process include: a transcriptional regulatory sequence, a internal ribosome entry site, a chromatin control sequence, a localization signal, and a leader sequences. Similar considerations may apply to enhancers, untranslated regions, poly adenylation sites, selectable markers, and so on.

Transcriptional Regulatory Sequences.

Transcriptional control sequences are used to drive expression of transcripts encoding both subunits of the antibody ligand. For high level expression, for example, exemplary enhancer/promoter regulatory elements include elements derived from SV40, CMV, adenovirus and the like, such as a CMV enhancer/AdMLP promoter regulatory element or an SV40 enhancer/AdMLP promoter regulatory element. See, e.g., U.S. Pat. No. 5,385,839.

Still other transcriptional regulatory sequences are selected for driving cell or tissue-specific expression. For example, to express an antibody ligand ectopically in a cytotoxic T cell, a T-cell specific promoter is used.

Chromatin Control Sequences.

These sequences include elements, e.g., those variously termed insulators (or insulator element), locus control regions (which are frequently tissue specific), and chromatin opening elements (which frequently are not tissue specific). As defined herein, chromatin control sequences are sequences that insulate the transcription of genes placed within its range of action but which does not perturb gene expression, either negatively or positively. For example, they modulate (e.g., shield) the regulatory effects of chromatin and nearby sequences in a nuclear environment, typically a chromosomal environment. Thus, insulators can enable sustained and/or appropriate regulatory control of sequences integrated into heterologous regions of a chromosome. Chromatin opening elements can protect a gene from gene "silencing" mechanisms.

An insulator sequence can be positioned on either side of the DNA sequence to be transcribed. For example, the insulator can be positioned about 200 bp to about 1 kb, 5' from the promoter, and at least about 1 kb to 5 kb from the promoter, at the 3' end of the gene of interest. In addition, more than one insulator sequence can be positioned 5' from the promoter or at the 3' end of the transgene. For example, two or more insulator sequences can be positioned 5' from the promoter. The insulator or insulators at the 3' end of the transgene can be positioned at the 3' end of the gene of interest, or at the 3' end of a 3' regulatory sequence, e.g., a 3' untranslated region (UTR) or a 3' flanking sequence. Chromatin opening elements can be flanking on one or both ends of the expression cassette, e.g., placed 5' of the expression cassette.

Exemplary insulators include a DNA segment which encompasses the 5' end of the chicken β-globin locus and corresponds to the chicken 5' constitutive hypersensitive site as described in PCT Publication 94/23046, elements described in Bell et al. (2001) Science 291:447-50.

Internal Ribosome Entry Sites (IRES).

IRES enable eukaryotic ribosomes to enter and scan an mRNA at a position other than the 5' $m^7$ G-cap structure. If position internally, e.g., 3' of a first coding region (or cistron), an IRES will enable translation of a second coding region within the same transcript. The second coding region is identified by the first ATG encountered after the IRES. Exemplary IRES elements include viral IRES such as the picornavirus IRES and the cardiovirus IRES (see, e.g., U.S. Pat. No. 4,937, 190) and non-viral IRES elements found in 5' UTRs (e.g., those elements of transcripts encoding immunoglobulin heavy chain binding protein (BiP) (Macejak, D. G., et al. *Nature*, 35390-4, 1991); *Drosophila* Antennapedia (Oh, S. K., et al., *Genes Dev*, 6:1643-53, 1992) and Ultrabithorax (Ye, X., et al., *Mol. Cell Biol.*, 17:1714-21, 1997); fibroblast growth factor 2 (Vagner, S., et al., *Mol. Cell Biol.*, 15:35-44, 1995); initiation factor eIF4G (Gan, et al., *J Biol. Chem.*, 273:5006-12, 1998); proto-oncogene c-myc (Nanbru, et al., *J. Biol. Chem.*, 272:32061-6, 1995; Stoneley, M., Oncogene, 16:423-8, 1998); and vascular endothelial growth factor (VEGF) (Stein, I., et al., *Mol. Cell Biol.*, 18:3112-9, 1998).

Localization Signals.

A "localization signal" is a polypeptide sequence that determines the subcellular localization of polypeptide or protein. The subcellular localization may be: cytoplasmic, nuclear, nuclear envelope, transmembrane, plasma membrane, plasma membrane outer leaflet, endoplasmic reticulum, Golgi, lysosomal, receptor-coated pits, and so forth. For example, the peptide sequence KDEL (SEQ ID NO:32) is an endoplasmic reticulum localization signal and when grafted onto a heterologous protein results in its endoplasmic reticulum localization. A reformatted protein can be localized within a cell by attachment of a localization signal, e.g., a localization signal described by Marasco (2001) *Curr Top Microbiol Immunol.* 260:247-70.

In combination with appropriate flanking sequences, the antibody ligands can be reformatted such that they are expressed as transmembrane proteins on the surfaces of the cells (e.g., lymphocytes) to program the cells to interact with the target recognized by the antibody ligands. In the case of cytotoxic T cells, the ligands may elicit a cytotoxic response against the target. The programmed cytotoxic T cells are tested in vitro or in vivo for cytotoxicity.

Selectable Markers.

The recombinant expression vector includes primary and secondary selectable markers. Primary markers, for example, can be used to select for transformants of mammalian cells. Secondary markers, for example, can be used to select for amplification of the transformed nucleic acid. Exemplary markers include neo, for neomycin or G418 resistance, and HPRT. The choice of selectable markers may depend on the host cell and/or implementation. The DHFR gene, for example, can be used to select for vector amplification by growing cells (e.g., CHO cells) with increasingly stringent methotrexate selection.

Leader Sequences.

Eukaryotic leader sequences are designed for the translocation of nascent polypeptides from ribosomes in the cytoplasm directly into the lumen of the endoplasmic reticulum. Leader sequences, typically hydrophobic, include a sequence that is recognized and cleaved by eukaryotic signal peptidases. The cleavage event produces a mature polypeptide that, absent other signals, is secreted from the cell.

FIG. 8 illustrates a profile for a eukaryotic, gram negative and gram positive leader sequences. Prokaryotes also detect leader sequences which direct translocation of nascent polypeptides into the periplasm. FIG. 8 also illustrates profiles for the signal sequences of Gram negative and positive bacteria.

In some embodiments, the leader sequence includes the sequence VHS (Valine-Histidine-Serine), or VHA (Valine-Histidine-Alanine) at the −3, −2, and −1 positions respectively, where the position after the −1 position is cleaved by signal peptidase. In some instances the same region within the leader sequence may be cleaved by both eukaryotic and prokaryotic processing enzymes, such as is the case for a mutated immunoglobulin leader 'MGWSCIILFLVATATG VHA' (SEQ ID NO:33) sequence, which is functional in mammalian CHO cells, and a mutated M13-pIII derived leader 'VKKLLFAIPLVVPFYSVHA' (SEQ ID NO:34) that is functional in *E. coli*. Such areas of amino acid sequence within a leader can be used to position a restriction enzyme site at the 5' end of a coding sequence to allow expression/secretion-compatible shuttling of coding regions between different expression hosts.

Isolation of Antibody-Expressing Cells

Reformatted nucleic acids are introduced into mammalian host cells, e.g., using conventional transfection techniques, including calcium phosphate or calcium chloride co-precipitation, DEAE-dextran-mediated transfection, lipofection, or electroporation. In addition, biological vectors, e.g., viral vectors can be used as described below. Suitable methods for transforming or transfecting host cells can be found in Sambrook et al., *Molecular Cloning: A Laboratory Manual,* 3rd ed., Cold Spring Harbor Laboratory, (Cold Spring Harbor Laboratory Press, Cold Spring Harbor, N.Y., 2001), and other suitable laboratory manuals. Stable transfected host cells are selected.

Mammalian cells that produce at least a threshold amount of antibody can be isolated by FACS (Fluorescence Activated Cell Sorting). The selection compensates, e.g., for variability in expression levels among cells, allows isolation of cells with high expression levels. At least two types of protocols can be used for antibody production: transient expression protocols and stable expression protocols. FACS selection is typically used to select stable transfected cells.

Transient expression protocols are useful for initial functional testing. Cells, e.g., HekT and COS cells, are transfected with plasmid DNA encoding an individual antibody. The antibody is then purified from the medium in which the cells are grown, e.g., without cell sorting. See, e.g., Example 3.

Stable expression protocols generate stable cell lines which can be amplified for large-scale antibody production. For example, NSO and CHO cells can be used to generate stable cell lines. In some embodiments, stable cell lines for a number of different cell lines is done in batch format. The nucleic acid constructs produced by the batch reformatting are introduced into cells, e.g., by transfection or electroporation. The cells are grown under non-selective conditions, and diluted—to a limited extent. Then selective conditions are applied to select for stable cell lines. Cells that grow are screened by FACS (see below), magnetic particle-based separation, and/or ELISA to identify expressing clones. Such clones, particularly ones that demonstrate high level expression, are expanded and used to produce antibody.

In a related method, stable cell lines are produced by cultivating cells, e.g., CHO cells in suspension, directly in production media (e.g., CHO sera-free medium, e.g. CHO-S-SFM2 from Invitrogen Corp.). These cells are transfected with nucleic acid encoding the desired antibody. Clones isolated from the transformation are used directly for high-density production, e.g., without having to "adapt" the clones to the production medium.

In one embodiment, the cell lines are also engineered to an enzyme that increases the amount of bisected complex oligosaccharides that are added to the Fc region of an antibody. For example, the cell have increased expression of the β-(1, 4)-N-acetylglucosaminyltransferase III enzyme can produce antibodies with improved anti-tumor properties (see, e.g., Umana et al. (1999) *Nature Biotechnol.* 17:176-180).

The method can also include using CHO cells that have been transfected with a vector for expressing whole antibodies. The CHO cells are also modified such that they have the ability to bind antibodies on their cell surface, e.g. by a surface expressed IgG binding protein (e.g. a membrane anchored Fc-Receptor or Protein A). Thus, antibodies produced by the CHO cells are bound to the surface of the cell.

To perform FACS sorting, the transfected and modified CHO cells can be cultured in a low permeability media. The low permeability media can be Phosphate Buffered Saline (PBS) containing about 40% gelatin with or without fetal calf serum. The low permeability media reduces diffusion of the secreted antibodies into the culture, thereby allowing the secreted antibodies to bind to the surface of the CHO cell from which they are expressed rather than diffuse and bind to another cell. The cells are then removed from the low permeability media and exposed to labeled antibodies that selectively bind a portion of the secreted antibody that is not bound to the surface of the cell. The labeled antibody (which binds the secreted antibody) can be conjugated with a fluorophore or a metalisized label. The cells are sorted based on detection of the labeled antibody, e.g., by using fluorescence activated cell sorting (FACS) or magnetic cell sorting, respectively. Using FACS or magnetic cell sorting, the level of antibodies secreted and attached to the CHO cell is detected and those cells which secrete high levels of human antibodies are selected on an individual basis.

With respect to FACS, the cells are sorted using a fluorescent activated cell sorter (e.g., a sorter available from Becton Dickinson Immunocytometry Systems, San Jose Calif.; see also U.S. Pat. Nos. 5,627,037; 5,030,002; and 5,137,809). As each cell passes through the sorter, a laser beam excites fluorescent compounds that may be attached to the cell. A detector assesses the amount of light emitted by such fluorescent compounds, if present. The amount of label bound to each cell is quantified and, if at least a threshold amount of label is detected, an electrostatic field is generated to deflect the cell from its default path. Deflected cells are thus separated and collected. As a result, cells with low or no antibody expression can be discarded and cells that demonstrate high level antibody expression can be harvested and cultured.

A variety of methods can be used to attach secreted antibodies to the expressing cell prior to the detection phase.

In one embodiment, antibody secreted by the transfected cells is chemically attached to the surface of the host cell by a biotin-streptavidin linkage. Turning now to FIG. 13, the host cell which is being assayed for antibody expression is cell-surface biotinylated with sulfo-NHS-LC-biotin or sulfosuccinimidyl-6 (biotinamide) hexanoate. The biotin can also be attached e.g., to sialic acid residues by first adding a ketone, e.g., using N-levulinoyl mannosamine, and then conjugating the ketone to a biotin hydrazide, e.g., biotinamido-caproyl-hydrazide, under physiologic conditions. See, e.g., Both et al., 2001, *Biotechnol. Bioeng* 71, 266-73.

A streptavidin (or avidin) linked moiety such as Protein A-streptavidin is then bound to the cell surface. The moiety includes an antibody capture agent, e.g., Protein A, Protein G or an antibody that recognizes the heavy or light chain of the secreted antibody. The secreted antibodies are thus retained on the cell surface. A conjugated antibody is used detect the retained, secreted antibodies. For example, the conjugate antibody includes a detectable label such as a fluorophore for FACS analysis or a metalisized label for magnetic particle-based separation. A second conjugated antibody used to label human antibodies attached to the cell surface is selected based upon whether an anti-heavy chain or anti-light chain is used as the ligand-antibody. If an anti-heavy chain antibody is used as the capture agent, an anti-light chain antibody is used as the label conjugated antibody. In embodiments that use both the anti-heavy chain and anti-light chain antibodies, only those cells that are secreting whole antibodies are identified. Cells which only express the light chain or only the heavy chain are undetected.

In another embodiment, secreted antibodies are attached to the surface of an expressing cell by a Fc receptor protein. All tester cells include a nucleic acid that directs expression of the Fcy receptor, i.e., the nucleic acid encoding the Fcγ receptor is operably linked to a regulatory sequence that is active in the tester cells or inducible in the tester cells. The Fcγ receptor that is expressed on the cell surface binds to the heavy chain of the antibodies being expressed. The complex is detected by a third antibody, a conjugated antibody specific for the human antibody light chain. For example, the conjugate antibody can include a fluorophore for FACS analysis or a metalisized label for magnetic particle-based separation.

Bioreactors

The antibody expressing cells can be transferred to a high cell density culture system, e.g., a system that produces about 100 mg of antibody using cell densities of about $10^7$ to $10^8$ per ml. In some implementations, it is useful to produce large quantities (e.g., in excess of 100 mg) of a few select antibodies. Likewise, in some other implementations, it is useful to produce smaller quantities (e.g., from 5 mg to 70 mg) of a larger number of antibodies, but still with high yield.

Membrane Technology.

In one embodiment, cells are cultured in a container with "cell line membrane technology" (e.g., from Biointegra.) The container includes at least two compartments which are separated by a semi-permeable membrane. Nutrients and other small molecules can cross the membrane in order to feed cells in the cell compartment. Large molecules, e.g., those with a molecular weight of greater than 10 kDa (such as antibodies) are retained in the cell compartment. The cells in the cell compartment rest on a gas exchange surface which exchanges oxygen and carbon dioxide across its surface. These conditions enable high cell concentrations in a small volume.

Hollow-Fiber Reactor.

In one embodiment, a hollow fiber reactor is used. Such reactors are available from commercial suppliers, e.g., Cellex Bioscience. The reactor includes an extracapillary space and an intracapillary space. The cells are grown in the extracapillary space while medium is circulated through the reactor. Secreted antibody is harvested from the medium as it exits the reactor. See FIG. 15 and Example 5, for an example of human antibody production in a hollow fiber bioreactor. In a related aspect, so-called "artificial kidneys" can be used as bioreactors.

Functional Activity Assays

The antibodies and other mammalian expressed ligands with effector domains can be assayed for functional activity either in vitro or in vivo. Information from cell-based assays can be collected as so-called secondary functional information.

Immunological Assays.

Some functional assays can monitor an activity that depends on an arm of the immune system. Examples include the following.

In vitro assays for immunoglobulin effector domain activity, e.g., cytotoxic activity is used to detect the ability of a ligand to deliver antibody effector functions against a target. For example, cell culture assays can be used to assay complement dependent cytotoxicity (CDC) or antibody-dependent cell-mediated cytotoxicity (ADCC) mediated by a reformatted antibody. One ADCC assay is described below.

The Cr-release assay, for example, can be used to assay cell-mediated cytotoxicity. Peripheral blood lymphocytes (PBL) are prepared as effector cells, while target cells that express the targeted molecule are loaded with $^{51}$Cr. The target cells are washed and then seeded into a flat bottom microtitre plate. PBLs are added to the target cells in combination with the ligand (e.g., a candidate ligand). Maximum release is determined by the addition of Tween-20 to target cells, whereas minimal release is determined in the absence of PBLs. After overnight incubation, $^{51}$Cr released into the supernatant is counted in a K scintillation counter.

In vivo assays include injecting a reformatted antibody into an animal, e.g., an animal model of a diseased state. For example, the animal can be a transgenic animal, e.g., expressing an oncogene in a particular tissue. In another example, the animal is a mouse with a xenograft of tumor cells (e.g., human tumor cells). The efficacy of the antibody (or other ligand) can be assayed by comparing time, size, and number of tumors formed compared to untreated or control-treated animals. In an implementation in which the xenografted mouse is a nude mouse, the mouse can be injected with human PBLs to reconstitute the immune system. Other physiological parameters of the reformatted antibody can also be monitored including immunogenicity, clearance, and so forth.

Cellular Activity Assays.

Other cellular activity assays include assessments of cellular pH and calcium flux, and assessments of a cellular behavior, e.g., apoptosis, cell migration, cell proliferation, and cell differentiation. Assays can monitor a specific response, e.g., activation (such as phosphorylation of a transcription factor such as NKκB, and so forth. Other assays are specific for a particular target compound. Numerous cell culture assays for differentiation and proliferation are known in the art. Some examples are as follows:

Assays for embryonic stem cell differentiation (which will identify, among others, proteins that influence embryonic differentiation hematopoiesis) include, e.g., those described in: Johansson et al. (1995) *Cellular Biology* 15:141-151; Keller et al. (1993) *Molecular and Cellular Biology* 13:473-486; McClanahan et al. (1993) *Blood* 81:2903-2915.

Assays for lymphocyte survival/apoptosis (which will identify, among others, proteins that prevent apoptosis after superantigen induction and proteins that regulate lymphocyte homeostasis) include, e.g., those described in: Darzynkiewicz et al., *Cytometry* 13:795-808, 1992; Gorczyca et al., *Leukemia* 7:659-670, 1993; Gorczyca et al., *Cancer Research*

53:1945-1951, 1993; Itoh et al., *Cell* 66:233 243, 1991; Zacharchuk, *Journal of Immunology* 145:4037 4045, 1990; Zamai et al., Cytometry 14:891-897, 1993; Gorczyca et al., *International Journal of Oncology* 1:639-648, 1992.

Assays for proteins that influence early steps of T-cell commitment and development include, without limitation, those described in: Antica et al., *Blood* 84:111-117, 1994; Fine et al., *Cellular Immunology* 155:111-122, 1994; Galy et al., *Blood* 85:2770-2778, 1995; Toki et al., *Proc. Nat. Acad. Sci. USA* 88:7548-7551, 1991.

Dendritic cell-dependent assays (which will identify, among others, proteins expressed by dendritic cells that activate naive T-cells) include, without limitation, those described in: Guery et al., J. Immunol. 134:536-544, 1995; Inaba et al., Journal of Experimental Medicine 173:549-559, 1991; Macatonia et al., Journal of Immunology 154:5071-5079, 1995; Porgador et al., Journal of Experimental Medicine 182:255-260, 1995; Nair et al., Journal of Virology 67:4062-4069, 1993; Huang et al., Science 264:961-965, 1994; Macatonia et al., Journal of Experimental Medicine 169:1255-1264, 1989; Bhardwaj et al., Journal of Clinical Investigation 94:797-807, 1994; and Inaba et al., Journal of Experimental Medicine 172:631-640, 1990.

Assays for T-cell or thymocyte proliferation include without limitation those described in: Current Protocols in Immunology, Ed by J. E. coligan, A. M. Kruisbeek, D. H. Margulies, E. M. Shevach, W. Strober, Pub. Greene Publishing Associates and Wiley Interscience (Chapter 3, -Tn vitro assays for Mouse Lymphocyte Function 3.1-3.19; Chapter 7, Immunologic studies in Humans); Takai et al., J. Immunol. 137:3494 3500, 1986; Bertagnolli et al., J. Immunol. 145: 1706 1712, 1990; Bertagnolli et al., Cellular Immunology 133:327-341, 1991; Bertagnolli, et al., I. Immunol. 149:3778-3783, 1992; Bowman et al., I. Immunol. 152:1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. Coligan eds. Vol 1 pp. 3.12.1-3.12.14, John Wiley and Sons, Toronto. 1994; and Measurement of mouse and human interleukin gamma., Schreiber, R. D. In Current Protocols in Immunology., Coligan eds. Vol 1 pp. 6.8.1-6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1-6.3.12, John Wiley and Sons, Toronto. 1991; deVries et al., J. Exp. Med. 173:1205 1211, 1991; Moreau et al., Nature 336:690-692, 1988; Greenberger et al., Proc. Natl. Acad. Sci. U.S.A. 80:2931-2938, 1983; Measurement of mouse and human interleukin-6, Nordan, R. In Current Protocols in Immunology. J. E. e.a. Coligan eds. Vol 1 pp. 6.6.1 6.6.5, John Wiley and Sons, Toronto. 1991; Smith et al., Proc. Natl. Aced. Sci. U.S.A. 83:1857-1861, 1986; Measurement of human Interleukin-11, Bennett, F., Giannotti, J., Clark, S. C. and Turner, K. J. In Current Protocols in Immunology. Coligan eds. Vol 1 pp. 6.15.1 John Wiley and Sons, Toronto. 1991;

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Puh. Greene Publishing Associates and Wiley-Interscience (Chapter 3, In vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.

Other assays, for example, can determine biological activity with respect to endothelial cell behavior, nerve cell growth, nerve cell migration, spermatogenesis, oogenesis, apoptosis, endocrine signaling, glucose metabolism, amino acid metabolism, cholesterol metabolism, erythropoiesis, thrombopoeisis, and so forth.

Cell Binding Assays.

The functionality of a reformatted antibody can also be used to in a cell binding assay. The antibody can be labeled bound to a population of cells that includes cells that present a target recognized by the antibody. The population can also include cells that do not present the target, or that present a related molecule that is discriminated by the reformatted antibody.

In a first example, the reformatted antibody is tested using FACS analysis. The reformatted antibody is labeled with a fluorophore, either directly or using a secondary antibody and bound to cells. Then, the cells are passed through a FACS apparatus to count the number of cells bound by the reformatted antibody. The cells can also be contacted with another antibody labeled with a fluorophore that is detectable using a different channel. Binding of this antibody can be correlated on a cell-by-cell basis with binding of the reformatted antibody (e.g., using a 2D scatter plot).

In a second example, the reformatted antibody is assayed using immunohistochemistry. The antibody is contacted to a histological section. The section is washed, and bound antibody is detected, e.g., using standard methods.

In a third example, the reformatted antibody is assayed in vivo, e.g., in a subject organism. The antibody is labeled, e.g., with a NMR contrast reagent or other traceable reagent. The antibody is administered to the subject and, after an appropriate interval, its localization within the subject is detected, e.g., by imaging the subject organism.

Biochemical Assays.

Examples of biochemical assays for testing the functionality of a reformatted antibody include: Western blot analysis, immunoprecipitations, and other binding assays such as surface plasmon resonance (SPR).

SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705.

Information from SPR can be used to provide a quantitative measure of the equilibrium dissociation constant ($K_d$), and kinetic parameters, including $K_{on}$ and $K_{off}$, for the binding of a ligand to a target. Such data can be used to compare different ligands. For example, reformatted antibodies selected from the library can be compared to identify individuals that have high affinity for the target or that have a slow $K_{off}$. This information can also be used to develop structure-activity relationships (SAR).

Affinity Maturation/Optimization

At any stage after initial identification, a selected library member can be mutagenized to improve its binding affinity or any other property. For example, a first display library is used to identify one or more ligands for a target. These identified ligands are then mutated to form a second display library. Higher affinity ligands are then selected from the second library, e.g., by using higher stringency or more competitive binding and washing conditions.

Numerous techniques can be used to mutate the identified ligands. These techniques include: error-prone PCR (Leung et al. (1989) *Technique* 1:11-15), recombination, DNA shuffling using random cleavage (Stemmer (1994) *Nature* 389-391), RACHITT™ (Coco et al. (2001) *Nature Biotech.* 19:354), site-directed mutagenesis (Zoller et al. (1987) Methods Enzymol. 1987; 154:329-50.; Zoller et al. (1982) *Nucl Acids Res* 10:6487-6504), cassette mutagenesis (Reidhaar-Olson (1991) *Methods Enzymol.* 208:564-586) and incorporation of degenerate oligonucleotides (Griffiths et al. (1994) *EMBO J* 13:3245).

For antibodies, mutagenesis can be directed to the CDR regions of the heavy or light chains. Further, mutagenesis can be directed to framework regions near or adjacent to the CDRs. Mutagenesis can introduce synthetic or natural diversity.

Another exemplary method for introducing diversity in a manner guided by the original sequence is the hybridization-directed method described in provisional application 60/343,954, filed Oct. 24, 2001, "HYBRIDIZATION CONTROL OF SEQUENCE VARIATION".

Targets

Targets.

Generally, any molecular species can be used as a target. In some embodiment, more than one species is used as a target, e.g., a sample is exposed to a plurality of targets. The target can be of a small molecule (e.g., a small organic or inorganic molecule), a polypeptide, a nucleic acid, cells, and so forth.

One class of targets includes polypeptides. Examples of such targets include small peptides (e.g., about 3 to 30 amino acids in length), single polypeptide chains, and multimeric polypeptides (e.g., protein complexes).

A polypeptide target can be modified, e.g., glycosylated, phosphorylated, ubiquitinated, methylated, cleaved, disulfide bonded and so forth. Preferably, the polypeptide has a specific conformation, e.g., a native state or a non-native state. In one embodiment, the polypeptide has more than one specific conformation. For example, prions can adopt more than one conformation. Either the native or the diseased conformation can be a desirable target, e.g., to isolate agents that stabilize the native conformation or that identify or target the diseased conformation.

In some cases, however, the polypeptide is unstructured, e.g., adopts a random coil conformation or lacks a single stable conformation. Agents that bind to an unstructured polypeptide can be used to identify the polypeptide when it is denatured, e.g., in a denaturing SDS-PAGE gel, or to separate unstructured isoforms of the polypeptide for correctly folded isoforms, e.g., in a preparative purification process.

Some exemplary polypeptide targets include: cell surface proteins (e.g., glycosylated surface proteins or hypoglycosylated variants), cancer-associated proteins, cytokines, chemokines, peptide hormones, neurotransmitters, cell surface receptors (e.g., cell surface receptor kinases, seven transmembrane receptors, virus receptors and co-receptors, extracellular matrix binding proteins such as integrins, cell-binding proteins (e.g., cell attachment molecules or "CAMs" such as cadherins, selectins, N-CAM, E-CAM, U-CAM, I-CAM and so forth), or a cell surface protein (e.g., of a mammalian cancer cell or a pathogen). In some embodiments, the polypeptide is associated with a disease, e.g., cancer.

The target polypeptide is preferably soluble. For example, soluble domains or fragments of a protein can be used. This option is particularly useful for identifying molecules that bind to transmembrane proteins such as cell surface receptors and retroviral surface proteins.

Some exemplary targets include: cell surface proteins (e.g., glycosylated surface proteins or hypoglycosylated variants), cancer-associated proteins, cytokines, chemokines, peptide hormones, neurotransmitters, cell surface receptors (e.g., cell surface receptor kinases, seven transmembrane receptors, virus receptors and co-receptors, extracellular matrix binding proteins, cell-binding proteins, antigens of pathogens (e.g., bacterial antigens, malarial antigens, and so forth).

More specific examples include: integrins, cell attachment molecules or "CAMs" such as cadherins, selections, N-CAM, E-CAM, U-CAM, I-CAM and so forth); proteases, e.g., subtilisin, trypsin, chymotrypsin; a plasminogen activator, such as urokinase or human tissue-type plasminogen activator (t-PA); bombesin; factor IX, thrombin; CD-4; CD-19; CD20; platelet-derived growth factor; insulin-like growth factor-I and -II; nerve growth factor; fibroblast growth factor (e.g., aFGF and bFGF); epidermal growth factor (EGF); transforming growth factor (TGF, e.g., TGF-α, and TGF-β); insulin-like growth factor binding proteins; erythropoietin; thrombopoietin; mucins; human serum albumin; growth hormone (e.g., human growth hormone); proinsulin, insulin A-chain insulin B-chain; parathyroid hormone; thyroid stimulating hormone; thyroxine; follicle stimulating hormone; calcitonin; atrial natriuretic peptides A, B or C; leutinizing hormone; glucagon; factor VIII; hemopoietic growth factor; tumor necrosis factor (e.g., TNF-α, and TNF-β); enkephalinase; mullerian-inhibiting substance; gonadotropin-associated peptide; tissue factor protein; inhibin; activin; vascular endothelial growth factor; receptors for hormones or growth factors; protein A or D; rheumatoid factors; osteoinductive factors; an interferon, e.g., interferon-α,β,γ; colony stimulating factors (CSFs), e.g., M-CSF, GM-CSF, and G-CSF; interleukins (ILs), e.g., IL-1, IL-2, IL-3, IL-4, etc.; decay accelerating factor; immunoglobulin (constant or variable domains); and fragments of any of the above-listed polypeptides. In some embodiments, the target is associated with a disease, e.g., cancer.

Cells as Targets.

Another class of targets includes cells, e.g., fixed or living cells. The cell can be bound to an antibody that is covalently attached to a paramagnetic particle or indirectly attached (e.g., via another antibody). For example, a biotinylated rabbit anti-mouse Ig antibody is bound to streptavidin paramagnetic beads and a mouse antibody specific for a cell surface protein of interest is bound to the rabbit antibody.

In one embodiment, the cell is a recombinant cell, e.g., a cell transformed with a heterologous nucleic acid that expresses a heterologous gene or that disrupts or alters expression of an endogenous gene. In another embodiment, the cell is a primary culture cell isolated from a subject, e.g., a patient, e.g., a cancer patient. In still another embodiment, the cell is a transformed cell, e.g., a mammalian cell with a cell proliferative disorder, e.g., a neoplastic disorder. In still another embodiment, the cell is the cell of a pathogen, e.g., a microorganism such as a pathogenic bacterium, pathogenic fungus, or a pathogenic protist (e.g., a *Plasmodium* cell) or a cell derived from a multicellular pathogen.

Cells can be treated, e.g., at a particular stage of the washing step. The treatment can be a drug or an inducer of a heterologous promoter-subject gene construct. The treatment can cause a change in cell behavior, morphology, and so forth. Molecules that dissociate from the cells upon treatment are collected and analyzed.

Examples of cells include, a cancer cell, a hematopoietic cell, Ball cells, primary culture cells, malignant cells, neuronal cells, embryonic cells, placental cells, and non-mammalian cells (e.g., bacterial cells, fungal cells, plant cells) and so forth. Cancer cells, for example, are attached to magnetically responsive particles using an antibody specific for a marker on the cell surface, e.g., CD19 or a cell-surface cancer-specific antigen.

In a preferred embodiment, the cells are recombinant cells. The cells can be transformed with a plasmid that expresses (e.g., under control of an inducible or constitutive promoter) a cell-surface protein of interest. The plasmid can also express a marker protein, e.g., for use in binding the transformed cell to a magnetically responsive particle. In another embodiment, the cells express an intracellular protein, e.g., an oncogene, transcription factor, or cell-signaling protein. The intracellular protein can alter cell behavior or the repertoire of molecules on the cell surface. In still another embodiment, the cells are treated (e.g., using a drug or genetic alteration) to alter the rate of endocytosis, pinocytosis, exocytosis, and/or cell secretion.

Still more exemplary targets include organic molecules. In one embodiment, the organic molecules are transition state analogues and can be used to select for catalysts that stabilize a transition state structure similar to the structure of the analogue. In another embodiment, the organic molecules are suicide substrates that covalently attach to catalysts as a result of the catalyzed reaction.

Effector Domains

Effector domains can be attached to the antibody ligand during the reformatting process. One exemplary effector domain is a polypeptide that includes an immunoglobulin constant region, e.g., an Fc domain.

Fc Domains.

As discussed above, Fc domains mediate effector functions by recruiting C1q for complement-dependent cytotoxicity (CDC) and FcγRs for ADCC.

The Fc region of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) *Adv. Immunol.* 51:1-84; Jefferis et al. (1998) *Immunol. Rev.* 163:59-76). In a preferred embodiment, the Fc domain is produced in a mammalian expression system that appropriately glycosylates the residue corresponding to asparagine 297 (Kabat numbering). The Fc domain can also include other eukaryotic modifications.

The Fc domain can be attached to the hinge region, which is found between CH1 and CH2 of antibody heavy chains. The hinge region can impart a flexible structure that facilitates the recruitment of effector functions which bind in the CH2 domain in the proximity of the hinge region and also, e.g., antigen aggregation by a second antigen binding domain.

In one embodiment, the Fc domain is a modified Fc domain. For example, the Fc domain can be altered, e.g., such that it has altered binding properties (e.g., enhanced or diminished). For example, the Fc domain can be engineered to preferentially binding to some Fc receptors relative to others.

Shields et al. (2001) *J Biol Chem* 276:6591-6604 describes a variant IgG 1 Fc domain that has improved binding to FcγRIIIA Idusogie et al. (2000) *J. Immunol.* 164:4178 describes an IgG1 mutant that alters C1q binding and complement activation.

In still another embodiment, the effector domain is a synthetic polypeptide that binds to an Fc receptor or to complement. Such synthetic polypeptides can be identified by a phage display selection for 6 to 20 amino acid cyclic peptides that specifically binding to one species of Fc receptor, but not another.

Non-Immunological Effector Domains.

In some embodiments, non-immunological effector domains, including effector domains composed of polypeptides and polypeptide conjugates. Examples of such effector domains include the following labels and cytotoxins.

Labels.

For example, the effector fragment can include a polypeptide label or a non-polypeptide label. Polypeptide labels include enzymes, such as horseradish peroxidase, alkaline phosphatase, β-galactosidase, or acetylcholinesterase. Other polypeptide labels include luciferase, luciferin, aequorin, and green fluorescent protein (and its derivatives). For example, an effector domain fragment that includes GFP can be used to identify the localization of a target in a sample, e.g., a histological sample.

Cytotoxins.

Polypeptide and non-polypeptide cytotoxins can be used as an effector domain. Examples of polypeptide cytotoxins include diphtheria toxin, cholera toxin, abrin, pseudomonas exotoxin, and ricin A.

Display Libraries

A display library is a collection of entities; each entity includes an accessible polypeptide component and a recoverable component that encodes or identifies the polypeptide component. The polypeptide component can be of any length, e.g. from three amino acids to over 300 amino acids. In some embodiments, the ligand discovery platform described herein uses a display library as a diverse source of potential ligands.

A variety of formats can be used for display. The following are some examples.

Phage Display.

One format utilizes viruses, particularly bacteriophages. This format is termed "phage display." The polypeptide component is typically covalently linked to a bacteriophage coat protein. The linkage results form translation of a nucleic acid encoding the polypeptide component fused to the coat protein. The linkage can include a flexible peptide linker, a protease site, or an amino acid incorporated as a result of suppression of a stop codon. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982.

Phage display systems have been developed for filamentous phage (phage fl, fd, and M13) as well as other bacteriophage (e.g. T7 bacteriophage and lambdoid phages; see, e.g., Santini (1998) *J. Mol. Biol.* 282:125-135; Rosenberg et al. (1996) *Innovations* 6:1-6; Houshmand et al. (1999) *Anal Biochem* 268:363-370). The filamentous phage display systems typically use fusions to a minor coat protein, such as gene III protein, and gene VIII protein, a major coat protein, but fusions to other coat proteins such as gene VI protein, gene VII protein, gene IX protein, or domains thereof can also been used (see, e.g., WO 00/71694). In a preferred embodiment, the fusion is to a domain of the gene III protein, e.g., the anchor domain or "stump."

The valency of the polypeptide component can also be controlled. Cloning of the sequence encoding the polypeptide component into the complete phage genome results in multi-variant display since all replicates of the gene III protein are fused to the polypeptide component. For reduced valency, a phagemid system can be utilized. In this system, the nucleic acid encoding the polypeptide component fused to gene III is provided on a plasmid, typically of length less than 700 nucleotides. The plasmid includes a phage origin of replication so that the plasmid is incorporated into bacteriophage particles when bacterial cells bearing the plasmid are infected with helper phage, e.g. M13K01. The helper phage provides an intact copy of gene III and other phage genes required for phage replication and assembly. The helper phage has a defective origin such that is the helper phage genome is not efficiently incorporated into phage particles relative to the plasmid that has a wild type origin.

Bacteriophage displaying the polypeptide component can be grown and harvested using standard phage preparatory methods, e.g. PEG precipitation from growth media.

After selection of individual display phages, the nucleic acid encoding the selected polypeptide components, by infecting cells using the selected phages. Individual colonies or plaques can be picked, the nucleic acid isolated and sequenced.

Peptide-Nucleic Acid Fusions.

Another format utilizes peptide-nucleic acid fusions. Polypeptide-nucleic acid fusions can be generated by the in vitro translation of mRNA that include a covalently attached puromycin group, e.g., as described in Roberts and Szostak (1997) *Proc. Natl. Acad. Sci. USA* 94:12297-12302, and U.S. Pat. No. 6,207,446. The mRNA can then be reverse transcribed into DNA and crosslinked to the polypeptide.

Cell-Based Display.

In still another format the library is a cell-display library. Proteins are displayed on the surface of a cell, e.g., a eukaryotic or prokaryotic cell. Exemplary prokaryotic cells include *E. coli cells, B. subtilis* cells, spores (see, e.g., Lu et al. (1995) *Biotechnology* 13:366). Exemplary eukaryotic cells include yeast (e.g., *Saccharomyces cerevisiae, Schizosaccharomyces pombe, Hanseula,* or *Pichia pastoris*). Yeast surface display is described, e.g., in Boder and Wittrup (1997) *Nat. Biotechnol.* 15:553-557 and U.S. Provisional Patent Application No. Ser. No. 60/326,320, filed Oct. 1, 2001, titled "MULTI-CHAIN EUKARYOTIC DISPLAY VECTORS AND THE USES THEREOF." This application describes a yeast display system that can be used to display immunoglobulin proteins such as Fab fragments, and the use of mating to generate combinations of heavy and light chains.

In one embodiment, variegate nucleic acid sequences are cloned into a vector for yeast display. The cloning joins the variegated sequence with a domain (or complete) yeast cell surface protein, e.g., Aga2, Aga1, Flo1, or Gas1. A domain of these proteins can anchor the polypeptide encoded by the variegated nucleic acid sequence by a transmembrane domain (e.g., Flo1) or by covalent linkage to the phospholipid bilayer (e.g., Gas1). The vector can be configured to express two polypeptide chains on the cell surface such that one of the chains is linked to the yeast cell surface protein. For example, the two chains can be immunoglobulin chains.

Ribosome Display.

RNA and the polypeptide encoded by the RNA can be physically associated by stabilizing ribosomes that are translating the RNA and have the nascent polypeptide still attached. Typically, high divalent $Mg^{2+}$ concentrations and low temperature are used. See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30. and Schaffitzel et al. (1999) *J Immunol Methods.* 231(1-2):119-35.

Other Display Formats.

Yet another display format is a non-biological display in which the polypeptide component is attached to a non-nucleic acid tag that identifies the polypeptide. For example, the tag can be a chemical tag attached to a bead that displays the polypeptide or a radiofrequency tag (see, e.g., U.S. Pat. No. 5,874,214).

Scaffolds.

One typical scaffold for ligand discovery is an antibody (e.g., Fab fragments, single chain Fv molecules (scFV), single domain antibodies, camelid antibodies, and camelized antibodies). However, aspects of the ligand discovery platform described herein can be applied to the discovery of ligands that depend on other types of scaffolds for a structural framework.

Another example of a small scaffolding domain is a so-called "cysteine loop" formed by a pair of cysteines separated by amino acids, e.g., between three and 25 amino acids, or between four and ten amino acids. The intervening amino acids can be any amino acid other than cysteine, in which case, under oxidizing conditions, the pair of cysteines disulfide bond and constrain the topology of the intervening amino acids. Randomized short linear peptides, e.g., between four and 25 amino acids, or between four and 15 amino acids, can also be used.

Still other exemplary scaffolds can include: T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins.

Appropriate criteria for evaluating a scaffolding domain can include: (1) amino acid sequence, (2) sequences of several homologous domains, (3) 3-dimensional structure, and/or (4) stability data over a range of pH, temperature, salinity, organic solvent, oxidant concentration. In one embodiment, the scaffolding domain is a small, stable protein domains, e.g., a protein of less than 100, 70, 50, 40 or 30 amino acids. The domain may include one or more disulfide bonds or may chelate a metal, e.g., zinc.

Examples of small scaffolding domains include: Kunitz domains (58 amino acids, 3 disulfide bonds), *Cucurbida maxima* trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fungal carbohydrate-binding domains (35 amino acids, 2 disulfide bonds), endothelin domains (18 amino acids, 2 disulfide bonds), Streptococcal G IgG-binding domain (35 amino acids, no disulfide bonds) and small intracellular signaling domains such as SH2, SH3, and EVH domains. Generally, any modular domain, intracellular or extracellular, can be used.

Further display technology can also be used to obtain ligands that are particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Automated Methods and Information Management

Any and all aspects of the ligand identification platform can be automated. Referring now to FIG. 14, information, particularly functional information and tracked events associated with ligand discovery is stored in a central database 260. For example, the database 260 can include primary functional information 230 (such as data on binding properties from ELISAs) as well as secondary functional information 250 (such as data on ADCC activity of a mammalian cell-expressed ligand). Instances of each datum are associated with instances of library members.

The database server 260 can also track events associated with: the initial selection of library members for binding to a target; sample handling of library nucleic acids that are being advanced for reformatting 240; expression levels of library members in mammalian cells; and functional activity of proteins (e.g., 250) isolated from mammalian expression systems.

The automation and information management strategies enable the rapid screening of numerous individual library members and then winnow these to a more limited number of ligands. In some cases, the use of automation to perform the selection increases the reproducibility of the selection process as well as the through-put. Further, the cohesive and highly refined monitoring enables operators to finely tune the discovery process.

After selecting a pool of target binding members from a display library, the identified members of the pool are individually isolated using a robotic device. Referring now to FIG. 15 and FIG. 16, for a phage display library, for example, the pool can be infected into bacterial cells which are then plated 316 at a density such that individual colonies or plaques are formed from each infection event. The individual colonies are picked 320 into wells of a multi-well plate, e.g., a 94- or 364-well plate, using an automated colony picker. Typically, the colonies are picked in duplicate, e.g., into corresponding wells of two identical plates. One of the plates is archived. The other can be used as a source for subsequent analyses.

Automated picking enables the picking of at least 100, $10^3$, $10^4$, $10^5$ (or more) selected library members. Each of these library members can then by analyzed individually as described below. Information about the picking can be stored in the database, e.g., using cross-referenced records for, respectively, the plate, each well, and each display library member.

Assays.

Referring again to FIG. 15 and FIG. 16, the individual library members are analyzed using an assay 324, typically a high through-put assay. The assay determines functional information for the polypeptide component being displayed for each library member. The functional information can be obtained for the polypeptide component when it is either attached or removed from the library vehicle, e.g., the bacteriophage. The functional information is recorded in the database 60 in a table of assay results. Each entry in the table includes a field that points to the display library member being assayed and another field that stores the result of the assay, and other relevant information such as background levels, and results for controls. A variety of possible assays, including binding assays (such as ELISAs) can be used to obtain functional information about binding.

Equipment.

Various robotic devices can be employed in the automation process. These include multi-well plate conveyance systems, magnetic bead particle processors, liquid handling units, and colony picking units.

These devices can be built on custom specifications or purchased from commercial sources, such as Autogen (Framingham Mass.), Beckman Coulter (USA), Biorobotics (Woburn Mass.), Genetix (New Milton, Hampshire UK), Hamilton (Reno Nev.), Hudson (Springfield N.J.), Labsystems (Helsinki, Finland), Packard Bioscience (Meriden Conn.), and Tecan (Mannedorf, Switzerland).

The database server 260 can also be configured to communicate with each device using commands and other signals that are interpretable by the device. The computer-based aspects of the system can be implemented in digital electronic circuitry, or in computer hardware, firmware, software, or in combinations thereof. An apparatus of the invention, e.g., the database server 260, can be implemented in a computer program product tangibly embodied in a machine-readable storage device for execution by a programmable processor; and method actions can be performed by a programmable processor executing a program of instructions to perform functions of the invention by operating on input data and generating output. One non-limiting example of an execution environment includes computers running Windows NT 4.0 (Microsoft) or better or Solaris 2.6 or better (Sun Microsystems) operating systems.

Viral Vectors for Expression

In one embodiment, nucleic acids encoding the ligands are reformatted by incorporation into a viral vector for viral-base delivery into cells in culture or in a subject organism. Viral vector systems include those of DNA and RNA viruses, e.g., retroviruses, lentiviruses, adenoviruses, and herpes simplex viruses. Adeno-associated virus, lenti virus, and retroviral systems enable integration of the nucleic acid encoding the ligands into a chromosome.

Viruses the incorporate the reformatted nucleic acids encoding ligands can be used to generated target-directed cytotoxic T cells. For example, viruses with tropism for lymphoid cells are prepared as vectors and used to infect cytotoxic T lymphocytes. For example, plasma membrane associated antibody ligands can be expressed in the T lymphocytes.

Reformatting for Yeast Display Libraries

Figure 19:
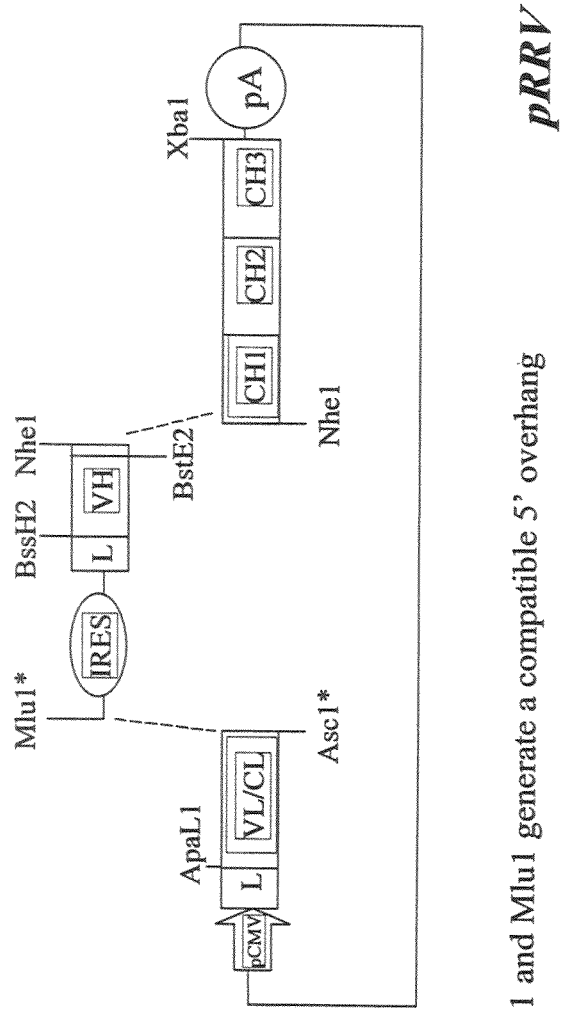

In another embodiment, a yeast display library that encodes heteromultimeric ligands, such as antibodies (e.g., Fabs) is produced by reformatting a phage display library. Again, the process can be performed en masse. Referring to FIG. 19, the ApaL1 to NotI fragment of the phage display vector is inserted into a yeast display library vector. The fragment contains sequences encoding VL and CL, for the light chain, a sequence encoding a leader sequence, VH, CH, and a myc tag, for the heavy chain. A prokaryotic ribosomal binding site is located between the AscI and SfiI sites as is the sequence encoding the leader for the heavy chain. Insertion of the ApaL1-NotI fragment into a yeast display vector positions the yeast GAL1 promoter and a sequence encoding a yeast leader sequence (i.e., signal sequence) and an anchor protein (such as Aga2p or a fragment thereof) 5' of the coding strand of the fragment and a myc tag and stop codon C-terminal.

The segment intervening between the light and heavy chain coding regions is then substituted by removing the prokaryotic ribosomal binding site and leader sequence and inserting a sequence that includes a stop codon, the yeast GAL1 promoter, a yeast leader sequence, and a sequence encoding an anchor protein (such as Aga2p or fragment thereof). The yeast leader sequence can also be the signal peptide of Aga2p. Aga2p is a subunit of the a-agglutinin protein). The reformatting locates the anchor protein at the N-terminus of both subunits and results in two transcriptional units operably linked to yeast promoters.

Yeast display library members can also be reformatted for expression in a phage display vector, e.g., by reversing the steps described above. See also U.S. Provisional Patent Application Ser. No. 60/326,320, filed Oct. 1, 2001, titled "MULTI-CHAIN EUKARYOTIC DISPLAY VECTORS AND THE USES THEREOF."

Further, yeast display library members can be reformatted for expression in mammalian cells. The ApaL1-Not fragment from the yeast vector is transferred into pBRV. Then, an AscI-SfiI or AscI-MfeI fragment is substituted to insert an IRES or a mammalian promoter, such as the CMV promoter. The reformatting also removes the N-terminal Aga2p anchor protein so that antibodies produced in mammalian cells have a native N-terminus or a short peptide addition at the N-terminus (e.g., 6 residues or less).

Reformatting scFV Coding Sequences

A library of nucleic acids encoding scFv antibodies can be reformatted as sequences encoding Fabs or even complete IgG antibodies using the methods described herein. Unique restriction enzyme sites are positioned 5' and 3' of the sequence encoding the linker between the VL and VH domains in the scFv on the coding strand. First the nucleic acid fragment that includes the sequences encoding the VL and VH domain and the intervening linker are transferred to a Fab expression vector or mammalian expression vector. For the example above, a Fab expression vector includes a sequence encoding the CH1 domain so that the VH encoding sequence is inserted immediately 5', with respect to the coding strand, to form a sequence encoding VH-CH1. Then the unique restriction sites flanking the intervening sequence are used to replace the sequence encoding the peptide linker with a fragment that includes a sequence encoding a CL domain, a stop codon, and any necessary intervening regulatory sequences such as a prokaryotic ribosome binding site, an IRES, a eukaryotic promoter, and/or an eukaryotic leader sequence.

This reformatting process can also be reversed. The expression of scFv antibodies can be useful, for example, in expression systems susceptible to non-stoichiometric production of heavy and light chains or poor association of the heavy and light chains.

Still other reformatting applications may be relevant. For example, antibody encoding sequences can be reformatted for expression in plants, e.g., using plant virus (such as the Cauliflower Mosaic Virus) promoters, and a plant signal sequences. See, e.g., U.S. Pat. No. 6,080,560.

The following invention is further illustrated by the following examples, which should not be construed as further limiting. The contents of all references, pending patent applications and published patents, cited throughout this application are hereby expressly incorporated by reference. This provisional application also includes an Appendix which is an integral component of the application, and accordingly the Appendix incorporated in its entirety.

Example 1

Restriction-Based Shuttling of Fab Cassettes Between Bacterial and Mammalian Expression Vectors Bacterial and mammalian expression vectors were prepared that support the transfer individually or en masse of Fab heavy and light chain genes from a bacterial expression vector to a mammalian expression vector while maintaining linkage between paired heavy and light chain genes.

Figure 2:
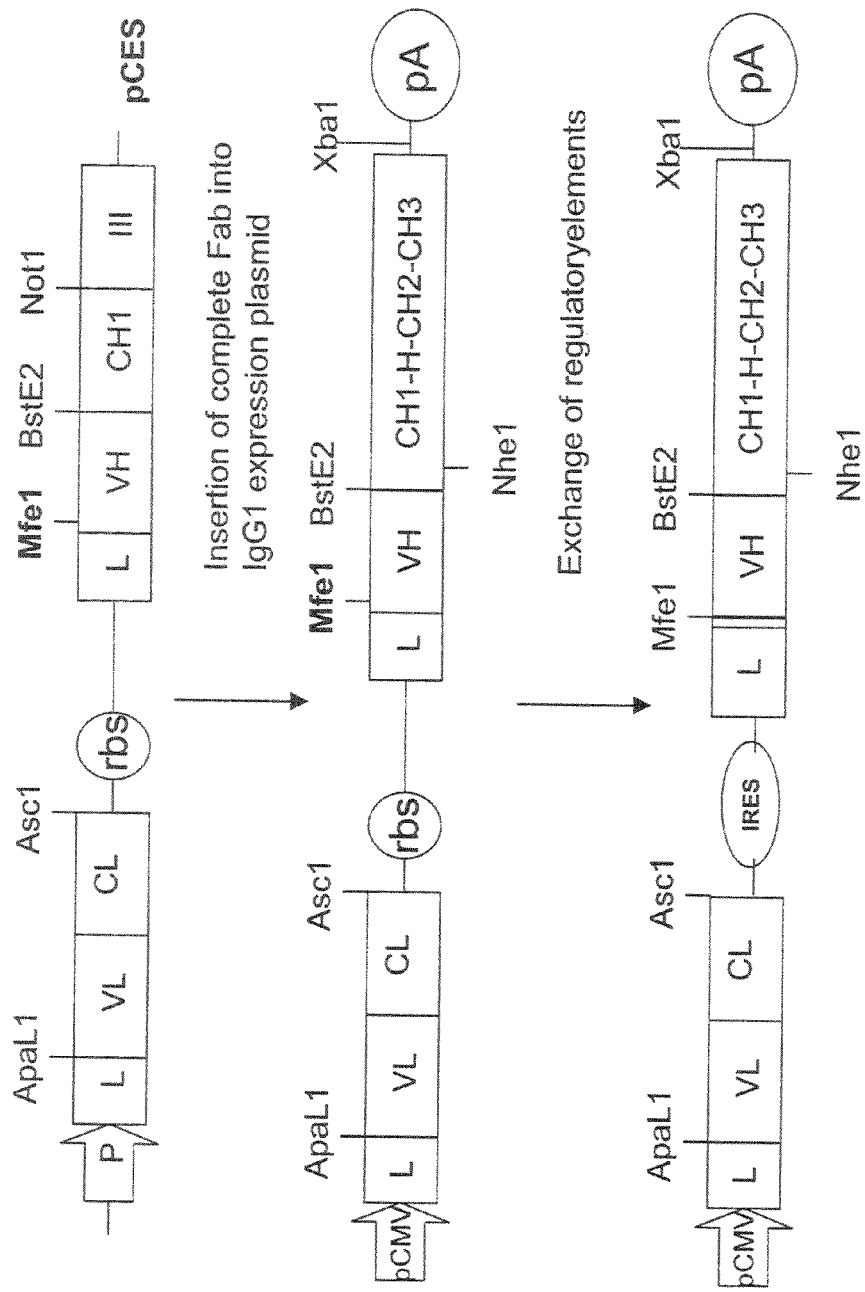
FIG. 2 is a reformatting scheme for en masse transfer of Fabs to the pBRV expression vector. (Top) Organization of display vector: prokaryotic promoter (LacZ), bacterial ribosomal binding site (this one not shown), M13 geneIII leader, LC coding region (ApaL1/Asc1 fragment), bacterial ribosome binding site (rbs), PelB leader, VH coding sequence (inserted as SfiI/BstE2 fragment), and M13 geneIII coding sequence (fused in frame).

Referring to FIG. 2 (top), the Fab expression cassette of a display vector that serves as a source of Fab genes for reformatting (top), can include the following elements: a bacterial promoter (P), followed by a bacterial leader sequence (L) which in turn is followed by cloning sites, including ApaL1, AscI, MfeI, BstEII, and NotI. Sequences encoding an immunoglobulin light chain (VL and CL) are inserted between the ApaL1 and AscI sites. These sequences are followed by a stop codon (not shown), a bacterial ribosomal binding site (rbs), and a second leader sequence (L). The MfeI site is positioned in the FR1 region of an antibody variable region encoding sequence and downstream of the leader sequence. Sequences encoding an immunoglobulin heavy chain fragment (VH and CH1) are inserted between the MfeI and NotI sites. Alternatively, sequences encoding an immunoglobulin heavy chain fragment (VH) are inserted between the MfeI and BstEII sites. These sequences are in frame with a sequence encoding a filamentous bacteriophage gene III coat protein (III). The display vector also contains selectable markers and origins of replication (not shown).

Typically, the display vector is a phagemid or phage display vector, which mediate the expression of the Fab on the surface of the bacteriophage M13 or fd. The Fab-encoding segment is transferred from the bacterial display vector to the eukaryotic vector, e.g., pBRV or pRRV (FIG. 3) by restricting the vector with ApaL1 and BstE2. This fragment is subcloned into ApaL1/BstE2 sites of pBRV or pRRV. Alternatively, if the Fab cassette also carries a unique NheI site within the CH1 domain, the cloning can be done via this site instead of BstEII. This vector contains a CMV eukaryotic promoter in place of the bacterial promoter, and a eukaryotic leader sequence in place of the first bacterial leader sequence. The VH-CH1 sequence is no longer fused to gene III but is fused in-frame to a sequence encoding an immunoglobulin Fc region, e.g., including Hinge-CH2-CH3. This construction encodes a full length IgG heavy chain. The vector also includes a selectable neomycin resistance gene and sequences for maintenance in bacteria (see FIG. 3).

The bacterial RBS is replaced with a eukaryotic IRES by restricting the vector with AscI and MfeI and replacing the excised fragment (which includes the bacterial RBS) with a fragment that includes the IRES and a second eukaryotic leader sequence is inserted. This vector is transformed into a eukaryotic host and the encoded complete antibody is assayed for functional activity.

pBRV and pRRV are related vectors that differ in the position and reading frame of the ApaL1 at the 3' end of the leader driving light chain secretion. Antibody genes transferred to pBRV in two restriction-cloning steps encode antibodies that include an additional alanine residue at the N-terminus of VL after processing. Antibody genes transferred to pRRV in a procedure in which the Fab fragment is excised from their source display construct by PCR, have an N-terminus that is unaltered relative a naturally-occurring VL.

Example 2

Leader Sequences

Referring to FIG. 4, two possible intervening segments which can be inserted between heavy and light chain coding sequences are depicted. Both segments include an IRES between the EcoRI and XbaI site for internal ribosome entry and translation of the second coding region. One intervening segment, from pblue (top), includes the R27080 leader, MARRLWILSLLAVTLTVALAEVQL (SEQ ID NO:1). Cleavage of this leader sequence follows the final alanine and releases a mature N-terminus that begins with EVQL (SEQ ID NO:3). The other, from pRRV, includes an antibody leader sequence, MGWSCIILFLVATATGAHSEVQL (SEQ ID NO:2). This leader sequence is cleaved after the final serine and releases a mature N-terminus that begins with EVQL (SEQ ID NO:3).

Example 3

PCR-Based Shuttling of Fab Cassettes Between Bacterial and Mammalian Expression Vectors The Fab genes in bacterial expression constructs are amplified with designed PCR primers that include suitable restriction enzyme recognition sites at positions compatible for transfer, e.g., at the border of V genes. The amplified PCR products are digested with ApaL1 and NheI and cloned into the pRRV vector, digested with ApaL1 and Nhe. A second step is used to replace the region between the heavy and light chain genes with a eukaryotic IRES and eukaryotic leader sequence. Expression of the antibodies from the pRRV vector results in production of full-length antibodies that include an N-terminus that is unaltered relative to a naturally-occurring VL.

Example 4

Transient Expression

For a given target, twenty Fabs are identified from a display library. These Fabs are reformatted into IgG form. Each IgG is expressed and purified to obtain about 200 μg to 500 μg of antibody. The process involves: batch transfer, re-identification of initial Fabs, transient expression of individual clones, and purification.

Each IgG is expressed by, transient expression in HekT cells grown in ten 10 cm diameter culture dishes. For each IgG, about 100 ml to 200 ml conditioned culture media are obtained. Each IgG is purified from the harvested media.

The method described can be up-scaled for production of up to 10 mgs of antibody. In addition, other methods, based on transient transfection of cells grown at high cell density in bioreactors using viral or non-viral vectors (Curr Opin Biotechnol 1999 April; 10(2):156-9), can be used. Expression levels of >20 mg/liter have been described for Hek293 cells, grown in 1-3 liter bioreactors and transfected with an expression construct of a human IgG1 by Ca-phosphate-DNA co-precipitate technology (*Biotechnol Bioeng* (2001)75:197-203).

Example 5

Isolation of High Expressing Cells from a Pool of Stable Transfectants Using Stable clones of antibody expressing cells are isolated as follows. Cells transfected with antibody expression constructs are grown in a medium of low permeability. The antibodies that they express are captured at the surface of the secreting cell. These captured antibodies are detected on the surface associated soluble antibody with a fluorescent dye conjugated secondary reagent. The sample (i.e., the cell pool) is analyzed in a flow cytometer and sorted to isolate the sub-population (1-5% of cells) with highest expression levels.

This subpopulation can be subjected to one or more cycles of sorting and/or cultivated to establish clonal cell lines that produce high levels of antibody expression.

Applications of the method are as follows:
1. isolation of high expressing cells from a pool of cells transfected with an individual IgG construct;
2. isolation of high expressing cells for many different IgG antibodies from a pool of cells transfected with a mixture of constructs (i.e., constructs for the different IgG antibodies); and
3. isolation of high(er) expressing cells obtained by methotrexate amplification of IgG constructs in CHO dhfr- cells (e.g., as described in Borth et al. (2001) *Biotechnol. Bioeng.* 71:266-73

Example 6

The term "CJ library" refers to an exemplary naïve library.

This example describes tools and strategies for reformatting of Fabs to whole human IgG antibodies. The reformatting vectors are compatible with a number of antibody display libraries; the strategies allow, e.g., fast reformatting of Fabs to IgGs.

These reformatting strategies can be used for the fast assembly of a mammalian expression vector (FIG. 6 depicts pRRV), for simultaneous expression of both chains of a human IgG antibody. Light chain (LC) and heavy chain (HC) expression are under control of the same promoter, the two "open reading frames" are linked via an "internal ribosome entry site" (IRES). Besides the antibody expression cassette, the construct contains the neomycin resistance gene as selectable marker for generation of stable cell lines. The SV40 origin of replication allows amplification of the vector in SV40 transformed (SV40 large T antigen expressing) cells, thereby facilitating increased antibody expression levels in transient expression systems, in e.g. HekT cells.

pRRV, the preferentially used expression vector for reformatted CJ Fabs is shown in FIG. 6.

Two exemplary approaches include: a) reformatting of Fab fragments from the display vector/phage into the eukaryotic expression vector pBRV can be done by restriction endonuclease/enzyme cloning; and b) reformatting of Fab fragments from the display vector/phage into the eukaryotic expression vector pRRV by a PCR based strategy.

Reformatting into pBRV (Batch Reformatting Vector):

Due to compatibility of restriction sites in the display constructs and pBRV, the transfer of Fabs can be performed solely by restriction fragment cloning ("cut and paste"). Besides reformatting of an individual Fab, it is also possible to batch transfer (see below) Fab fragments derived from a mixture of simultaneously propagated (e.g., without PCR) phages/phagemids. After a "cut and paste" transfer of Fabs into pBRV, it is not necessary to verify the complete DNA sequence of the "whole antibody" constructs obtained, since no PCR step has been involved.

Reformatting into pRRV (Rapid Reformatting Vector):

For reformatting of individual Fabs to "unaltered" antibodies a PCR based strategy can be used. Unmodified human IgG antibodies with "natural" N-termini are obtained. A verification of the complete DNA sequence is required, after reformatting. Reformatting of Fabs from a "non-CJ" library requires the design of two V gene specific primers for each individual clone. In case of the CJ library a very small number of PCR primers is sufficient for amplification of virtually all Fabs present in the library. It is also possible to batch transfer Fabs from the CJ library to unaltered human antibodies.

Batch reformatting is the simultaneous transfer of a Fab repertoire into an IgG expression plasmid. The linkage between previously selected LC/HC pairs needs to be retained. This is achieved in a first cloning step, in which the complete Fab fragment is transferred into the eukaryotic expression construct. In a second cloning step, regulatory elements, important for HC expression, are introduced (see sections 6.1, 6.2 and 6.4). The second step is not related to retaining of the linkage between pre-selected LC/HC pairs. When a mixture of Fabs is batch reformatted, it is necessary to analyze a significantly higher number of output antibody clones, compared to input Fabs, to ensure their re-identification.

It is typically possible to generate antibodies with natural HC sequences from Fabs derived from the CJ library, no matter if reformatted into pBRV (6.2) or pRRV (6.1). This is due to the presence of a unique Mfe1 site, introduced at the 5' end of the VH region of each CJ Fab. Mfe1 rarely cuts within antibody V genes. Due to this unique feature of the CJ library, the transfer of an individual Fab to pRRV (as described in 6.1) can be performed in a "batch reformatting type" procedure; in a first step the complete Fab, lifted from the phage by PCR, is inserted into pRRV.

Preferred procedure for batch reformatting of CJ Fabs to unaltered IgG antibodies:

Two special features of the CJ library, already mentioned above, facilitate batch reformat a mixture of Fabs to unaltered antibodies, by use of PCR:
1. Possibility to obtain natural human antibody HC by "cut and paste" (without DNA sequence modification).
2. Only a very small number of VL specific primers (1 kappa, 4 lambda; see 6.1) are needed for amplification of all Fabs contained in the library. At the same time, these primers also introduce "natural" LC N-termini.

In addition, PCR amplification of Fab fragments from the phages might be more feasible than propagation of al large number of phages, and isolation of a sufficient amount of phage DNA to perform "cut and paste" reformatting. Individual Fabs are amplified from phage in separate, parallel PCR reactions. The combined mixture of Fab fragments/PCR products will be batch transferred into pRRV, using the approach described in 6.1 for an individual CJ Fab. To re-identify the "starting Fabs", a significantly higher number of antibody constructs have to be sequenced. The Fab portion of the reformatted antibody can be sequenced to verify PCR fidelity.

6.1 Transfer of Individual CJ Fabs to pRRV

In a first step the CJ Fab is lifted from the display vector via PCR. One primer, containing an Nhe1 site, anneals to the CH1 region of the HC. This Nhe1 site is compatible to the one introduced into the CH1 region in the antibody expression vectors, pRRV and pBRV. The other primer contains an ApaL1 site, (compatible with correct processing of the eukaryotic leader/signal peptide (L) of pRRV) and anneals to the 5' end of VL. Because of conservation of N-terminal amino acid sequences of λ and κ LC of CJ Fabs, only a small number (5) of VL specific primers are needed to amplify most Fab clones of the CJ library. The ApaL1/Nhe1 cut PCR fragment of about 1.1 kb is inserted into pRRV.

In a second step internal/regulatory elements are exchanged via Asc1 and Mfe1. The Asc1/Mfe1 fragment encoding IRES and an "Ab-leader" sequence (fragment size: ~0.7 kb) should be taken from pShuttleI. (An internal fragment carrying the Ab-leader and a more efficient IRES2 element, as judged from recent/preliminary expression experiments, can be taken from pShuttleIII.) As explained above, it is also possible to transfer a mixture of CJ Fabs in batch to pRRV, after separate PCR amplification of individual clones.

Recommended PCR Primers for Amplification of CJ Fabs:

Primers Specific for VL Genes of the CJ Library:

κ:

```
                                          (SEQ ID NO: 35)
            ApaL1
5'-ATATAT GTG CAC TCT GAC ATC CAG ATG ACC CAG TC
                                          (SEQ ID NO: 36)
            V   H   S   D   I   Q   M   T   Q   S
```

λ:
```
                                          (SEQ ID NO: 37)
            ApaL1
5'-ATATAT GTG CAC TCA CAG AGC GTC TTG ACT C
                                          (SEQ ID NO: 38)
            V   H   S   Q   S   V   L   T
                                          (SEQ ID NO: 39)
            ApaL1
5'-ATATAT GTG CAC TCA CAG AGC GCT TTG ACT C
                                          (SEQ ID NO: 40)
            V   H   S   Q   S   A   L   T
                                          (SEQ ID NO: 41)
            APAL1
5'-ATATAT GTG CAC TCA AGC TAC GAA TTG ACT C
                                          (SEQ ID NO:42)
            V   H   S   S   Y   E   L   T
                                          (SEQ ID NO: 43)
            ApaL1
5'-ATATAT GTG CAC TCA CAG AGC GAA TTG ACT C
                                          (SEQ ID NO: 44)
            V   H   S   Q   S   E   L   T
```

The sequence underlined has to be added to the N-terminus of the light chain. The sequence "ATATAT" represents a variable overhang, facilitating efficient ApaL1 cleavage of the PCR product.

CH1 Specific Primer:

```
                                          (SEQ ID NO: 45)
                       NheI
        5'-GGA GGG TGC TAG CGG GAA GAC CG-3'
```

A mismatch at the position of the introduced Nhe1 site does not influence the performance of this primer.

Recommended PCR conditions: (e.g., using 2Advantage HF polymerase from Clontech.) 25-30 cycles of:

1 min. annealing at 55° C.

1.5 min. extension at 68° C.

30 sec. denaturation at 96° C.

6.2 Transfer of CJ Fabs to pBRV by "Cut and Paste"

Referring to FIG. 5, in the first step an ApaL1/BstE2 fragment of about 1.1 kb is released from the display construct and inserted into pBRV. (The ApaL1 site in pBRV corresponds to the one in the display vector. This compatibility leads to the addition of one alanine-residue to the "natural" N-terminus of the LC.). In a second step internal/regulatory elements are exchanged via Asc1 and Mfe1. The Asc1/Mfe1 fragment, encoding IRES and an "Ab-leader" sequence (fragment size: ~0.7 kb), should be taken from pShuttleI. (An internal fragment carrying the Ab-leader and a IRES2 element can be taken from pShuttleIII.). The method can be adapted, e.g., for individual Fabs and Fab-repertoires.

6.3 Transfer of Individual TQ Fabs to pRRV

Figure 18:
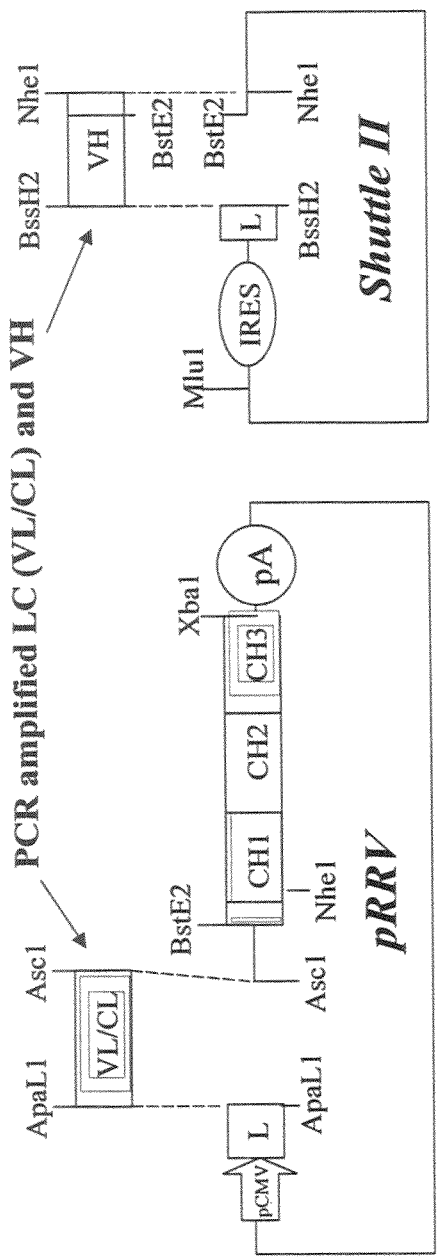

Referring to FIGS. 18 and 19, in a first step the LC and the VH region of the Fab are amplified from the display vector by PCR. Upon cutting with appropriate restriction endonucleases, the LC is inserted into pRRV and VH into the Shuttle vector, respectively. In case of the LC one primer has to be specific for the 5' end of the VL region of the individual clone and will also introduce the ApaL1 site, compatible with correct processing of the eukaryotic leader/signal peptide (L) of pRRV. The second primer has to be "display vector specific". The LC is inserted into pRRV as ApaL1/Asc1 fragment (~0.6 kb).

For VH amplification one primer has to be specific for the 5' end of VH, and will also introduce a BssH2 site, compatible with correct processing of the eukaryotic leader/signal peptide (L) included in the Shuttle vector. The second primer anneals to the CH1 region of the Fab. This primer also contains an Nhe1 site, compatible to the one introduced into the CH region, present in the antibody expression vectors, pRRV and pBRV. VH is inserted in pShuttleII as BssH2/Nhe1 fragment (~0.4 kb).

In the second step, the Mlu1/Nhe1 fragment of pShuttleII (+VH) is inserted into pRRV (+LC). The ~1.0 kb fragment excised from the Shuttle vector also includes the IRES motif. The pRRV construct has to be cut with Asc1 and Nhe1. Asc1 and Mlu1 create compatible 5' overhangs.

In the procedure outlined above the pShuttleIII vector can be used in place of pShuttleII. This constructs contains the IRES2 motif that can contribute to higher antibody expression levels.

PCR Amplification of Vgenes of an Individual TQ-Fab:

This method can use, e.g., "clone specific" forward/sense primers. Furthermore, the VL and VH specific primers need to include additional sequences, compatible to the leader sequences in pRRV and pShuttle, respectively. The junctions of leader sequences and Vgene N-termini are shown below:

```
pRRV:
                                          (SEQ ID NO: 46)
     ApaLI
  GGCGTGCACTCT (SEQ ID NO: 47)
     G  V  H  S - VL pShuttle
                                          (SEQ ID NO: 48)
     BssHII
  GGCGCGCACTCC (SEQ ID NO: 49)
     G  A  H  S - VH
```

The reverse/antisense primers bind to the plasmid backbone of the display vector (pCES):

For LC amplification one can use a primer binding in the "ribosome binding site":

```
                                          (SEQ ID NO: 50)
5'-TCC AGC GGC TGC CGT AGG CAA TAG-3'  (pCESrbrev)
```

For VH amplification the CH1 specific primer mentioned in 6.1 can be used:

```
                                          (SEQ ID NO: 51)
              NheI
    5'-GGA GGG TGC TAG CGG GAA GAC CG-3'
```

6.4 Transfer of TQ Fabs to pBRV by "Cut and Paste"

(Individual Fabs and Fab-Repertoires)

Figure 20:
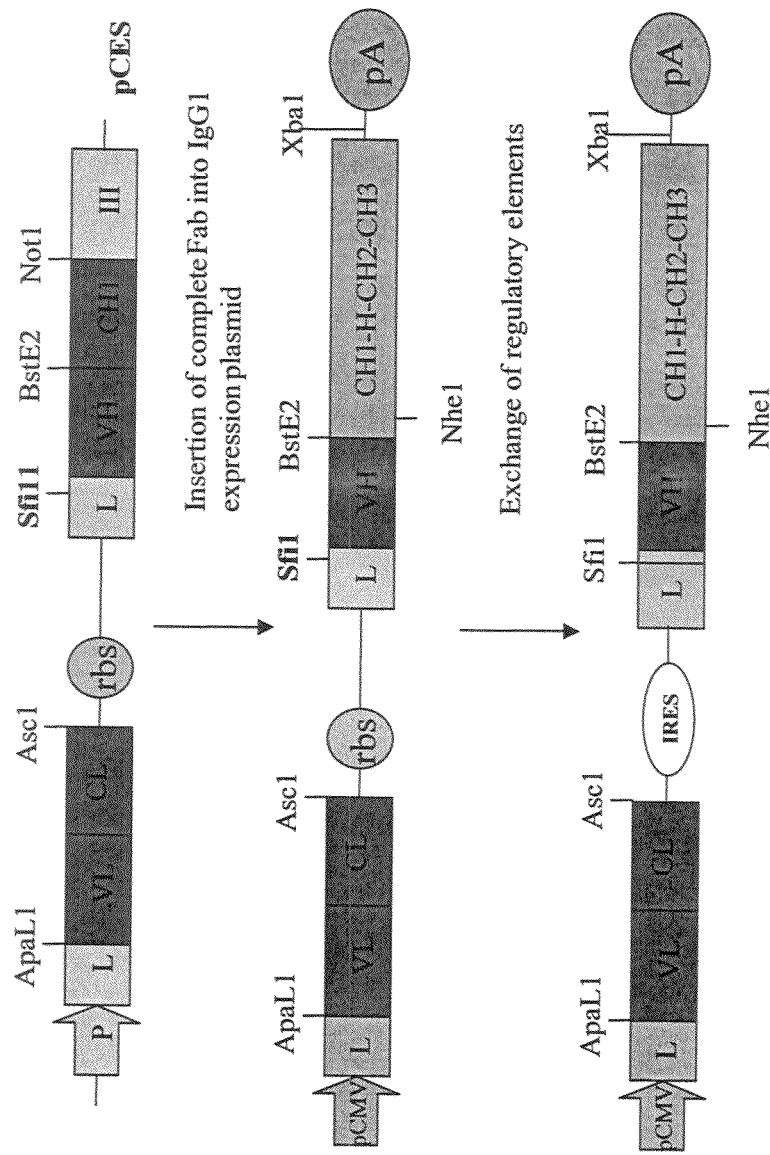

Referring to FIG. 20, in the first step an ApaL1/BstE2 fragment (~1.1 kb) is released from the display construct and inserted into pBRV. (The ApaL1 site in pBRV is corresponding to the one in the display vector. This compatibility leads to the addition of one alanine-residue to the "natural" N-terminus of the LC.) In a second step internal regulatory elements are exchanged via Asc1 and Sfi1. The Asc1/Sfi1 fragment (~0.7 kb) can be taken from pBlue/IRES/Sfi1. This fragment contains the IRES motif and a modified "viral signal peptide" (derived from HCMV). Because of utilization of the Sfi1 site of the prokaryotic PelB leader, the six C-terminal amino acids "AQPAMA" (SEQ ID NO:52) of the PelB leader are included in the eukaryotic signal peptide.

6.5 Variations of Reformatting of Individual Fabs (CJ or TQ) into pBRV

This example can be used, e.g., to transfer Fabs with additional BstE2 sites.

Figure 21:
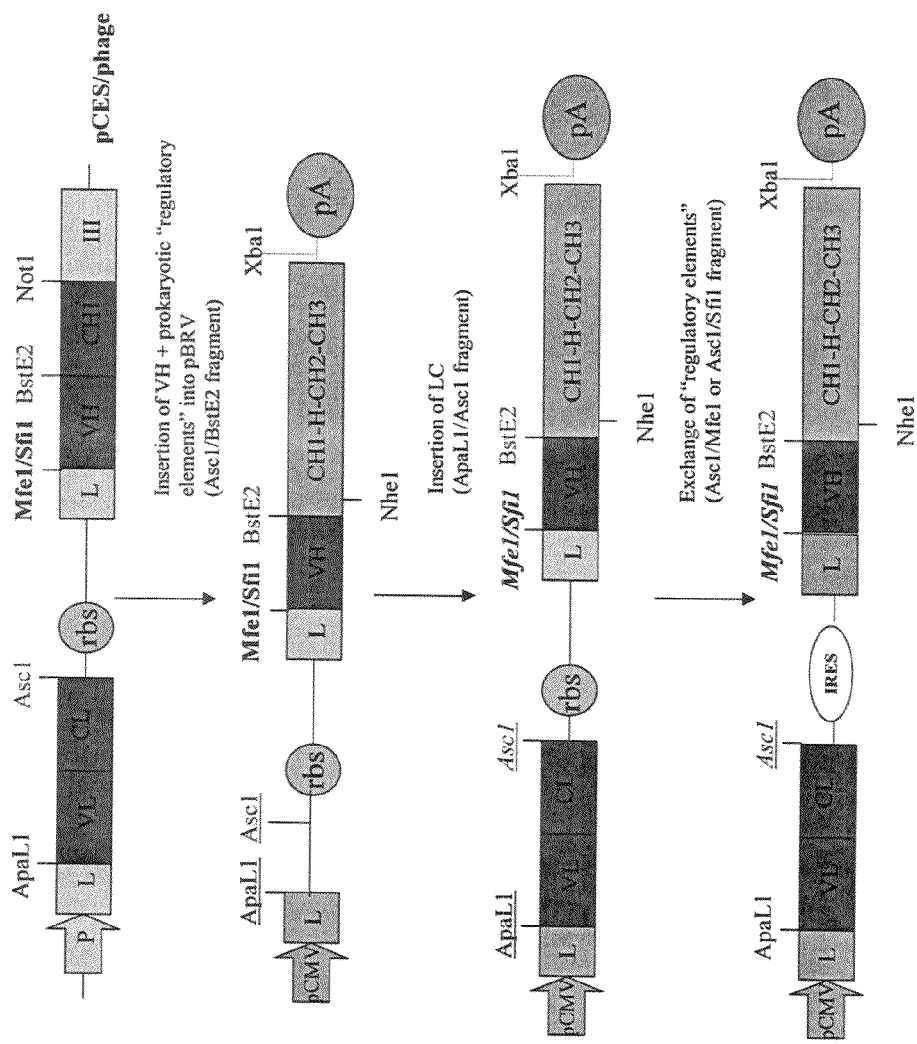

As described in 6.2 and 6.4 Fabs from the present and the new Dyax library are cloned into pBRV using ApaL1 and the BstE2 (unique in VH, cuts in FR4). Unfortunately, BstE2 also cuts in a portion (~10-20%) of VL genes. Two alternative strategies for the transfer of such Fabs into pBRV are shown below:

Variant 1: "Cut and paste" transfer in 3-steps—VH is inserted into the vector before LC. Referring to FIG. 21, the construct is assembled in an order that does not conflict with additional BstE2 sites in VL: 1) An Asc1/BstE2 fragment (~0.4-0.5 kb) of the Fab insert of the phage or phagemid is cloned into pBRV. This fragment contains VH. 2) insertion of the LC into pBRV as ApaL1/Asc1 fragment (~0.6 kb). 3) Introduction of eukaryotic regulatory elements (Asc1/Mfe1 fragment for CJ Fabs and Asc1/Sfi1 fragment for TQ Fabs) (fragment size: ~0.7 kb)

Variant 2: Cloning of a PCR-amplified Fab into pBRV. Referring to FIG. 5, the Fab (~1.1 kb) is lifted from the phage using vector/backbone specific PCR primer. One primer binds 5' of VL, the other in CH1. The CH1 specific primer also contains an Nhe1 site, compatible to the one introduced in the CH1 region within the antibody expression vector pBRV. The Fab is inserted into pBRV as ApaL1/Nhe1 fragment. The exchange of regulatory sequences (second step) is performed as described in 6.1 and 6.2. (A ~0.7 kb fragment encoding the IRES motif and an Ab-leader is introduced.)

PCR Primers:

Forward Primer Binding in LacZ Promoter: (Example)

```
                                          (SEQ ID NO: 53)
       5'-AGC GGA TAA CAA TTT CAC ACA GG-3'
```

Reverse Primer Binding in CH1 (Including a Nhe1 Site, Underscored): (See Also 6.1)

(SEQ ID NO: 54)
5'-GGA GGG TGC TAG CGG GAA GAC CG-3'

Recommended PCR Conditions:

25-30 cycles of:

1 min. annealing at 55° C.

1.5 min. extension at 68° C.

30 sec. denaturation at 96° C.

7.1 Recommended Sequencing Primers for "Clone Verification" and Sequencing of Complete Fab Fragments, Reformatted into pBRV or pRRV:

Primers that bind in the CMV promoter and the CH1 region and that are useful for clone verification include, for example:

pCMV Forward Primer:

(SEQ ID NO: 55)
5'-CGC AAA TGG GCG GTA GGC GTG-3'

(reading into 5'-VL)

CH1 (Reverse/Antisense):

(SEQ ID NO: 56)
5'-GTC CTT GAC CAG GCA GCC CAG GGC-3'

(reading into 3'-VH)

These primers anneal within the internal fragment, e.g. the IRES motif, which is introduced in the second reformatting step.

Alternatively, sequencing of the entire Fab is possible after the first reformatting step. Primers binding to prokaryotic internal sequences (ribosome binding site) can be used:

pCESrbrev:

(SEQ ID NO: 57)
5'-TCC AGC GGC TGC CGT AGG CAA TAG-3'

(reading into the constant region (3') of the LC)

pCESrb (forward/sense):

(SEQ ID NO: 58)
5'-GCG CCA ATT CTA TTT CAA GG-3'

(reading into 5'-VH)

Other embodiments are within the following claims.

---

What is claimed:

1. A method for evaluating display library members, the method comprising:
providing a first plurality of nucleic acid library members, each library member encoding a first immunoglobulin or functional fragment thereof that is displayed on the surface of a prokaryotic cell, wherein each library member comprises a first nucleic acid sequence encoding a first immunoglobulin variable domain, a second nucleic acid sequence encoding a second immunoglobulin variable domain, and a ribosomal binding site disposed between the first and second nucleic acid sequences, wherein the first and second nucleic acid sequences are in the same translational orientation and can be transcribed as a single transcript;
determining an assessment for each library member with respect to a property;
sorting information about the assessments of the library members in a computer database;
filtering the information to identify a subset of the library members, wherein the subset of library members is smaller than the total number of library members; and
reformatting each library member of the subset for expression in a mammalian cell such that each reformatted library member encodes a second immunoglobulin or functional fragment thereof that comprises a first immunoglobulin variable domain, a second immunoglobulin variable domain, and an effector domain not encoded by the nucleic acids of the first plurality.

2. The method of claim 1, wherein the display library members comprise phage display library members.

3. The method of claim 1, wherein the determining comprises contacting the first immunoglobulin or functional fragment thereof encoded by the library member to a target.

4. The method of claim 3, wherein the subset of the library members encode one or more immunoglobulins or functional fragments thereof that bind to the target.

5. The method of claim 3, comprising contacting a protein array with the target, a protein corresponding to each library member being present at an address of the array.

6. The method of claim 1, wherein the property is a functional property.

7. The method of claim 6, wherein the functional property is a binding activity.

8. The method of claim 1, wherein the reformatting is en masse.

9. The method of claim 8, wherein the reformatting maintains linkage between the first nucleic acid sequence and the second nucleic acid sequence.

10. The method of claim 1, wherein the reformatting further comprises inserting a segment that comprises an internal ribosome entry site between the first and second nucleic acid sequences.

11. The method of claim 1, wherein the effector domain comprises immunoglobulin heavy chain constant regions 2 and 3 (CH2 and CH3, respectively).

12. The method of claim 1, wherein the second immunoglobulin or functional fragment thereof is glycosylated at Asn 297.

13. The method of claim 1, wherein the second immunoglobulin or functional fragment thereof can elicit antibody-dependent cell-mediated cytotoxicity (ADCC) or complement dependent cytotoxicity (CDC).

14. The method of claim 1, wherein the second immunoglobulin functional fragment comprises a Fab structure.

15. The method of claim 1, further comprising introducing reformatted members into mammalian cells to form a plurality of expression cells that can produce the second immunoglobulin or functional fragment thereof.

16. The method of claim 15, wherein the second immunoglobulin or functional fragment thereof comprises a constant region that comprises the effector domain.

17. The method of claim 16, wherein the mammalian cells express a heterologous protein that is attached to the cell surface and recognizes the constant region.

18. The method of claim 15, further comprising screening the expression cells to identify cells that produce at least a threshold amount of the second immunoglobulin or functional fragment thereof.

19. The method of claim 1, further comprising assaying one or more second immunoglobulins or functional fragments thereof for a first function property.

20. The method of claim 19, wherein the assaying depends on an activity that is independent on the effector domain.

21. The method of claim 19, further comprising entering results of the assaying for the first function property into a machine-accessible medium.

22. The method of claim 21, wherein the medium comprises identifiers for the library members.

23. The method of claim 19, further comprising assaying one or more second immunoglobulins or functional fragments thereof for a second function property.

24. The method of claim 23, wherein the assaying depends on an activity that is dependent on the effector domain.

25. The method of claim 19, further comprising entering results of the assaying for the second function property into a machine-accessible medium.

26. The method of claim 25, wherein the medium comprises identifiers for the library members.

27. The method of claim 1, further comprising assaying one or more second immunoglobulins or functional fragments thereof for a cell-mediated activity, a biochemical property, a structural property, or a physiological property.

28. The method of claim 19, further comprising selecting one or more second immunoglobulins or functional fragments thereof that meet a criterion based on the assaying.

29. The method of claim 28, further comprising mutagenizing the selected second immunoglobulins or functional fragments thereof.

* * * * *

SEQUENCE LISTING

```
<160> NUMBER OF SEQ ID NOS: 58

<210> SEQ ID NO 1
<211> LENGTH: 20
<212> TYPE: PRT
<213> ORGANISM: Artificial Sequence
<220> FEATURE:
<223> OTHER INFORMATION: synthetically generated leader sequence

<400> SEQUENCE: 1

Met Ala Arg Arg Leu Trp Ile Leu Ser Leu Leu Ala Val Thr Leu Thr
 1               5                  10                  15

Val Ala Leu Ala
            20

<210> SEQ ID NO 2
<211> LENGTH: 19
<212> TYPE: PRT
<213> ORGANISM: Artificial Sequence
<220> FEATURE:
<223> OTHER INFORMATION: synthetically generated leader sequence

<400> SEQUENCE: 2

Met Gly Trp Ser Cys Ile Ile Leu Phe Leu Val Ala Thr Ala Thr Gly
 1               5                  10                  15

Ala His Ser

<210> SEQ ID NO 3
<211> LENGTH: 4
<212> TYPE: PRT
<213> ORGANISM: Artificial Sequence
<220> FEATURE:
<223> OTHER INFORMATION: exemplary motif

<400> SEQUENCE: 3

Glu Val Gln Leu
```

<210> SEQ ID NO 4
<211> LENGTH: 993
<212> TYPE: DNA
<213> ORGANISM: Artificial Sequence
<220> FEATURE:
<221> NAME/KEY: CDS
<222> LOCATION: (1)...(990)
<220> FEATURE:
<223> OTHER INFORMATION: synthetically generated plasmid sequence

<400> SEQUENCE: 4

```
gcc tcc acc aag ggc cca tcg gtc ttc ccg cta gca ccc tcc tcc aag      48
Ala Ser Thr Lys Gly Pro Ser Val Phe Pro Leu Ala Pro Ser Ser Lys
 1               5                  10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
             20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
     50                  55                  60 ctc agc agc gta gtg acc gtg ccc tcc agc agc ttg ggc acc cag acc     240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                 85                  90                  95 aaa gtt gag ccc aaa tct tgt gac aaa act cac aca tgc cca ccg tgc     336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag     720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat     768
Leu Thr Lys Asn Gln Val Ser Leu Thr Cys Leu Val Lys Gly Phe Tyr
                245                 250                 255
```

| | | | | | | | | | | | | | | |
|---|---|---|---|---|---|---|---|---|---|---|---|---|---|---|
| ccc | agc | gac | atc | gcc | gtg | gag | tgg | gag | agc | aat | ggg | cag | ccg | gag | aac | 816
| Pro | Ser | Asp | Ile | Ala | Val | Glu | Trp | Glu | Ser | Asn | Gly | Gln | Pro | Glu | Asn |
| | | | 260 | | | | 265 | | | | 270 | | | | |
| aac | tac | aag | acc | acg | cct | ccc | gtg | ctg | gac | tcc | gac | ggc | tcc | ttc | ttc | 864
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| ctc | tac | agc | aag | ctc | acc | gtg | gac | aag | agc | agg | tgg | cag | cag | ggg | aac | 912
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| gtc | ttc | tca | tgc | tcc | gtg | atg | cat | gag | gct | ctg | cac | aac | cac | tac | acg | 960
| Val | Phe | Ser | Cys | Ser | Val | Met | His | Glu | Ala | Leu | His | Asn | His | Tyr | Thr |
| 305 | | | | 310 | | | | | 315 | | | | | 320 | |
| cag | aag | agc | ctc | tcc | ctg | tct | ccg | ggt | aaa | tga | | | | | | 993
| Gln | Lys | Ser | Leu | Ser | Leu | Ser | Pro | Gly | Lys | | | | | | |
| | | | | 325 | | | | | 330 | | | | | | |

<210> SEQ ID NO 5
<211> LENGTH: 993
<212> TYPE: DNA
<213> ORGANISM: Artificial Sequence
<220> FEATURE:
<223> OTHER INFORMATION: synthetically generated plasmid sequence

<400> SEQUENCE: 5

| | |
|---|---|
| tcatttaccc ggagacaggg agaggctctt ctgcgtgtag tggttgtgca gagcctcatg | 60 |
| catcacggag catgagaaga cgttcccctg ctgccacctg ctcttgtcca cggtgagctt | 120 |
| gctgtagagg aagaaggagc cgtcggagtc cagcacggga ggcgtggtct tgtagttgtt | 180 |
| ctccggctgc ccattgctct cccactccac ggcgatgtcg ctgggataga agcctttgac | 240 |
| caggcaggtc aggctgacct ggttcttggt cagctcatcc cgggatgggg cagggtgta | 300 |
| cacctgtggt tctcggggct gccctttggc tttggagatg gttttctcga tggggctgg | 360 |
| gagggctttg ttggagacct tgcacttgta ctccttgcca ttcagccagt cctggtgcag | 420 |
| gacggtgagg acgctgacca cacgtacgt gctgttgtac tgctcctccc gcggctttgt | 480 |
| cttggcatta tgcacctcca cgccgtccac gtaccagttg aacttgacct cagggtcttc | 540 |
| gtggctcacg tccaccacca cgcatgtgac ctcaggggtc cggagatca tgagggtgtc | 600 |
| cttgggtttt gggggaaga ggaagactga cggtcccccc aggagttcag gtgctgggca | 660 |
| cggtgggcat gtgtgagttt tgtcacaaga tttgggctca actttcttgt ccaccttggt | 720 |
| gttgctgggc ttgtgattca cgttgcagat gtaggtctgg gtgcccaagc tgctggaggg | 780 |
| cacggtcact acgctgctga gggagtgag tccggaggac tgtaggacag ccggaaggt | 840 |
| gtggacgccg ctggtcaggg cgcctgagtt ccacgacacc gtcaccggtt cggggaagta | 900 |
| gtccttgacc aggcagccca gggccgctgt gccccagag gtgctcttgg aggagggtgc | 960 |
| tagcgggaag accgatgggc ccttggtgga ggc | 993 |

<210> SEQ ID NO 6
<211> LENGTH: 330
<212> TYPE: PRT
<213> ORGANISM: Artificial Sequence
<220> FEATURE:
<223> OTHER INFORMATION: synthetically generated plasmid sequence

<400> SEQUENCE: 6

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 225
<212> TYPE: DNA
<213> ORGANISM: Artificial Sequence
<220> FEATURE:
<221> NAME/KEY: CDS
<222> LOCATION: (3)...(47)
<220> FEATURE:
<221> NAME/KEY: CDS
<222> LOCATION: (130)...(141)
<220> FEATURE:
<221> NAME/KEY: CDS
<222> LOCATION: (174)...(224)
<220> FEATURE:
<223> OTHER INFORMATION: synthetically generated plasmid sequence

<400> SEQUENCE: 7 cc atg gga tgg agc tgt atc atc ctc ttc ttg gta gca aca gct aca    47
   Met Gly Trp Ser Cys Ile Ile Leu Phe Leu Val Ala Thr Ala Thr

```
                1               5                  10                 15
ggtaagggt   taacagtagc  aggcttgagg  tctggacata  tatatgggtg  acaatgacat    107
ccactttgcc  tttctctcca  ca ggc gtg cac tct aaggcgcgcc ataggcaatt          161
                          Gly Val His Ser gcccgcgctg tg gtc acc gtc tca agc gcc tcc acc aag ggc cca tcg gtc         212
              Val Thr Val Ser Ser Ala Ser Thr Lys Gly Pro Ser Val
                       20                  25                  30 ttc ccg cta gca c                                                         225
Phe Pro Leu Ala
        35

<210> SEQ ID NO 8
<211> LENGTH: 225
<212> TYPE: DNA
<213> ORGANISM: Artificial Sequence
<220> FEATURE:
<223> OTHER INFORMATION: synthetically generated plasmid sequence

<400> SEQUENCE: 8
gtgctagcgg gaagaccgat gggcccttgg tggaggcgct tgagacggtg accacagcgc         60
gggcaattgc ctatggcgcg ccttagagtg cacgcctgtg gagagaaagg caaagtggat       120
gtcattgtca cccatatata tgtccagacc tcaagcctgc tactgttaac cccttacctg       180
tagctgttgc taccaagaag aggatgatac agctccatcc catgg                       225

<210> SEQ ID NO 9
<211> LENGTH: 15
<212> TYPE: PRT
<213> ORGANISM: Artificial Sequence
<220> FEATURE:
<223> OTHER INFORMATION: synthetically generated plasmid sequence

<400> SEQUENCE: 9

Met Gly Trp Ser Cys Ile Ile Leu Phe Leu Val Ala Thr Ala Thr
1               5                   10                  15

<210> SEQ ID NO 10
<211> LENGTH: 4
<212> TYPE: PRT
<213> ORGANISM: Artificial Sequence
<220> FEATURE:
<223> OTHER INFORMATION: synthetically generated plasmid sequence

<400> SEQUENCE: 10

Gly Val His Ser
 1

<210> SEQ ID NO 11
<211> LENGTH: 17
<212> TYPE: PRT
<213> ORGANISM: Artificial Sequence
<220> FEATURE:
<223> OTHER INFORMATION: synthetically generated plasmid sequence

<400> SEQUENCE: 11

Val Thr Val Ser Ser Ala Ser Thr Lys Gly Pro Ser Val Phe Pro Leu
1               5                   10                  15
Ala

<210> SEQ ID NO 12
<211> LENGTH: 233
<212> TYPE: DNA
<213> ORGANISM: Artificial Sequence
```

<220> FEATURE:
<221> NAME/KEY: CDS
<222> LOCATION: (3)...(47)
<220> FEATURE:
<221> NAME/KEY: CDS
<222> LOCATION: (130)...(144)
<220> FEATURE:
<221> NAME/KEY: CDS
<222> LOCATION: (181)...(231)
<220> FEATURE:
<223> OTHER INFORMATION: synthetically generated plasmid sequence

<400> SEQUENCE: 12

```
cc atg gga tgg agc tgt atc atc ctc ttc ttg gta gca aca gct aca        47
   Met Gly Trp Ser Cys Ile Ile Leu Phe Leu Val Ala Thr Ala Thr
   1               5                  10                  15 ggtaagggt taacagtagc aggcttgagg tctggacata tatatgggtg acaatgacat     107
ccactttgcc tttctctcca ca ggc gcg cac agt gca ctctaaggcg              154
                         Gly Ala His Ser Ala
                                         20 cgccataggc aattgcccgc gctgtg gtc acc gtc tca agc gcc tcc acc aag     207
                             Val Thr Val Ser Ser Ala Ser Thr Lys
                                                     25 ggc cca tcg gtc ttc ccg cta gca cc                                   233
Gly Pro Ser Val Phe Pro Leu Ala
 30                  35
```

<210> SEQ ID NO 13
<211> LENGTH: 233
<212> TYPE: DNA
<213> ORGANISM: Artificial Sequence
<220> FEATURE:
<223> OTHER INFORMATION: synthetically generated plasmid sequence

<400> SEQUENCE: 13

```
ggtgctagcg ggaagaccga tgggcccttg gtggaggcgc ttgagacggt gaccacagcg     60
cgggcaattg cctatggcgc gccttagagt gcactgtgcg cgcctgtgga gagaaaggca    120
aagtggatgt cattgtcacc catatatatg tccagacctc aagcctgcta ctgttaaccc    180
cttacctgta gctgttgcta ccaagaagag gatgatacag ctccatccca tgg           233
```

<210> SEQ ID NO 14
<211> LENGTH: 15
<212> TYPE: PRT
<213> ORGANISM: Artificial Sequence
<220> FEATURE:
<223> OTHER INFORMATION: synthetically generated plasmid sequence

<400> SEQUENCE: 14

```
Met Gly Trp Ser Cys Ile Ile Leu Phe Leu Val Ala Thr Ala Thr
 1               5                  10                  15
```

<210> SEQ ID NO 15
<211> LENGTH: 5
<212> TYPE: PRT
<213> ORGANISM: Artificial Sequence
<220> FEATURE:
<223> OTHER INFORMATION: synthetically generated plasmid sequence

<400> SEQUENCE: 15

```
Gly Ala His Ser Ala
 1               5
```

<210> SEQ ID NO 16
<211> LENGTH: 17

```
<212> TYPE: PRT
<213> ORGANISM: Artificial Sequence
<220> FEATURE:
<223> OTHER INFORMATION: synthetically generated plasmid sequence

<400> SEQUENCE: 16

Val Thr Val Ser Ser Ala Ser Thr Lys Gly Pro Ser Val Phe Pro Leu
 1               5                  10                  15

Ala

<210> SEQ ID NO 17
<211> LENGTH: 80
<212> TYPE: DNA
<213> ORGANISM: Artificial Sequence
<220> FEATURE:
<221> NAME/KEY: CDS
<222> LOCATION: (8)...(79)
<223> OTHER INFORMATION: synthetically generated plasmid sequence

<400> SEQUENCE: 17 gtcgacc atg gct cgg agg cta tgg atc ttg agc tta cta gcc gtg acc        49
        Met Ala Arg Arg Leu Trp Ile Leu Ser Leu Leu Ala Val Thr
         1               5                  10 ttg acg gtg gct ttg gcg gaa gtt caa ttg a                              80
Leu Thr Val Ala Leu Ala Glu Val Gln Leu
 15                  20

<210> SEQ ID NO 18
<211> LENGTH: 80
<212> TYPE: DNA
<213> ORGANISM: Artificial Sequence
<220> FEATURE:
<223> OTHER INFORMATION: synthetically generated plasmid sequence

<400> SEQUENCE: 18
cagctggtac cgagcctccg atacctagaa ctcgaatgat cggcactgga actgccaccg      60
aaaccgcctt caagttaact                                                  80

<210> SEQ ID NO 19
<211> LENGTH: 24
<212> TYPE: PRT
<213> ORGANISM: Artificial Sequence
<220> FEATURE:
<223> OTHER INFORMATION: synthetically generated plasmid sequence

<400> SEQUENCE: 19

Met Ala Arg Arg Leu Trp Ile Leu Ser Leu Leu Ala Val Thr Leu Thr
 1               5                  10                  15

Val Ala Leu Ala Glu Val Gln Leu
                 20

<210> SEQ ID NO 20
<211> LENGTH: 79
<212> TYPE: DNA
<213> ORGANISM: Artificial Sequence
<220> FEATURE:
<221> NAME/KEY: CDS
<222> LOCATION: (7)...(78)
<223> OTHER INFORMATION: synthetically generated plasmid sequence

<400> SEQUENCE: 20 gtcgac atg gct cgg agg cta tgg atc ttg agc tta cta gcc gtg acc         48
       Met Ala Arg Arg Leu Trp Ile Leu Ser Leu Leu Ala Val Thr
        1               5                  10 ttg acg gtg gct ttg gcg gcc cag ccg gcc g                              79
```

```
Leu Thr Val Ala Leu Ala Ala Gln Pro Ala
 15                  20
```

```
<210> SEQ ID NO 21
<211> LENGTH: 79
<212> TYPE: DNA
<213> ORGANISM: Artificial Sequence
<220> FEATURE:
<223> OTHER INFORMATION: synthetically generated plasmid sequence

<400> SEQUENCE: 21
cagctgtacc gagcctccga tacctagaac tcgaatgatc ggcactggaa ctgccaccga    60
aaccgccggg tcggccggc                                                 79
```

```
<210> SEQ ID NO 22
<211> LENGTH: 24
<212> TYPE: PRT
<213> ORGANISM: Artificial Sequence
<220> FEATURE:
<223> OTHER INFORMATION: synthetically generated plasmid sequence

<400> SEQUENCE: 22

Met Ala Arg Arg Leu Trp Ile Leu Ser Leu Leu Ala Val Thr Leu Thr
 1               5                  10                  15

Val Ala Leu Ala Ala Gln Pro Ala
             20
```

```
<210> SEQ ID NO 23
<211> LENGTH: 93
<212> TYPE: DNA
<213> ORGANISM: Artificial Sequence
<220> FEATURE:
<221> NAME/KEY: CDS
<222> LOCATION: (3)...(71)
<223> OTHER INFORMATION: synthetically generated plasmid sequence

<400> SEQUENCE: 23 cc atg gga tgg agc tgt atc atc ctc ttc ttg gta gca aca gct aca      47
   Met Gly Trp Ser Cys Ile Ile Leu Phe Leu Val Ala Thr Ala Thr
    1               5                  10                  15 ggc gcg cac tcc gaa gtt caa ttg tgaggtcacc gctagcggcc gc             93
Gly Ala His Ser Glu Val Gln Leu
                20
```

```
<210> SEQ ID NO 24
<211> LENGTH: 93
<212> TYPE: DNA
<213> ORGANISM: Artificial Sequence
<220> FEATURE:
<223> OTHER INFORMATION: synthetically generated plasmid sequence

<400> SEQUENCE: 24
ggtaccctac ctcgacatag taggagaaga accatcgttg tcgatgtccg cgcgtgaggc    60
ttcaagttaa cactccagtg gcgatcgccg gcg                                 93
```

```
<210> SEQ ID NO 25
<211> LENGTH: 23
<212> TYPE: PRT
<213> ORGANISM: Artificial Sequence
<220> FEATURE:
<223> OTHER INFORMATION: synthetically generated plasmid sequence

<400> SEQUENCE: 25

Met Gly Trp Ser Cys Ile Ile Leu Phe Leu Val Ala Thr Ala Thr Gly
 1               5                  10                  15
```

Ala His Ser Glu Val Gln Leu
            20

<210> SEQ ID NO 26
<211> LENGTH: 93
<212> TYPE: DNA
<213> ORGANISM: Artificial Sequence
<220> FEATURE:
<221> NAME/KEY: CDS
<222> LOCATION: (3)...(71)
<223> OTHER INFORMATION: synthetically generated plasmid sequence

<400> SEQUENCE: 26

```
cc atg gga tgg agc tgt atc atc ctc ttc ttg gta gca aca gct aca        47
   Met Gly Trp Ser Cys Ile Ile Leu Phe Leu Val Ala Thr Ala Thr
    1               5                   10                  15 ggc gcg cac tcc gaa gtt caa ttg tgaggtcacc gctagcggcc gc              93
Gly Ala His Ser Glu Val Gln Leu
                20
```

<210> SEQ ID NO 27
<211> LENGTH: 93
<212> TYPE: DNA
<213> ORGANISM: Artificial Sequence
<220> FEATURE:
<223> OTHER INFORMATION: synthetically generated plasmid sequence

<400> SEQUENCE: 27
ggtaccctac ctcgacatag taggagaaga accatcgttg tcgatgtccg cgcgtgaggc     60
ttcaagttaa cactccagtg gcgatcgccg gcg                                   93

<210> SEQ ID NO 28
<211> LENGTH: 23
<212> TYPE: PRT
<213> ORGANISM: Artificial Sequence
<220> FEATURE:
<223> OTHER INFORMATION: synthetically generated plasmid sequence

<400> SEQUENCE: 28

Met Gly Trp Ser Cys Ile Ile Leu Phe Leu Val Ala Thr Ala Thr Gly
 1               5                   10                  15

Ala His Ser Glu Val Gln Leu
            20

<210> SEQ ID NO 29
<211> LENGTH: 93
<212> TYPE: DNA
<213> ORGANISM: Artificial Sequence
<220> FEATURE:
<221> NAME/KEY: CDS
<222> LOCATION: (3)...(71)
<223> OTHER INFORMATION: synthetically generated plasmid sequence

<400> SEQUENCE: 29

```
cc atg gga tgg agc tgt atc atc ctc ttc ttg gta gca aca gct aca        47
   Met Gly Trp Ser Cys Ile Ile Leu Phe Leu Val Ala Thr Ala Thr
    1               5                   10                  15 ggc gcg cac tcc gaa gtt caa ttg tgaggtcacc gctagcggcc gc              93
Gly Ala His Ser Glu Val Gln Leu
                20
```

<210> SEQ ID NO 30
<211> LENGTH: 93
<212> TYPE: DNA
<213> ORGANISM: Artificial Sequence

```
<220> FEATURE:
<223> OTHER INFORMATION: synthetically generated plasmid sequence

<400> SEQUENCE: 30
ggtaccctac ctcgacatag taggagaaga accatcgttg tcgatgtccg cgcgtgaggc    60
ttcaagttaa cactccagtg gcgatcgccg gcg                                 93

<210> SEQ ID NO 31
<211> LENGTH: 23
<212> TYPE: PRT
<213> ORGANISM: Artificial Sequence
<220> FEATURE:
<223> OTHER INFORMATION: synthetically generated plasmid sequence

<400> SEQUENCE: 31

Met Gly Trp Ser Cys Ile Ile Leu Phe Leu Val Ala Thr Ala Thr Gly
 1               5                  10                  15

Ala His Ser Glu Val Gln Leu
            20

<210> SEQ ID NO 32
<211> LENGTH: 4
<212> TYPE: PRT
<213> ORGANISM: Homo sapiens

<400> SEQUENCE: 32

Lys Asp Glu Leu
 1

<210> SEQ ID NO 33
<211> LENGTH: 19
<212> TYPE: PRT
<213> ORGANISM: Artificial Sequence
<220> FEATURE:
<223> OTHER INFORMATION: synthetically generated leader sequence

<400> SEQUENCE: 33

Met Gly Trp Ser Cys Ile Ile Leu Phe Leu Val Ala Thr Ala Thr Gly
 1               5                  10                  15

Val His Ala

<210> SEQ ID NO 34
<211> LENGTH: 19
<212> TYPE: PRT
<213> ORGANISM: Artificial Sequence
<220> FEATURE:
<223> OTHER INFORMATION: synthetically generated leader sequence

<400> SEQUENCE: 34

Val Lys Lys Leu Leu Phe Ala Ile Pro Leu Val Val Pro Phe Tyr Ser
 1               5                  10                  15

Val His Ala

<210> SEQ ID NO 35
<211> LENGTH: 35
<212> TYPE: DNA
<213> ORGANISM: Artificial Sequence
<220> FEATURE:
<221> NAME/KEY: CDS
<222> LOCATION: (7)...(35)
<223> OTHER INFORMATION: primer

<400> SEQUENCE: 35 atatat gtg cac tct gac atc cag atg acc cag tc                       35
```

```
                    Val His Ser Asp Ile Gln Met Thr Gln
                     1               5
```

<210> SEQ ID NO 36
<211> LENGTH: 10
<212> TYPE: PRT
<213> ORGANISM: Artificial Sequence
<220> FEATURE:
<223> OTHER INFORMATION: primer

<400> SEQUENCE: 36

```
Val His Ser Asp Ile Gln Met Thr Gln Ser
 1               5                  10
```

<210> SEQ ID NO 37
<211> LENGTH: 31
<212> TYPE: DNA
<213> ORGANISM: Artificial Sequence
<220> FEATURE:
<221> NAME/KEY: CDS
<222> LOCATION: (7)...(30)
<223> OTHER INFORMATION: primer

<400> SEQUENCE: 37

```
atatat gtg cac tca cag agc gtc ttg act c                    31
       Val His Ser Gln Ser Val Leu Thr
        1               5
```

<210> SEQ ID NO 38
<211> LENGTH: 8
<212> TYPE: PRT
<213> ORGANISM: Artificial Sequence
<220> FEATURE:
<223> OTHER INFORMATION: primer

<400> SEQUENCE: 38

```
Val His Ser Gln Ser Val Leu Thr
 1               5
```

<210> SEQ ID NO 39
<211> LENGTH: 31
<212> TYPE: DNA
<213> ORGANISM: Artificial Sequence
<220> FEATURE:
<221> NAME/KEY: CDS
<222> LOCATION: (7)...(30)
<223> OTHER INFORMATION: primer

<400> SEQUENCE: 39

```
atatat gtg cac tca cag agc gct ttg act c                    31
       Val His Ser Gln Ser Ala Leu Thr
        1               5
```

<210> SEQ ID NO 40
<211> LENGTH: 8
<212> TYPE: PRT
<213> ORGANISM: Artificial Sequence
<220> FEATURE:
<223> OTHER INFORMATION: primer

<400> SEQUENCE: 40

```
Val His Ser Gln Ser Ala Leu Thr
 1               5
```

<210> SEQ ID NO 41
<211> LENGTH: 31
<212> TYPE: DNA
<213> ORGANISM: Artificial Sequence

```
<220> FEATURE:
<221> NAME/KEY: CDS
<222> LOCATION: (7)...(30)
<223> OTHER INFORMATION: primer

<400> SEQUENCE: 41 atatat gtg cac tca agc tac gaa ttg act c                              31
       Val His Ser Ser Tyr Glu Leu Thr
       1               5

<210> SEQ ID NO 42
<211> LENGTH: 8
<212> TYPE: PRT
<213> ORGANISM: Artificial Sequence
<220> FEATURE:
<223> OTHER INFORMATION: primer

<400> SEQUENCE: 42

Val His Ser Ser Tyr Glu Leu Thr
1               5

<210> SEQ ID NO 43
<211> LENGTH: 31
<212> TYPE: DNA
<213> ORGANISM: Artificial Sequence
<220> FEATURE:
<221> NAME/KEY: CDS
<222> LOCATION: (7)...(30)
<223> OTHER INFORMATION: primer

<400> SEQUENCE: 43 atatat gtg cac tca cag agc gaa ttg act c                              31
       Val His Ser Gln Ser Glu Leu Thr
       1               5

<210> SEQ ID NO 44
<211> LENGTH: 8
<212> TYPE: PRT
<213> ORGANISM: Artificial Sequence
<220> FEATURE:
<223> OTHER INFORMATION: primer

<400> SEQUENCE: 44

Val His Ser Gln Ser Glu Leu Thr
1               5

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
ggagggtgct agcgggaaga ccg                                             23

<210> SEQ ID NO 46
<211> LENGTH: 12
<212> TYPE: DNA
<213> ORGANISM: Artificial Sequence
<220> FEATURE:
<221> NAME/KEY: CDS
<222> LOCATION: (1)...(12)
<223> OTHER INFORMATION: synthetically generated vector sequence

<400> SEQUENCE: 46 ggc gtg cac tct                                                       12
Gly Val His Ser
```

```
<210> SEQ ID NO 47
<211> LENGTH: 4
<212> TYPE: PRT
<213> ORGANISM: Artificial Sequence
<220> FEATURE:
<223> OTHER INFORMATION: synthetically generated vector sequence

<400> SEQUENCE: 47

Gly Val His Ser
 1

<210> SEQ ID NO 48
<211> LENGTH: 12
<212> TYPE: DNA
<213> ORGANISM: Artificial Sequence
<220> FEATURE:
<221> NAME/KEY: CDS
<222> LOCATION: (1)...(12)
<223> OTHER INFORMATION: synthetically generated vector sequence

<400> SEQUENCE: 48 ggc gcg cac tcc                                                       12
Gly Ala His Ser
 1

<210> SEQ ID NO 49
<211> LENGTH: 4
<212> TYPE: PRT
<213> ORGANISM: Artificial Sequence
<220> FEATURE:
<223> OTHER INFORMATION: synthetically generated vector sequence

<400> SEQUENCE: 49

Gly Ala His Ser
 1

<210> SEQ ID NO 50
<211> LENGTH: 24
<212> TYPE: DNA
<213> ORGANISM: Artificial Sequence
<220> FEATURE:
<223> OTHER INFORMATION: primer

<400> SEQUENCE: 50
tccagcggct gccgtaggca atag                                            24

<210> SEQ ID NO 51
<211> LENGTH: 23
<212> TYPE: DNA
<213> ORGANISM: Artificial Sequence
<220> FEATURE:
<223> OTHER INFORMATION: primer

<400> SEQUENCE: 51
ggagggtgct agcgggaaga ccg                                             23

<210> SEQ ID NO 52
<211> LENGTH: 6
<212> TYPE: PRT
<213> ORGANISM: Artificial Sequence
<220> FEATURE:
<223> OTHER INFORMATION: synthetically generated leader sequence

<400> SEQUENCE: 52

Ala Gln Pro Ala Met Ala
```

```
<210> SEQ ID NO 53
<211> LENGTH: 23
<212> TYPE: DNA
<213> ORGANISM: Artificial Sequence
<220> FEATURE:
<223> OTHER INFORMATION: primer

<400> SEQUENCE: 53
agcggataac aatttcacac agg                                              23

<210> SEQ ID NO 54
<211> LENGTH: 23
<212> TYPE: DNA
<213> ORGANISM: Artificial Sequence
<220> FEATURE:
<223> OTHER INFORMATION: primer

<400> SEQUENCE: 54
ggagggtgct agcgggaaga ccg                                              23

<210> SEQ ID NO 55
<211> LENGTH: 21
<212> TYPE: DNA
<213> ORGANISM: Artificial Sequence
<220> FEATURE:
<223> OTHER INFORMATION: primer

<400> SEQUENCE: 55
cgcaaatggg cggtaggcgt g                                                21

<210> SEQ ID NO 56
<211> LENGTH: 24
<212> TYPE: DNA
<213> ORGANISM: Artificial Sequence
<220> FEATURE:
<223> OTHER INFORMATION: primer

<400> SEQUENCE: 56
gtccttgacc aggcagccca gggc                                             24

<210> SEQ ID NO 57
<211> LENGTH: 24
<212> TYPE: DNA
<213> ORGANISM: Artificial Sequence
<220> FEATURE:
<223> OTHER INFORMATION: primer

<400> SEQUENCE: 57
tccagcggct gccgtaggca atag                                             24

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gcgccaattc tatttcaagg                                                  20
```